United States Patent
Devalaraja-Narashimha et al.

(10) Patent No.: US 10,765,762 B2
(45) Date of Patent: Sep. 8, 2020

(54) HUMANIZED MODEL OF KIDNEY AND LIVER DISORDERS

(71) Applicant: Regeneron Pharmaceuticals, Inc., Tarrytown, NY (US)

(72) Inventors: Kishor Devalaraja-Narashimha, Tarrytown, NY (US); Lori Morton, Tarrytown, NY (US); Yifan Luo, Tarrytown, NY (US); Cong Huang, Tarrytown, NY (US); Karolina Meagher, Tarrytown, NY (US); Sarah Casanova, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/904,808

(22) Filed: Feb. 26, 2018

(65) Prior Publication Data
US 2018/0243450 A1  Aug. 30, 2018

Related U.S. Application Data

(60) Provisional application No. 62/583,780, filed on Nov. 9, 2017, provisional application No. 62/529,916, filed on Jul. 7, 2017, provisional application No. 62/464,262, filed on Feb. 27, 2017.

(51) Int. Cl.
| | |
|---|---|
| A61K 49/00 | (2006.01) |
| A61P 13/12 | (2006.01) |
| C12N 15/113 | (2010.01) |
| C07K 16/18 | (2006.01) |
| G01N 33/50 | (2006.01) |
| C07K 14/47 | (2006.01) |
| A01K 67/027 | (2006.01) |
| A61K 39/00 | (2006.01) |

(52) U.S. Cl.
CPC ...... *A61K 49/0008* (2013.01); *A01K 67/0278* (2013.01); *A61P 13/12* (2018.01); *C07K 14/472* (2013.01); *C07K 16/18* (2013.01); *C12N 15/113* (2013.01); *G01N 33/5088* (2013.01); *A01K 2217/072* (2013.01); *A01K 2227/105* (2013.01); *A01K 2267/0368* (2013.01); *A61K 2039/505* (2013.01)

(58) Field of Classification Search
CPC ......... A61K 49/0008; A61K 2039/505; G01N 33/5088; C07K 14/472; C07K 16/18; A01K 67/0278; A01K 2227/105; A01K 2217/072; A01K 2267/0368; A61P 13/12; C12N 15/113
USPC .................................................. 800/3, 18, 9
See application file for complete search history.

(56) References Cited

U.S. PATENT DOCUMENTS

| | | |
|---|---|---|
| 9,795,121 B2 | 10/2017 | Hu et al. |
| 2015/0313194 A1 | 11/2015 | Hu et al. |

FOREIGN PATENT DOCUMENTS

| | | | |
|---|---|---|---|
| WO | 2010/054403 A1 | 5/2010 | |
| WO | 2013/152024 A1 | 10/2013 | |
| WO | 2015/171523 A1 | 11/2015 | |
| WO | WO/2015/171523 | * | 11/2015 |

OTHER PUBLICATIONS

De Vries et al. (2003) Transplantation, vol. 75(3) 375-382.*
Cheng et al. (2008) Transplant. Proceed., vol. 40(7), 2167-2170.*
Janssen et al. (2007) Mol. Innnnunol., vol. 44, 3-10.*
Drouin S.M. et al, "Cutting Edge: The Absence of C3 Demonstrates a Role for Complement in Th2 Effector Functions in a Murine Model of Pulmonary Allergy", The Journal of Immunology 167:4141-4145 (2001).
Flierl M.A. et al., "Functions of the Complement Components C3 and C5 During Sepsis", The FASEB Journal 22 (10):3483-3490 (Oct. 2008).
Latuszek A. et al., "Evaluation of Complement Activity in Wild Type, C5 Knockout and Humanized Mice for Drug Discovery", Investigative Ophthalmology & Visual Science 55:1324 (Apr. 2014), Abstract.
Makrides S.C., "Therapeutic Inhibition of the Complement System", Pharmacological Reviews 50(1):59-87 (1998).
Mollnes T.E. et al., "Strategies of Therapeutic Complement Inhibition", Molecular Immunology 43:107-121 (2006).
Pickering M.G. et al., "C3 Glomerulopathy: Consensus Report", Kidney International 84:1079-1089 (2013).
Vik D.P. et al., "Structural Features of the Human C3 Gene: Intron/Exon Organization Transcriptional Start Site, and Promoter Region Sequence", Biochemistry 30:1080-1085 (1991).
Barbour T.D. et al., "Complement Receptor 3 Mediates Renal Protection in Experimental C3 Glomerulopathy", Kideny International 89:823-832 (2016).
Hayashi H. et al., "Animals Models for the Study of Liver Fibrosis: New Insights from Knockout Mouse Models", Am J Physiol Gastrointest Liver Physiol 300:G729-G738 (2011).
Nester, M.D. C.M. et al., "Treatment Options for C3 Glomerulopathy", Curr Opin Nephrol Hypertens 22(2):231-237 (Mar. 2013).

(Continued)

*Primary Examiner* — Anne Marie S Wehbe
(74) *Attorney, Agent, or Firm* — Scully, Scott, Murphy & Presser, P.C.; Eileen Woo

(57) ABSTRACT

Provided herein, inter alia, are non-human animals comprising nucleic acid sequences encoding a C3 protein that comprises a human sequence as well as transgenic non-human animals comprising a C3 gene that is human in whole or in part as well as methods for using the same to screen for candidate therapeutic molecules to treat complement-related nephropathies. Also provided herein are methods for improving kidney function in an individual diagnosed with or thought to have a complement-related nephropathy.

16 Claims, 44 Drawing Sheets
(37 of 44 Drawing Sheet(s) Filed in Color)
Specification includes a Sequence Listing.

(56) References Cited

OTHER PUBLICATIONS

Sendler M. et al., "Complement Component 5 Mediates Development of Fibrosis, via Activation of Stellate Cells, in 2 Mouse Models of Chronic Pancreatitis", Gastroenterology 149(3):765-776 (2015).

International Search Report and Written Opinion dated May 29, 2018 received in International Application No. PCT/US2018/019651.

* cited by examiner

Top enriched pathways in MAID6156 or 6149 liver

FIG. 18

| Symbol | HO.vs.WT_ heart _MAID6156 | HO.vs.WT_ kidney _MAID6156 | HO.vs.WT_ liver _MAID61 56 | HO.vs.WT_ spleen _MAID6156 | HO.vs.WT_heart _MAID6149 | HO.vs.WT_ kidney _MAID6149 | HO.vs.WT_ liver _MAID61 49 | HO.vs.WT_ spleen _MAID6149 | Description |
|---|---|---|---|---|---|---|---|---|---|
| (P-value) | '1' | '0.206' | | | '0.189' | '0.211' | '1' | '1' | (Enrichment P-vals) |
| Timp1 | | | 15.63 | | | | | | tissue inhibitor of metalloproteinase 1 |
| S100a4 | | | 4.88 | | | | | | S100 calcium binding protein A4 |
| Serpine1 | | | 4.38 | | | | | | serine (or cysteine) peptidase inhibitor, clade E, member 1 |
| Ddr1 | | | 4.26 | | | | | | discoidin domain receptor family, member 1 |
| Col3a1 | | | 3.75 | 1.63 | | | | | collagen, type III, alpha 1 |
| Cd40 | | | 3.69 | | | | | | CD40 antigen |
| Col1a1 | | | 3.65 | 1.75 | | | | | collagen, type I, alpha 1 |
| Plat | | | 2.94 | | | | | | plasminogen activator, tissue |
| Pdgfa | | | | | | | | | platelet derived growth factor, alpha |
| Pdgfrb | | | 2.20 | | | | | | platelet derived growth factor receptor, beta polypeptide |
| F2rl1 | | | | | | | | | coagulation factor II (thrombin) receptor-like 1 |
| Cdh1 | | | 2.10 | | | | | | Cadherin 1 |
| Vim | | | 1.99 | | | | | | vimentin |
| Mmp2 | | | | | | | | | Matrix metallopeptidase 2 |
| Pdgfd | | | | | | | | | platelet derived growth factor, D polypeptide |
| Hgf | | | 1.80 | | | | | | Hepatocyte growth factor |
| Tlr4 | | | | | | | | | toll-like receptor 4 |
| Acta2 | | | | | | | | | actin, alpha 2, smooth muscle, aorta |
| Pdgfra | | | | | | | | | platelet derived growth factor receptor, alpha polypeptide |
| Tgfb1 | | | | | | | | | transforming growth factor, beta 1 |
| Ddr2 | | | | | | | | | discoidin domain receptor family, member 2 |
| Pdgfb | | | | | | | | | platelet derived growth factor, B polypeptide |
| Edn1 | | | | | | | | | endothelin 1 |
| Ctgf | | | | | 2.74 | 1.75 | | | connective tissue growth factor |
| Grem2 | | | | | | | | | gremlin 2 homolog, cysteine knot superfamily |
| Wisp1 | | | | | | | | | WNT1 inducible signaling pathway protein 1 |
| Smad3 | | | | | 0.99 | | | | SMAD family member 3 |
| Twsg1 | | | | | | | | | twisted gastrulation protein homolog 1 (Drosophila) |
| Chrdl1 | | | | | | | | | chordin-like 1 |

FIG. 19

| | | | | | |
|---|---|---|---|---|---|
| Snai2 | , | , | , | , | snail homolog 2 (Drosophila) |
| Angptl4 | , | 1.94 | , | , | angiopoietin-like 4 |
| Bmp7 | , | , | , | , | bone morphogenetic protein 7 |
| Cd40lg | , | , | , | , | CD40 ligand |
| Fgf2 | , | , | , | , | fibroblast growth factor 2 |
| Grem1 | 5.74 | , | , | , | gremlin 1 |
| Il13 | | | | | interleukin 13 |
| Il4 | | | | | interleukin 4 |
| Mmp13 | , | , | , | , | Matrix metallopeptidase 13 |
| Snai1 | , | , | , | , | snail homolog 1 (Drosophila) |
| Tnf | , | , | , | , | tumor necrosis factor |
| Twist1 | , | , | , | , | twist basic helix-loop-helix transcription factor 1 |

| Symbol | huC3_vs_WT | Description |
|---|---|---|
| Gpnmb | 24.38 | glycoprotein (transmembrane) nmb |
| Lcn2 | 20.02 | lipocalin 2 |
| Timp1 | 19.13 | tissue inhibitor of metalloproteinase 1 |
| Havcr1 | 15.19 | hepatitis A virus cellular receptor 1 |
| Fgb | 15.09 | fibrinogen beta chain |
| Cd44 | 10.24 | CD44 antigen |
| Ugt1a1 | 9.69 | UDP glucuronosyltransferase 1 family, polypeptide A1 |
| Vcam1 | 9.31 | vascular cell adhesion molecule 1 |
| Socs3 | 7.07 | suppressor of cytokine signaling 3 |
| Ctss | 5.62 | cathepsin S |
| Atf3 | 5.24 | activating transcription factor 3 |
| Ugt1a6a | 5.07 | UDP glucuronosyltransferase 1 family, polypeptide A6A |
| Mgp | 4.97 | matrix Gla protein |
| Cdkn1a |  | cyclin-dependent kinase inhibitor 1A (P21) |
| Spp1 | 4.81 | secreted phosphoprotein 1 |
| Gc | 4.16 | group specific component |
| Vim | 4.04 | vimentin |
| Fn1 | 4.02 | fibronectin 1 |
| Abcb1a | 3.94 | ATP-binding cassette, sub-family B (MDR/TAP), member 1A |
| Bmp1 | 3.92 | bone morphogenetic protein 1 |
| Cp | 3.84 | ceruloplasmin |
| Cxcl10 |  | chemokine (C-X-C motif) ligand 10 |
| Lgals3 | 3.09 | lectin, galactose binding, soluble 3 |
| Tmsb10 | 2.75 | thymosin, beta 10 |
| Nqo1 | 2.56 | NAD(P)H dehydrogenase, quinone 1 |
| Btg2 | 2.32 | B cell translocation gene 2, anti-proliferative |
| Clu | 2.28 | clusterin |
| Tnfrsf12a | 2.13 | tumor necrosis factor receptor superfamily, member 12a |
| Sprr1a |  | small proline-rich protein 1A |
| Anxa5 | 1.88 | annexin A5 |
| Cd24a | 1.86 | CD24a antigen |
| Hmox1 | 1.83 | heme oxygenase (decycling) 1 |
| Mt1 |  | metallothionein 1 |
| Rtn4 |  | reticulon 4 |
| Cst3 |  | cystatin C |
| Gpx8 |  | glutathione peroxidase 8 (putative) |
| Uchl1 |  | ubiquitin carboxy-terminal hydrolase L1 |
| G6pdx |  | glucose-6-phosphate dehydrogenase X-linked |
| Mcm6 |  | minichromosome maintenance deficient 6 (MIS5 homolog, S. pombe) (S. cerevisiae) |
| Gadd45a |  | growth arrest and DNA-damage-inducible 45 alpha |

FIG. 21C

| Symbol | huC3 vs_WT | Description | sec.tm | chrom |
|---|---|---|---|---|
| Timp1 | 19.13 | tissue inhibitor of metalloproteinase 1 | S | X |
| Cd44 | 10.24 | CD44 antigen | PM | 2 |
| Mmp12 | 9.43 | matrix metallopeptidase 12 | S | 9 |
| Vcam1 | 9.3 | vascular cell adhesion molecule 1 | PM | 3 |
| Itgam | 8.77 | integrin alpha M | | 7 |
| Thbs2 | 8.58 | thrombospondin 2 | | 17 |
| Col1a1 | 7.02 | collagen, type I, alpha 1 | S | 11 |
| Mmp2 | 6.86 | matrix metallopeptidase 2 | C,M,N,MT,S | 8 |
| Col3a1 | | collagen, type III, alpha 1 | S | 1 |
| Mmp14 | 6.56 | matrix metallopeptidase 14 (membrane-inserted) | C,V,PM | 14 |
| Itgax | 5.81 | integrin alpha X | PM | 7 |
| Col6a1 | 4.87 | collagen, type VI, alpha 1 | S | 10 |
| Spp1 | 4.81 | secreted phosphoprotein 1 | S | 5 |
| Cntn1 | | contactin 1 | PM | 15 |
| Cdh3 | 4.44 | cadherin 3 | PM | 8 |
| Adamts2 | 4.19 | a disintegrin-like and metallopeptidase (reprolysin type) with thrombospondin type 1 motif, 2 | S | 11 |
| Itgb2 | 4.19 | integrin beta 2 | PM | 10 |
| Tnc | 4.19 | tenascin C | S | 4 |
| Fn1 | 4.02 | fibronectin 1 | S | 1 |
| Tgfbi | 3.83 | transforming growth factor, beta induced | S | 13 |
| Postn | | periostin, osteoblast specific factor | G,S | 3 |
| Thbs3 | 3.75 | thrombospondin 3 | | 3 |
| Col5a1 | 3.38 | collagen, type V, alpha 1 | S | 2 |
| Fbln1 | 3.26 | fibulin 1 | S | 15 |
| Entpd1 | 3.08 | ectonucleoside triphosphate diphosphohydrolase 1 | PM | 19 |
| Itga4 | 3.06 | integrin alpha 4 | PM | 2 |
| Ctgf | | connective tissue growth factor | S | 10 |
| Mmp11 | | matrix metallopeptidase 11 | S | 10 |
| Sparc | 2.87 | secreted acidic cysteine rich glycoprotein | S | 11 |
| Timp2 | 2.85 | tissue inhibitor of metalloproteinase 2 | | 11 |
| Emilin1 | 2.75 | elastin microfibril interfacer 1 | S | 5 |
| Itgb4 | 2.74 | integrin beta 4 | | 11 |
| Adamts1 | 2.7 | a disintegrin-like and metallopeptidase (reprolysin type) with thrombospondin type 1 motif, 1 | S | 16 |
| Itga5 | 2.66 | integrin alpha 5 (fibronectin receptor alpha) | PM | 15 |
| Itgb3 | | integrin beta 3 | PM | 11 |
| Itgal | | integrin alpha L | | 7 |
| Itgae | | integrin alpha E, epithelial-associated | PM | 11 |
| Ncam1 | | neural cell adhesion molecule 1 | PM | 9 |
| Icam1 | 2.34 | intercellular adhesion molecule 1 | PM | 9 |
| Thbs1 | 2.08 | thrombospondin 1 | | 2 |
| Lama2 | 2.00 | laminin, alpha 2 | S | 10 |
| Col4a2 | 1.98 | collagen, type IV, alpha 2 | S | 8 | ing partial gene list, sorted by fold change)

FIG. 21D

| Symbol | huC3_vs WT | Description |
|---|---|---|
| Serpina3n | | serine (or cysteine) peptidase inhibitor, clade A, member 3N |
| Ccl2 | 31.35 | chemokine (C-C motif) ligand 2 |
| Il1rn | 19.28 | interleukin 1 receptor antagonist |
| Prlr | 9.74 | prolactin receptor |
| Tlr8 | 9.30 | toll-like receptor 8 |
| Siglec1 | 8.98 | sialic acid binding Ig-like lectin 1, sialoadhesin |
| C3ar1 | 8.96 | complement component 3a receptor 1 |
| Gfra2 | 8.33 | glial cell line derived neurotrophic factor family receptor alpha 2 |
| Ptafr | 7.38 | platelet-activating factor receptor |
| Cxcl1 | 6.18 | chemokine (C-X-C motif) ligand 1 |
| Tnfsf13b | 5.94 | tumor necrosis factor (ligand) superfamily, member 13b |
| Cd4 | | CD4 antigen |
| Ccr2 | 4.96 | chemokine (C-C motif) receptor 2 |
| Tlr1 | 4.91 | toll-like receptor 1 |
| Csf3r | 4.90 | colony stimulating factor 3 receptor (granulocyte) |
| Il7r | 4.88 | interleukin 7 receptor |
| Spp1 | 4.81 | secreted phosphoprotein 1 |
| Il18rap | | interleukin 18 receptor accessory protein |
| Cx3cr1 | 4.45 | chemokine (C-X3-C motif) receptor 1 |
| Dock2 | 4.34 | dedicator of cyto-kinesis 2 |
| Il1rl2 | 4.33 | interleukin 1 receptor-like 2 |
| Nfam1 | 4.32 | Nfat activating molecule with ITAM motif 1 |
| Fos | 4.23 | FBJ osteosarcoma oncogene |
| Itgb2 | 4.19 | integrin beta 2 |
| Lbp | 4.14 | lipopolysaccharide binding protein |
| Il1rl1 | 4.09 | interleukin 1 receptor-like 1 |
| Fn1 | 4.02 | fibronectin 1 |
| Osmr | 4.02 | oncostatin M receptor |
| Cd74 | 4.01 | CD74 antigen (invariant polypeptide of major histocompatibility complex, class II antigen-associated) |
| Scube1 | | signal peptide, CUB domain, EGF-like 1 |
| Ly86 | 3.93 | lymphocyte antigen 86 |
| Il18r1 | 3.82 | interleukin 18 receptor 1 |
| Ccr5 | 3.61 | chemokine (C-C motif) receptor 5 |
| Cxcl10 | | chemokine (C-X-C motif) ligand 10 |
| Tlr2 | 3.46 | toll-like receptor 2 |
| Aif1 | 3.45 | allograft inflammatory factor 1 |
| Il10ra | 3.43 | interleukin 10 receptor, alpha |
| Il21r | 3.41 | interleukin 21 receptor |
| Cybb | 3.40 | cytochrome b-245, beta polypeptide |
| Tlr9 | 3.32 | toll-like receptor 9 |

(displaying partial gene list, sorted by fold change)

FIG. 21E

| Symbol | huC3 vs WT | Description |
|---|---|---|
| Ccl2 | 31.35 | chemokine (C-C motif) ligand 2 |
| Cxcl1 | 6.18 | chemokine (C-X-C motif) ligand 1 |
| Adcy7 | 5.81 | adenylate cyclase 7 |
| Pik3r5 | 5.27 | phosphoinositide-3-kinase, regulatory subunit 5, p101 |
| Ccr2 | 4.96 | chemokine (C-C motif) receptor 2 |
| Ncf1 | 4.77 | neutrophil cytosolic factor 1 |
| Fgr | 4.70 | Gardner-Rasheed feline sarcoma viral (Fgr) oncogene homolog |
| Cx3cr1 | 4.45 | chemokine (C-X3-C motif) receptor 1 |
| Dock2 | 4.34 | dedicator of cyto-kinesis 2 |
| Pik3cg | 3.96 | phosphoinositide-3-kinase, catalytic, gamma polypeptide |
| Vav1 | 3.77 | vav 1 oncogene |
| Ccr5 | 3.63 | chemokine (C-C motif) receptor 5 |
| Cxcl10 | | chemokine (C-X-C motif) ligand 10 |
| Rac2 | 3.41 | RAS-related C3 botulinum substrate 2 |
| Plcb2 | 3.37 | phospholipase C, beta 2 |
| Itk | 3.20 | IL2 inducible T cell kinase |
| Hck | 3.14 | hemopoietic cell kinase |
| Was | 3.13 | Wiskott-Aldrich syndrome homolog (human) |
| Pik3cd | 2.87 | phosphatidylinositol 3-kinase catalytic delta polypeptide |
| Elmo1 | 2.84 | engulfment and cell motility 1 |
| Adcy3 | | adenylate cyclase 3 |
| Prkcb | 2.48 | protein kinase C, beta |
| Cxcl9 | | chemokine (C-X-C motif) ligand 9 |
| Stat3 | 2.22 | signal transducer and activator of transcription 3 |
| Gnb4 | 2.14 | guanine nucleotide binding protein (G protein), beta 4 |
| Xcr1 | | chemokine (C motif) receptor 1 |
| Prex1 | 2.06 | phosphatidylinositol-3,4,5-trisphosphate-dependent Rac exchange factor 1 |
| Arrb2 | 2.04 | arrestin, beta 2 |
| Cxcr4 | | chemokine (C-X-C motif) receptor 4 |
| Cxcl12 | | chemokine (C-X-C motif) ligand 12 |
| Adcy5 | 2.00 | adenylate cyclase 5 |
| Grk5 | 2.00 | G protein-coupled receptor kinase 5 |
| Gng2 | | guanine nucleotide binding protein (G protein), gamma 2 |
| Cxcl16 | 1.81 | chemokine (C-X-C motif) ligand 16 |
| Jak3 | 1.77 | Janus kinase 3 |
| Akt3 | 1.71 | thymoma viral proto-oncogene 3 |
| Cx3cl1 | 1.68 | chemokine (C-X3-C motif) ligand 1 |
| Vav3 | 1.68 | vav 3 oncogene |
| Nfkb1 | 1.67 | nuclear factor of kappa light polypeptide gene enhancer in B cells 1, p105 |
| Cxcl14 | | chemokine (C-X-C motif) ligand 14 |

(displaying partial gene list, sorted by fold change)

WT + Ctl Ab

HumIn + Ctl Ab

HumIn + M1M17628N

SEQUENCE LISTING

<160> NUMBER OF SEQ ID NOS: 27

<210> SEQ ID NO 1
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 1
ggcctgatta catggacctg tc                                          22

<210> SEQ ID NO 2
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 2
cccaggcttg gctggaatg                                              19

<210> SEQ ID NO 3
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 3
tgtccactct ggaagcccag gc                                          22

<210> SEQ ID NO 4
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 4
gccaggagag gaagctggag                                             20

<210> SEQ ID NO 5
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 5
tggctcagca gtaaagaaca c                                           21

<210> SEQ ID NO 6
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 6
acagattgct gtgagctgcc caaa                                        24

<210> SEQ ID NO 7
<211> LENGTH: 19
<212> TYPE: DNA
<213> ORGANISM: Artificial Sequence

```
<220> FEATURE:
<223> OTHER INFORMATION: synthetic oligonucleotide

<400> SEQUENCE: 7
ggtggagagg ctattcggc                                              19

<210> SEQ ID NO 8
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 8
gaacacggcg gcatcag                                                17

<210> SEQ ID NO 9
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 9
tgggcacaac agacaatcgg ctg                                         23

<210> SEQ ID NO 10
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 10
gccagcctag cctacttca                                              19

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 11
gccacccatc ccagttct                                               18

<210> SEQ ID NO 12
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 12
cagcccaggc cctttagatt gca                                         23

<210> SEQ ID NO 13
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 13
tacggtgtta ggttcactat tggt                                        24
```

```
<210> SEQ ID NO 14
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 14
gtcgccagca gtctcataca g                                             21

<210> SEQ ID NO 15
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 15
tgcggccgat cttagcc                                                  17

<210> SEQ ID NO 16
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 16
ttgaccgatt ccttgcgg                                                 18

<210> SEQ ID NO 17
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 17
gggcctccta agtttgttga gtatc                                         25

<210> SEQ ID NO 18
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 18
cagggctggt tccctagaaa tc                                            22

<210> SEQ ID NO 19
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 19
tacaatagca ggcacagcac cca                                           23

<210> SEQ ID NO 20
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 20
ggctgagagt gggagtcatg                                                  20

<210> SEQ ID NO 21
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 21
gcacttgcca atgccattat c                                                21

<210> SEQ ID NO 22
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 22
ctgctgtcct gcccatgtgg ttg                                              23

<210> SEQ ID NO 23
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 23
cgaatgccaa gacgaagaga ac                                               22

<210> SEQ ID NO 24
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 24
gggcacccaa agacaaccat                                                  20

<210> SEQ ID NO 25
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 25
cagaaacaat gccaggacct cggc                                             24

<210> SEQ ID NO 26
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 26
agtgggcatc ccttgccagg c                                                21

<210> SEQ ID NO 27

```
<211> LENGTH: 21
<212> TYPE: DNA
<213> ORGANISM: Artificial Sequence
<220> FEATURE:
<223> OTHER INFORMATION: synthetic oligonucleotide

<400> SEQUENCE: 27
acgagcgggt tcggcccatt c                                              21
```

HUMANIZED MODEL OF KIDNEY AND LIVER DISORDERS

CROSS REFERENCE TO RELATED APPLICATIONS

This application claims the benefit of priority from U.S. Provisional Application No. 62/464,262, filed Feb. 27, 2017, U.S. Provisional Application No. 62/529,916, filed Jul. 7, 2017, and U.S. Provisional Application No. 62/583,780, filed Nov. 9, 2017, the entire contents of all of which are incorporated herein by reference.

INCORPORATION BY REFERENCE OF SEQUENCE LISTING

The Sequence Listing in the ASCII text file, named as 35469_10207US01_SequenceListing.txt of 6 KB, created on Feb. 12, 2018, and submitted to the United States Patent and Trademark Office via EFS-Web, is incorporated herein by reference.

FIELD OF THE DISCLOSURE

Provided herein, inter alia, are methods for using genetically modified non-human animals comprising a C3 gene that is human in whole or in part to screen for candidate therapeutic agents or compounds for the treatment of complement-related nephropathies and fibrosis of the liver as well as methods for treating individuals diagnosed with or thought to have complement-related nephropathies.

BACKGROUND

Complement protein C3 is a therapeutic target for the treatment of a variety of human diseases, disorders, and conditions. Proteolytic cleavage of C3 by specific C3 convertases plays a major role in complement pathway activation. C3 convertases generate forms of C3b, which, in turn, are potential components of new C3 convertase molecules, thereby stimulating and amplifying the complement cascade.

Unwanted activation of the alternative complement pathway has been suggested as a possible cause of nephropathies such as atypical hemolytic uremic syndrome (aHUS) and C3 glomerulopathy (C3G), a form of membranoproliferative glomerulonephritis that encompass dense deposit disease (DDD) and C3 glomerulonephritis (C3GN). As they progress, these diseases harm and degrade kidney function. Since the glomerular membrane lacks endogenous complement regulatory membrane proteins that could otherwise inhibit complement pathway activation, continuous and unregulated cleavage of C3 occurs at this site in individuals with complement-related nephropathies, resulting in deposition of complement activation products, C3 convertase-mediated damage of the glomerular basement membranes, damage to epithelial tubules and endothelial cells, membrane thickening due to deposition of extracellular matrix, deposition of components of the complement system (e.g., C3 cleavage products) and, ultimately, defective filtration (proteinuria) and kidney failure.

Evaluation of the pharmacokinetics (PK) and pharmacodynamics (PD) of candidate therapeutic molecules that specifically target human C3 proteins for the treatment of complement-related nephropathies are routinely performed in non-human animals, e.g., rodents, e.g., mice or rats. However, the PD of such therapeutic molecules cannot properly be determined in certain non-human animals because these therapeutic molecules do not target the endogenous C3 proteins or genes.

Accordingly, there is a need for non-human animals, e.g., rodents, e.g., murine animals, e.g., mice or rats, in which the C3 genes of the non-human animal are humanized in whole or in part or replaced (e.g., at the endogenous non-human loci) with human C3 genes comprising sequences encoding human or humanized C3 proteins. Such animals could potentially serve as ideal models for assessing the efficacy of candidate therapeutics for the treatment of complement-related nephropathies, such as those associated with excessive activation of the alternative complement pathway due to pathological levels of C3 deposition in the kidney, particularly if the engineered non-human animals exhibit symptoms of these conditions corresponding to those observed in human disease.

Throughout this specification, various patents, patent applications and other types of publications (e.g., journal articles, electronic database entries, etc.) are referenced. The disclosure of all patents, patent applications, and other publications cited herein are hereby incorporated by reference in their entirety for all purposes.

SUMMARY OF THE DISCLOSURE

Provided herein, inter alia, are methods for using genetically modified non-human animals comprising a C3 gene that is human in whole or in part and which exhibit one or more symptoms corresponding to those observed in humans with a complement-related nephropathy and/or liver fibrosis to screen for or identify candidate therapeutic compounds or agents for the treatment of complement-related nephropathies and/or liver fibrosis. Also provided herein are methods for improving kidney function in an individual diagnosed with or thought to have a complement-related nephropathy.

Accordingly, in some aspects, provided herein are methods for assessing the in vivo therapeutic efficacy of an agent for use in a treatment of a complement-related nephropathy, the method comprising: (a) administering the agent to a rodent whose genome comprises a replacement at an endogenous rodent C3 locus of a rodent gene sequence comprising an exon of a C3 gene with a nucleic acid sequence comprising at least one exon of a human C3 gene to form a modified C3 gene, wherein expression of the modified C3 gene is under control of rodent regulatory elements at the endogenous rodent C3 locus; and (b) assessing if the agent inhibits (e.g., prevents, ameliorates or alleviates) one or more symptoms of the nephropathy compared to control rodents who have not been administered the agent. In some embodiments, the rodent is a mouse or a rat. In some embodiments, the nucleic acid sequence comprising at least one exon of a human C3 gene comprises exon 1 through exon 41 of the human C3 gene. In some embodiments, the nucleic acid sequence comprising at least one exon of a human C3 gene comprises exon 2 through exon 41 of the human C3 gene. In some embodiments, the rodent is a mouse that is incapable of expressing a mouse C3 protein. In some embodiments, the rodent is a mouse that expresses a mouse C5 protein encoded by an endogenous mouse C5 gene. In some embodiments, the agent is selected from the group consisting of small molecule chemical compounds, peptides and antibodies. In some embodiments, the agent is an antibody. In some embodiments, the agent is a monoclonal antibody or functional binding fragment thereof. In some embodiments, the agent is an inhibitory nucleic acid. In some embodiments, the inhibitory nucleic acid is selected from the group consisting of an siRNA, an shRNA, an aptamer, an antisense oligonucleotide, a triplex-forming oligonucleotide, and a ribozyme. In some embodiments, the one or more symptoms of the nephropathy include spontaneous death. In some embodiments, the one or more symptoms of the nephropathy include decreased weight, decreased bone density, decreased body fat, or a combination thereof. In some embodiments, the one or more symptoms of the nephropathy are selected from one or more of the group consisting of glomerulonephritis, basophilic tubules, sclerotic glomeruli, dilated tubules with protein casts, mesangial matrix expansion, glomerular hypertrophy, and mononuclear interstitial inflammation. In some embodiments, the one or more symptoms of the nephropathy include C3 protein deposition in the kidney. In some embodiments, the one or more symptoms of the nephropathy include the formation of C5b-9 membrane attack complexes in the kidney. In some embodiments, the one or more symptoms of the nephropathy include one or more of elevated blood urea nitrogen (BUN), serum lipase, serum cystatin C, or serum non-high density lipoproteins. In some embodiments, the one or more symptoms of C3 glomerulopathy include increased urinary albumin or urinary C5a. In some embodiments, the one or more symptoms of complement-related nephropathy are assessed by determining the expression of one or more of disease signature genes, i.e., genes that are differentially expressed in rodents having complement-related nephropathy as compared to wildtype rodents without complement-related nephropathy.

In another aspect, also provided herein are methods for assessing the in vivo therapeutic efficacy of an agent for use in a treatment for fibrosis of the liver, the method comprising: (a) administering the agent to a rodent whose genome comprises a replacement at an endogenous rodent C3 locus of a rodent gene sequence comprising an exon of a C3 gene with a nucleic acid sequence comprising at least one exon of a human C3 gene to form a modified C3 gene, wherein expression of the modified C3 gene is under control of rodent regulatory elements at the endogenous rodent C3 locus; and (b) assessing if the agent inhibits (e.g., prevents, ameliorates or alleviates) one or more symptoms of fibrosis of the liver compared to control rodents who have not been administered the agent. In some embodiments, the rodent is a mouse or a rat. In some embodiments, the nucleic acid sequence comprising at least one exon of a human C3 gene comprises exon 1 through exon 41 of the human C3 gene. In some embodiments, the nucleic acid sequence comprising at least one exon of a human C3 gene comprises exon 2 through exon 41 of the human C3 gene. In some embodiments, the rodent is a mouse that is incapable of expressing a mouse C3 protein. In some embodiments, the rodent is a mouse that expresses a mouse C5 protein encoded by an endogenous mouse C5 gene. In some embodiments, the agent is selected from the group consisting of small molecule chemical compounds, peptides and antibodies. In some embodiments, the agent is an antibody. In some embodiments, the agent is a monoclonal antibody or functional binding fragment thereof. In some embodiments, the agent is an inhibitory nucleic acid. In some embodiments, the inhibitory nucleic acid is selected from the group consisting of an siRNA, an shRNA, an aptamer, an antisense oligonucleotide, a triplex-forming oligonucleotide, and a ribozyme. In some embodiments, the one or more symptoms of fibrosis of the liver include one or more of elevated alanine aminotransferase (ALT), aspartate aminotransferase (AST), or alkaline phosphatase (ALP). In some embodiments, the one or more symptoms of fibrosis of the liver are assessed by determining the expression of one or more of disease signature genes, i.e., genes that are differentially expressed in rodents having fibrosis of the liver as compared to wildtype rodents without fibrosis of the liver.

In further aspects, provided herein is a method for identifying an agent that inhibits a symptom of a complement-related nephropathy in a rodent whose genome comprises a replacement at an endogenous rodent C3 locus of a rodent gene sequence comprising an exon of a C3 gene with a nucleic acid sequence comprising at least one exon of a human C3 gene to form a modified C3 gene, wherein expression of the modified C3 gene is under control of rodent regulatory elements at the endogenous rodent C3 locus, the method comprising: (a) administering the agent to the rodent; and (b) identifying the agent as an agent that inhibits a symptom of a complement-related nephropathy if the agent inhibits one or more symptoms of the complement-related nephropathy in the rodent. In some embodiments, the rodent is a mouse or a rat. In some embodiments, the nucleic acid sequence comprising at least one exon of a human C3 gene comprises exon 1 through exon 41 of the human C3 gene. In some embodiments, the nucleic acid sequence comprising at least one exon of a human C3 gene comprises exon 2 through exon 41 of the human C3 gene. In some embodiments, the rodent is a mouse that is incapable of expressing a mouse C3 protein. In some embodiments, the rodent is a mouse that expresses a mouse C5 protein encoded by an endogenous mouse C5 gene. In some embodiments, the agent is selected from the group consisting of small molecule chemical compounds, peptides and antibodies. In some embodiments, the agent is an antibody. In some embodiments, the agent is a monoclonal antibody or functional binding fragment thereof. In some embodiments, the agent is an inhibitory nucleic acid. In some embodiments, the inhibitory nucleic acid is selected from the group consisting of an siRNA, an shRNA, an aptamer, an antisense oligonucleotide, a triplex-forming oligonucleotide, and a ribozyme. In some embodiments, the one or more symptoms of the nephropathy include spontaneous death. In some embodiments, the one or more symptoms of the nephropathy include decreased weight, decreased bone density, decreased body fat, or a combination thereof. In some embodiments, the one or more symptoms of the nephropathy are selected from one or more of the group consisting of glomerulonephritis, basophilic tubules, sclerotic glomeruli, dilated tubules with protein casts, mesangial matrix expansion, glomerular hypertrophy, and mononuclear interstitial inflammation. In some embodiments, the one or more symptoms of the nephropathy include C3 protein deposition in the kidney. In some embodiments, the one or more symptoms of the nephropathy include the formation of C5b-9 membrane attack complexes in the kidney. In some embodiments, the one or more symptoms of the nephropathy include one or more of elevated blood urea nitrogen (BUN), serum lipase, serum cystatin C, or serum non-high density lipoproteins. In some embodiments, the one or more symptoms of C3 glomerulopathy include increased urinary albumin or urinary C5a. In some embodiments, the one or more symptoms of complement-related nephropathy are assessed by determining the expression of one or more of disease signature genes.

In yet other aspects, also provided herein is a rodent model of a human complement-related nephropathy, wherein the genome of the rodent comprises a modified C3 gene at an endogenous C3 locus, wherein the modified C3 gene comprises a nucleic acid sequence comprising at least one exon of a human C3 gene, and wherein expression of the modified C3 gene is under control of rodent regulatory elements at the endogenous rodent C3 locus. In some embodiments, the nucleic acid sequence is operatively linked to the endogenous rodent C3 promoter at the rodent C3 locus. In some embodiments, the rodent is a mouse or a rat. In some embodiments, the nucleic acid sequence comprising at least one exon of a human C3 gene comprises exon 1 through exon 41 of the human C3 gene. In some embodiments, the nucleic acid sequence comprising at least one exon of a human C3 gene comprises exon 2 through exon 41 of the human C3 gene. In some embodiments, the rodent is a mouse that is incapable of expressing a mouse C3 protein. In some embodiments, the rodent is a mouse that expresses a mouse C5 protein encoded by an endogenous mouse C5 gene. In some embodiments, the rodent exhibits one or more symptoms of a human complement-related nephropathy selected from the group consisting of spontaneous death, decreased weight, decreased bone density, decreased body fat, glomerulonephritis, basophilic tubules, sclerotic glomeruli, dilated tubules with protein casts, mesangial matrix expansion, glomerular hypertrophy, mononuclear interstitial inflammation, C3 protein deposition in the kidney, formation of C5b-9 membrane attack complexes in the kidney, elevated blood urea nitrogen (BUN), elevated serum lipase, elevated serum cystatin C, elevated serum non-high density lipoproteins, increased urinary albumin, increased urinary C5a, and a disease gene signature.

In another aspect, provided herein is a rodent model for assessing the therapeutic effectiveness of a candidate therapeutic agent for inhibiting a symptom of a complement-related nephropathy comprising (a) a rodent whose genome comprises a replacement at an endogenous rodent C3 locus of a rodent gene sequence comprising an exon of a C3 gene with a nucleic acid sequence comprising at least one exon of a human C3 gene to form a modified C3 gene, wherein expression of the modified C3 gene is under control of rodent regulatory elements at the endogenous rodent C3 locus, wherein the rodent exhibits one or more symptoms of a complement-related nephropathy; and (b) one or more candidate therapeutic agents. In some embodiments, the rodent is a mouse or a rat. In some embodiments, the nucleic acid sequence comprising at least one exon of a human C3 gene comprises exon 1 through exon 41 of the human C3 gene. In some embodiments, the nucleic acid sequence comprising at least one exon of a human C3 gene comprises exon 2 through exon 41 of the human C3 gene. In some embodiments, the rodent is a mouse that is incapable of expressing a mouse C3 protein. In some embodiments, the rodent is a mouse that expresses a mouse C5 protein encoded by an endogenous mouse C5 gene. In some embodiments, the agent is selected from the group consisting of small molecule chemical compounds, peptides and antibodies. In some embodiments, the agent is an antibody. In some embodiments, the agent is a monoclonal antibody or functional binding fragment thereof. In some embodiments, the agent is an inhibitory nucleic acid. In some embodiments, the inhibitory nucleic acid is selected from the group consisting of an siRNA, an shRNA, an aptamer, an antisense oligonucleotide, a triplex-forming oligonucleotide, and a ribozyme. In some embodiments, the one or more symptoms of the nephropathy include spontaneous death. In some embodiments, the one or more symptoms of the nephropathy include decreased weight, decreased bone density, decreased body fat, or a combination thereof. In some embodiments, the one or more symptoms of the nephropathy are selected from one or more of the group consisting of glomerulonephritis, basophilic tubules, sclerotic glomeruli, dilated tubules with protein casts, mesangial matrix expansion, glomerular hypertrophy, and mononuclear interstitial inflammation. In some embodiments, the one or more symptoms of the nephropathy include C3 protein deposition in the kidney. In some embodiments, the one or more symptoms of the nephropathy include the formation of C5b-9 membrane attack complexes in the kidney. In some embodiments, the one or more symptoms of the nephropathy include one or more of elevated blood urea nitrogen (BUN), serum lipase, serum cystatin C, or serum non-high density lipoproteins. In some embodiments, the one or more symptoms of C3 glomerulopathy is increased urinary albumin or urinary C5a. In some embodiments, the one or more symptoms of complement-related nephropathy are assessed by determining the expression of one or more of disease signature genes.

In further aspects, provided herein is a method for identifying an agent that inhibits fibrosis of the liver in a rodent whose genome comprises a replacement at an endogenous rodent C3 locus of a rodent gene sequence comprising an exon of a C3 gene with a nucleic acid sequence comprising at least one exon of a human C3 gene to form a modified C3 gene, wherein expression of the modified C3 gene is under control of rodent regulatory elements at the endogenous rodent C3 locus, the method comprising: (a) administering the agent to the rodent; and (b) identifying the agent as an agent that inhibits fibrosis of the liver if the agent inhibits one or more symptoms of fibrosis of the liver in the rodent. In some embodiments, the rodent is a mouse or a rat. In some embodiments, the nucleic acid sequence comprising at least one exon of a human C3 gene comprises exon 1 through exon 41 of the human C3 gene. In some embodiments, the human C3 gene encoding human C3 protein comprises exon 2 through exon 41 of the human C3 gene. In some embodiments, the rodent is a mouse that is incapable of expressing a mouse C3 protein. In some embodiments of any of the embodiments disclosed herein, the rodent is a mouse that expresses a mouse C5 protein encoded by an endogenous mouse C5 gene. In some embodiments, the agent is selected from the group consisting of small molecule chemical compounds, peptides and antibodies. In some embodiments, the agent is an antibody. In some embodiments, the agent is a monoclonal antibody or functional binding fragment thereof. In some embodiments, the agent is an inhibitory nucleic acid. In some embodiments, the inhibitory nucleic acid is selected from the group consisting of an siRNA, an shRNA, an aptamer, an antisense oligonucleotide, a triplex-forming oligonucleotide, and a ribozyme. In some embodiments, the one or more symptoms of fibrosis of the liver are one or more of elevated alanine aminotransferase (ALT), aspartate aminotransferase (AST), or alkaline phosphatase (ALP). In some embodiments, the one or more symptoms of fibrosis of the liver are assessed by determining the expression of one or more of disease signature genes.

In another aspect, provided herein is a rodent model of human fibrosis of the liver, wherein the genome of the rodent comprises a modified C3 gene at an endogenous C3 locus, wherein the modified C3 gene comprises a nucleic acid sequence comprising at least one exon of a human C3 gene, and wherein expression of the modified C3 gene is under control of rodent regulatory elements at the endogenous rodent C3 locus. In some embodiments, the nucleic acid sequence is operatively linked to the endogenous mouse C3 promoter at the rodent C3 locus. In some embodiments, the nucleic acid sequence is operatively linked to the endogenous rodent C3 promoter at the rodent C3 locus. In some embodiments, the rodent is a mouse or a rat. In some embodiments, the nucleic acid sequence comprising at least one exon of a human C3 gene comprises exon 1 through exon 41 of the human C3 gene. In some embodiments, the nucleic acid sequence comprising at least one exon of a human C3 gene comprises exon 2 through exon 41 of the human C3 gene. In some embodiments, the rodent is a mouse that is incapable of expressing a mouse C3 protein. In some embodiments, the rodent is a mouse that expresses a mouse C5 protein encoded by an endogenous mouse C5 gene. In some embodiments, the rodent exhibits one or more symptoms of liver fibrosis selected from the group consisting of elevated alanine aminotransferase (ALT), elevated aspartate aminotransferase (AST), and elevated alkaline phosphatase (ALP). In some embodiments, the one or more symptoms of fibrosis of the liver are assessed by determining the expression of one or more of disease signature genes.

In additional aspects, provided herein is a rodent model for assessing the therapeutic effectiveness of a candidate therapeutic agent for inhibiting a symptom fibrosis of the liver comprising (a) a rodent whose genome comprises a replacement at an endogenous rodent C3 locus of a rodent gene sequence comprising an exon of a C3 gene with a nucleic acid sequence comprising at least one exon of a human C3 gene to form a modified C3 gene, wherein expression of the modified C3 gene is under control of rodent regulatory elements at the endogenous rodent C3 locus, wherein the rodent exhibits one or more symptoms of fibrosis of the liver; and (b) one or more candidate therapeutic agents. In some embodiments, the rodent is a mouse or a rat. In some embodiments, the nucleic acid sequence comprising at least one exon of a human C3 gene comprises exon 1 through exon 41 of the human C3 gene. In some embodiments, the nucleic acid sequence comprising at least one exon of a human C3 gene encoding human C3 protein comprises exon 2 through exon 41 of the human C3 gene. In some embodiments, the rodent is a mouse that is incapable of expressing a mouse C3 protein. In some embodiments, the rodent is a mouse that expresses a mouse C5 protein encoded by an endogenous mouse C5 gene. In some embodiments, the agent is selected from the group consisting of small molecule chemical compounds, peptides and antibodies. In some embodiments, the agent is an antibody. In some embodiments, the agent is a monoclonal antibody or functional binding fragment thereof. In some embodiments, the agent is an inhibitory nucleic acid. In some embodiments, the inhibitory nucleic acid is selected from the group consisting of an siRNA, an shRNA, an aptamer, an antisense oligonucleotide, a triplex-forming oligonucleotide, and a ribozyme. In some embodiments, the one or more symptoms of fibrosis of the liver include one or more of elevated alanine aminotransferase (ALT), aspartate aminotransferase (AST), or alkaline phosphatase (ALP). In some embodiments, the one or more symptoms of fibrosis of the liver are assessed by determining the expression of one or more of disease signature genes.

In further aspects, provided herein are methods for treating an individual diagnosed with or thought to have a complement-related nephropathy or liver fibrosis comprising administering a clinically effective amount of a therapeutic to the individual. The therapeutic administered to an individual includes, for example, an agent that inhibits the expression or activity of C5, an agent that inhibits the expression or activity of C3, and an agent that inhibits the activity of the proteolytic cleavage products of C3 (C3a or C3b). The administration improves kidney or liver function, and ameliorate one or more symptoms of complement-related nephropathy or liver fibrosis.

In some embodiments, provided herein are methods for improving kidney function in an individual diagnosed with or thought to have a complement-related nephropathy comprising administering a clinically effective amount of a therapeutic, wherein the administration improves kidney function relative to individuals diagnosed with a complement-related nephropathy who have not been administered the therapeutic. In some embodiments, improved kidney function comprises one or more of decreased blood urea nitrogen (BUN) concentration, decreased serum cystatin C concentration, and/or decreased urinary C5a concentration. In some embodiments, a therapeutic that inhibits the expression or activity of C5 is administered, and BUN is decreased in the individual by about 10-50%. In some embodiments, a therapeutic that inhibits the expression or activity of C5 is administered, and, and serum cystatin C concentration is decreased in the individual by about 10-60%. In some embodiments, a therapeutic that inhibits the expression or activity of C5 is administered, and urinary C5a concentration is decreased in the individual by about 40-85%.

In other embodiments, provided herein are methods for decreasing glomerular membrane attack complex (MAC) formation in an individual diagnosed with or thought to have a complement-related nephropathy comprising administering a clinically effective amount of a therapeutic, wherein the administration decreases glomerular MAC formation relative to individuals diagnosed with a complement-related nephropathy who have not been administered the therapeutic. In some embodiments, a therapeutic that inhibits the expression or activity of C5 is administered, and MAC formation is decreased from about 5-20% in the individual. In some embodiments of any of the embodiments disclosed herein, MAC formation is determined by C9 deposition in glomerular tufts of the individual.

In still other embodiments, provided herein are methods for decreasing immune cell infiltration into the glomerulus or interstitium of a kidney of an individual diagnosed with or thought to have a complement-related nephropathy comprising administering a clinically effective amount of a therapeutic, wherein the administration decreases immune cell infiltration in the kidneys of the individual relative to individuals diagnosed with a complement-related nephropathy who have not been administered the therapeutic. In some embodiments, the immune cell is a neutrophil that infiltrates the glomerulus. In some embodiments, a therapeutic that inhibits the expression or activity of C5 is administered, and neutrophil infiltration of the glomerulus decreases by about 50-100%. In some embodiments, the immune cell is a macrophage that infiltrates the interstitium. In some embodiments, a therapeutic that inhibits the expression or activity of C5 is administered, and macrophage infiltration of the interstitium decreases by about 30-70%.

In some embodiments, provided herein are methods for decreasing glomerular size and/or mesangial matrix expansion in a kidney of an individual diagnosed with or thought to have a complement-related nephropathy comprising administering a clinically effective amount of a therapeutic, wherein the administration decreases glomerular size and/or mesangial matrix expansion in the kidneys of the individual relative to individuals diagnosed with a complement-related nephropathy who have not been administered the therapeutic. In some embodiments, a therapeutic that inhibits the expression or activity of C5 is administered, and glomerular size and/or mesangial matrix expansion decreases about 15-30%.

In some embodiments of any of the embodiments disclosed herein, the complement-related nephropathy is atypical hemolytic uremic syndrome (aHUS) or C3 glomerulopathy (C3G). In some embodiments, the C3G comprises dense deposit disease (DDD) or C3 glomerulonephritis (C3GN).

In some embodiments of any of the embodiments disclosed herein, the therapeutic (e.g., an agent that inhibits the expression or activity of C5, an agent that inhibits the expression or activity of C3, or an agent that inhibits the activity of C3a or C3b) is one or more of an antibody, an inhibitory nucleic acid, a non-antibody binding polypeptide, or a small molecule chemical compound. In some embodiments, the inhibitory nucleic acid is selected from the group consisting of an antisense oligonucleotide, an siRNA, a microRNA (miR), or a ribozyme. In some embodiments, the therapeutic is an antibody or functional fragment thereof. In some embodiments, the antibody is a monoclonal antibody or a polyclonal antibody. In some embodiments, the antibody is selected from the group consisting of human antibodies, humanized antibodies, camelised antibodies, chimeric antibodies, CDR-grafted antibodies, single-chain Fvs (scFv), disulfide-linked Fvs (sdFv), Fab fragments, and F(ab') fragments. In some embodiments, the individual is administered about 50 mg/kg of an antibody (e.g., an anti-C5 antibody or an anti-C3b antibody). In some embodiments, the individual is administered an antibody three times a week. In some embodiments, the individual is administered an antibody (e.g., an anti-C5 antibody or an anti-C3b antibody) for about 9 weeks.

In a further aspect, disclosed herein is a therapeutic for use in the treatment of a complement-related nephropathy or liver fibrosis. The therapeutic includes, for example, an agent that inhibits the expression or activity of C5, an agent that inhibits the expression or activity of C3, and an agent that inhibits the activity of the proteolytic cleavage products of C3 (C3a or C3b). In some embodiments, the therapeutic is an anti-C5 antibody. In some embodiments, the therapeutic is an anti-C3b antibody. In some embodiments, the use of the therapeutic in the treatment improves kidney function (e.g., as evidenced by decreased blood urea nitrogen (BUN) concentration, decreased serum cystatin C concentration, and/or decreased urinary C5a concentration, or a combination thereof), as compared to treatment without the use of the therapeutic. In some embodiments, the use of the therapeutic in the treatment decreases glomerular MAC formation, as compared to treatment without the use of the therapeutic. In some embodiments, the use of the therapeutic in the treatment decreases immune cell infiltration in the kidneys, as compared to treatment without the use of the therapeutic. In some embodiments, the use of the therapeutic in the treatment decreases glomerular size and/or mesangial matrix expansion in the kidneys, as compared to treatment without the use of the therapeutic.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 18 depicts a table showing the top enriched gene expression pathways in the livers of MAID 6149 and MAID 6156 homozygous mice.

FIG. 19 depicts a table showing fibrosis gene signatures upregulated (highlighted in yellow) or downregulated (highlighted in blue) in the livers of MAID 6156 homozygous mice. Changes that did not reach statistical significance have been identified by "–".

FIG. 21B depicts nephrotoxicity gene expression changes in humanized C3 (huC3) mice compared to wild-type (WT) mice. FIG. 21C depicts extra-cellular matrix gene expression changes in humanized C3 (huC3) mice compared to wild-type (WT) mice. FIG. 21D depicts cytokine gene expression changes in humanized C3 (huC3) mice compared to wild-type (WT) mice. FIG. 21E depicts chemokine gene expression changes in humanized C3 (huC3) mice compared to wild-type (WT) mice. In FIGS. 21B-21E, the numbers with yellow highlight represent updated expression; the numbers with blue highlight represent downregulated expression; and the cells left empty represent changes that did not reach statistical significance.

FIG. 24A shows blood urea nitrogen (BUN) while FIG. 24B shows serum cystatin C concentrations.

FIG. 29A shows anti-C5 antibody treatment reversed disease signature genes in humanized C3 mice. FIG. 29B shows that rescued disease signature included immune, extracellular matrix, cytokine, complement and metabolism related genes. FIG. 29C shows that immune cell type markers that were upregulated in humanized C3 mice were shown to be subsequently attenuated by anti-C5 antibody treatment.

FIG. 31A shows that anti-C3b blocking antibody improved survival of humanized C3 mice. FIGS. 31B-31C show that anti-C3b blocking antibody also improved body weight in the humanized C3 mice.

DETAILED DESCRIPTION

Figure 1A:
FIG. 1A provides an illustration, not to scale, of the mouse (mC3) and humanized (hC3) C3 genomic loci. The mouse C3 gene spanning the 5' regulatory elements and the coding region from exon 1 through exon 41 are deleted and replaced by the 5' regulatory elements and the coding region from exon 1 through exon 41 of the human C3 gene and a loxP site, as indicated by a bold line and an arrow, respectively.
Figure 1A:

The complement system is an essential component of the innate immune system and plays a critical role as a defense mechanism against invading pathogens, primes adaptive immune responses, and helps remove immune complexes and apoptotic cells. While the complement system plays a critical role in many protective immune functions, complement activation is a significant mediator of tissue damage in a wide range of autoimmune and inflammatory disease processes, including complement-related nephropathies.

This disclosure provides, inter alia, non-human animals that express human or humanized C3 proteins in serum. Surprisingly, the inventors have discovered that rodents homozygous for a human or humanized C3 gene are prone to high rates of spontaneous death and additionally exhibit physiological, morphological, and histological symptoms which closely resemble complement-related nephropathies characterized by pathological C3 protein accumulation in the kidney, such as, for example, C3 glomerulopathy. As such, the non-human animals described herein are believed to represent the first model organism capable of replicating the symptoms of complement-related nephropathies observed in humans and can be used to evaluate the therapeutic effectiveness of candidate compounds or agents for treatment of these disorders. Further, the inventors have also discovered that these rodents display symptoms consistent with liver fibrosis. Accordingly, this disclosure provides methods for using non-human animals comprising nucleic acid sequences encoding a human or humanized C3 protein to assess the in vivo therapeutic efficacy of agents for use in treating a complement-related nephropathy and/or liver fibrosis.

I. Definitions

The term "complement-related nephropathy" or "complement-related nephrosis" as used herein refers to damage to or disease or disorder of the kidney, including diseases/disorders associated with undesired alternative complement pathway activation and/or deposition of complement activation products, such as, but not limited to, C3 and/or the C5b-9 membrane attack complex in kidney tissue, particularly the nephron and, more particularly, the glomerulus. In some embodiments, complement-related nephropathy includes one or more of the conditions known as atypical hemolytic uremic syndrome (aHUS) and/or C3 glomerulopathy (C3G), a form of membranoproliferative glomerulonephritis that encompass dense deposit disease (DDD) and C3 glomerulonephritis (C3GN).

As used herein, the term "rodent" refers to any member of the taxonomical order Rodentia. Examples of rodents include, without limitation, mice, rats, squirrels, prairie dogs, porcupines, beavers, guinea pigs, and hamsters. In one embodiment, a rodent is a rat. In another embodiment, a rodent is a mouse.

An "individual" or "subject" can be a vertebrate, a mammal, or a human. Mammals include, but are not limited to, farm animals (such as cows), sport animals, pets, primates, mice and rats. Individuals also include companion animals including, but not limited to, dogs and cats. In one aspect, an individual is a human.

An "effective amount" refers to an amount of therapeutic compound, such as a therapy for complement-related nephropathy, administered to an individual, either as a single dose or as part of a series of doses, which is effective to produce a desired therapeutic or prophylactic result.

A "therapeutically effective amount" or a "clinically effective amount" is at least the minimum concentration required to show a measurable improvement of a particular disorder. A therapeutically effective amount herein may vary according to factors such as the disease state, age, sex, and weight of the patient, and the ability of the therapeutic to elicit a desired response in the individual. A therapeutically effective amount may also be one in which any toxic or detrimental effects of the therapeutic are outweighed by the therapeutically beneficial effects. In the case of a complement-related nephropathy, the therapeutically effective amount may increase or improve overall kidney function, prevent kidney cell death, or improve or prevent damage to kidney cells, glomeruli, or associated components of the same.

II. Complement-Related Nephropathies

A. C3 and the Complement System

Complement, an essential component of the immune system, consists of more than 30 circulatory and cellular proteins that are involved in three linked biochemical cascades: the classical, lectin, and the alternative pathways. Complement functions to assist the immune system to destroy invading microorganisms as well as to maintain tissue homeostasis. C3 deficiency in humans is associated with increased susceptibility to bacterial infections. However, excessive or unregulated activation of complement contributes to tissue damage and is associated with a variety of variety of human diseases, disorders, and conditions characterized by abnormal complement activation.

The C3 gene encodes the serum complement protein C3, which plays a central role in the activation of the classical, lectin and alternative complement activation pathways. The human C3 gene is located on chromosome 19 at 19p13.3-p13.2. The human C3 gene has 41 exons and encodes a precursor polypeptide of 1663 amino acids, including a 22 amino acid signal peptide, a 645 amino acid β-chain and a 992 amino acid α-chain. During complement activation the α-chain is cleaved, thereby generating 9 different peptides, including the 77 amino acid C3a protein, which is a potent pro-inflammatory anaphylatoxin.

The C3 gene is conserved between several species, including primates, e.g., chimpanzee, Rhesus monkey, other mammals, e.g., dog, cow, rodent, e.g., mouse, chicken, zebrafish and frog. The mouse C3 gene is located on chromosome 17 at 17 29.72 cM19. The mouse C3 gene has 41 exons and encodes a precursor polypeptide of 1663 amino acids, including a 24 amino acid signal peptide, a 642 amino acid β chain and a 993 amino acid α chain. Similar to humans, complement activation in the mouse results in α-chain cleavage, thereby generating 9 different peptides, including a 78 amino acid C3a, which is a potent pro-inflammatory anaphylatoxin. C3 knockout mice have been generated following standard procedures known in the art (see, e.g., Drouin et al. (2001) Cutting edge: the absence of 3 demonstrates a role for complement in Th2 effector functions in a murine model of pulmonary allergy, *J Immunology* 167:4141-4144).

B. Kidney-Specific, C3-Mediated, Complement-Related Diseases

Several complement-related nephropathies are known to involve abnormally high levels of C3 deposition in the kidney, particularly in the glomerulus of the nephron.

1. Atypical HUS

Hemolytic-uremic syndrome (or haemolytic-uraemic syndrome), abbreviated HUS, is a disease characterized by hemolytic anemia (anemia caused by destruction of red blood cells), acute kidney failure (uremia), and a low platelet count (thrombocytopenia). It predominantly, but not exclusively, affects children. Most cases are preceded by an episode of infectious, sometimes bloody, diarrhea acquired as a foodborne illness or from a contaminated water supply caused by *E. coli* O157:H7, other non-o157:H7 *E. coli* serotypes, *Shigella*, and *Campylobacter*.

Despite the use of supportive care, an estimated 33-40% of patients will die or have end-stage renal disease (ESRD) with the first clinical manifestation of aHUS, and 65% of patients will die, require dialysis, or have permanent renal damage within the first year after diagnosis despite plasma exchange or plasma infusion (PE/PI) therapy. Patients who survive the presenting signs and symptoms of aHUS endure a chronic thrombotic and inflammatory state, which puts them at lifelong elevated risk of sudden blood clotting, kidney failure, and other severe complications including premature death.

2. DDD, C3 Glomerulonephritis, and C3 Glomerulopathy

Dense deposit disease (DDD) is a rare disorder characterized by the accumulation of large amounts of C3 in the renal glomeruli. The condition was named for the very dense deposits overserved in the glomerular basement membrane (GBM) using transmission electron microscopy. In 2013, as a result of a consensus meeting, scientists recommended that DDD be sub-grouped under a new heading: "C3 glomerulopathy" (C3G; Pickering et al., *Kidney Intl.*, 2013, 84:1079-89). This new term was brought about by the appreciation that there is another group of patients that exhibit glomerular disease with kidney biopsies reminiscent of DDD. In these individuals, the C3 deposits are lighter in color and more widespread in location when viewed using electron microscope. However, upon immunofluorescent evaluation, and similar to patients with DDD, there is a large amount of C3 in the renal glomeruli. Consequently, these patients are now diagnosed with "C3 glomerulonephritis" or "C3GN." In recognition of their symptomatic similarities, both DDD and C3GN are now classified as sub-types of C3G.

III. Creation of Humanized C3 Non-Human Animals

The humanized C3 animals used in the methods disclosed herein can be generated using methodologies known in the art (see, generally, "Gene Targeting: A Practical Approach," Joyner, ed., Oxford University Press, Inc. (2000)). In one embodiment, generation of the mice may optionally involve disruption of murine C3 gene and introduction of the gene encoding human or humanized C3 into the murine genome. In one embodiment, the introduction of the gene encoding human or humanized C3 is at the same location as the endogenous murine C3 gene.

The genetically modified non-human animals (humanized C3 animals) used in the methods disclosed herein can be produced by introducing transgenes into the germline of the animal. Embryonic target cells at various developmental stages can be used to introduce transgenes. Different methods are used depending on the stage of development of the embryonic target cell. The specific line(s) of any animal used in the present methods are selected for general good health, good embryo yields, good pronuclear visibility in the embryo, and good reproductive fitness. When genetically modified mice are to be produced, strains such as C57BL/6 or C57BL/6×DBA/2 F1, or FVB lines are often used (obtained commercially from Charles River Labs, Boston, Mass., The Jackson Laboratory, Bar Harbor, Me., or Taconic Labs.).

Introduction of the transgene into the embryo can be accomplished by any means known in the art such as, for example, microinjection, electroporation, or lipofection. For example, the transgene(s) can be introduced into a mammal by microinjection of the construct into the pronuclei of the fertilized mammalian egg(s) to cause one or more copies of the construct to be retained in the cells of the developing mammal(s). Following introduction of the transgene construct into the fertilized egg, the egg may be incubated in vitro for varying amounts of time, or reimplanted into the surrogate host, or both. In vitro incubation to maturity is within the scope of this disclosure. One common method is to incubate the embryos in vitro for about 1-7 days, depending on the species, and then reimplant them into the surrogate host.

Reimplantation is accomplished using standard methods. Usually, the surrogate host is anesthetized, and the embryos are inserted into the oviduct. The number of embryos implanted into a particular host will vary by species, but will usually be comparable to the number of off spring the species naturally produces.

Retroviral infection can also be used to introduce transgene into a non-human animal. The developing non-human embryo can be cultured in vitro to the blastocyst stage. During this time, the blastomeres can be targets for retroviral infection (Jaenich, R. (1976) *PNAS* 73:1260-1264). Efficient infection of the blastomeres is obtained by enzymatic treatment to remove the zona pellucida (Manipulating the Mouse Embryo, Hogan eds. (Cold Spring Harbor Laboratory Press, Cold Spring Harbor, 1986). The viral vector system used to introduce the transgene is typically a replication-defective retrovirus carrying the transgene (Jahner et al. (1985) *PNAS* 82:6927-6931; Van der Putten et al. (1985) *PNAS* 82:6148-6152).

A third type of target cell for transgene introduction is the embryonic stem (ES) cell. Transgenes can be efficiently introduced into the ES cells by DNA transfection or by retrovirus-mediated transduction. Such transformed ES cells can thereafter be combined with blastocysts from a non-human animal. The ES cells thereafter colonize the embryo and contribute to the germ line of the resulting chimeric animal.

Genetically modified animals comprising humanized C3 can be crossed with other animals. A manner of preparation is to generate a series of mammals, each containing one of the desired constructs or transgenes. Such mammals are bred together through a series of crosses, backcrosses and selections, to ultimately generate a single mammal containing all desired constructs and/or transgenes, where the mammal is otherwise congenic (genetically identical) to the wild type except for the presence of the desired constructs and/or transgene(s). In one embodiment, a mouse comprising a human or humanized C3 gene is produced in this manner.

Typically, crossing and backcrossing is accomplished by mating siblings or a parental strain with an offspring, depending on the goal of each particular step in the breeding process. In certain cases, it may be necessary to generate a large number of offspring in order to generate a single offspring that contains each of the knockout constructs and/or transgenes in the proper chromosomal location. In addition, it may be necessary to cross or backcross over several generations to ultimately obtain the desired genotype.

In one aspect, genetically modified rodents, e.g., a mouse or rat, are provided that express a human or humanized C3 protein, wherein the rodent that expresses a human or humanized C3 protein comprises a normal complement system, i.e., the levels of complement proteins in the blood, plasma or serum of the rodent expressing human or humanized C3 protein are similar to the levels of complement proteins in the blood, plasma or serum of a rodent that expresses functional endogenous C3 protein. In one embodiment, the rodent is a mouse. In one embodiment, the rodent is a rat.

In one aspect, a pluripotent or totipotent non-human animal, e.g., rodent, e.g., mouse or rat, cell comprising a genetic modification as described herein is provided. In one embodiment, the cell is a rodent cell. In one embodiment, the cell is a mouse cell. In one embodiment, the cell is a rodent ES cell. In one embodiment, the cell is a mouse ES cell.

In one aspect, a non-human animal, e.g., rodent, e.g., mouse or rat, egg is provided, wherein the non-human animal egg comprises an ectopic non-human animal chromosome, wherein the ectopic non-human animal chromosome comprises a genetic modification as described herein. In one embodiment, the non-human animal is a rodent. In one embodiment, the rodent is a mouse. In one embodiment, the rodent is a rat.

In one aspect, the mouse embryo, egg, or cell that is genetically modified to comprise a human C3 gene is of a mouse that is of a C57BL strain selected from C57BL/A, C57BL/An, C57BL/GrFa, C57BL/KaLwN, C57BL/6, C57BL/6J, C57BU6ByJ, C57BL/6NJ, C57BL/10, C57BL/10ScSn, C57BL/10Cr, and C57BL/Ola. In another embodiment, the mouse is a 129 strain selected from the group consisting of a strain that is 129P1, 129P2, 129P3, 129X1, 129S1 (e.g., 129S1/SV, 129S1/Svlm), 129S2, 129S4, 129S5, 129S9/SvEvH, 129S6 (129/SvEvTac), 129S7, 129S8, 129T1, 129T2 (see, e.g., Festing et al. (1999) Revised nomenclature for strain 129 mice, Mammalian Genome 10:836, see also, Auerbach et al (2000) Establishment and Chimera Analysis of 129/SvEv- and C57BL/6-Derived Mouse Embryonic Stem Cell Lines). In a specific embodiment, the genetically modified mouse is a mix of an aforementioned 129 strain and an aforementioned C57BL/6 strain. In another specific embodiment, the mouse is a mix of aforementioned 129 strains, or a mix of aforementioned BL/6 strains. In a specific embodiment, the 129 strain of the mix is a 129S6 (129/SvEvTac) strain. In another embodiment, the mouse is a BALB strain, e.g., BALB/c strain. In yet another embodiment, the mouse is a mix of a BALB strain and another aforementioned strain. In one embodiment, the mouse is Swiss or Swiss Webster mouse.

Further information regarding humanized C3 rodents and methods for making the same can be found in U.S. Patent Application Publication No. 20150313194, the disclosure of which is incorporated by reference herein.

As such, provided herein are genetically modified rodents, e.g., a mouse or rat, that express C3 protein from a humanized C3 gene, wherein the rodent expresses human or humanized C3 protein in its serum. In one embodiment, the rodent is a mouse. In one embodiment, the rodent is a rat. The serum of the rodent that expresses a human or humanized C3 protein can have approximately the same level of C3 protein as a rodent that expresses a functional, endogenous C3 protein, e.g., a wild-type mouse or rat. In one embodiment, the mouse expresses human or humanized C3 protein (hC3) in serum at a concentration of at least about 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, 90%, 100%, 110%, 120%, 130%, 140%, 150%, 160%, 170%, 180%, 190% or 200% of the level of C3 protein present in the serum of an age-matched mouse that expresses functional endogenous C3 protein, but does not comprise a replacement of an endogenous C3 gene, at an endogenous mouse C3 locus, with a human C3 gene or a fragment thereof.

In one embodiment, the rodent expresses human C3 protein in serum at a concentration of between about 1% and about 5%, between about 3% and about 7%, between about 5% and about 15%, between about 10% and about 20%, between about 10% and about 200%, between about 20% and about 150%, or between about 30% and about 100% of the level of mouse C3 protein present in the serum of an age-matched mouse that expresses functional endogenous C3 protein, but does not comprise a replacement of an endogenous C3 gene, at an endogenous mouse C3 locus, with a human C3 gene or a fragment thereof.

In one embodiment, the rodent expresses human or humanized C3 protein in serum at a concentration of between about 1 µg/ml and about 5 µg/ml, between about 3 µg/ml and about 7 µg/ml, between about 5 µg/ml and about 15 µg/ml, between about 10 µg/ml and about 20 µg/ml, between about 15 µg/ml and about 30 µg/ml, between about 20 µg/ml and about 40 µg/ml, between about 30 µg/ml and about 60 µg/ml, between about 50 µg/ml and about 100 µg/ml, between about 75 µg/ml and about 125 µg/ml between about 100 µg/ml and about 1500 µg/ml, between about 100 µg/ml and about 1500 µg/ml, between about 200 µg/ml and about 1250 µg/ml, or between about 300 µg/ml and about 1000 µg/ml. In another embodiment, the mouse expresses human or humanized C3 protein in serum at a concentration of at least about 1 µg/ml, 2 µg/ml, 3 µg/ml, 4 µg/ml, 5 µg/ml, 6 µg/ml, 7 µg/ml, 8 µg/ml, 9 µg/ml, 10 µg/ml, 11 µg/ml, 12 µg/ml, 13 µg/ml, 14 µg/ml, 15 µg/ml, 16 µg/ml, 17 µg/ml, 18 µg/ml, 19 µg/ml, 20 µg/ml, 30 µg/ml, 40 µg/ml, 50 µg/ml, 60 µg/ml, 70 µg/ml, 80 µg/ml, 90 µg/ml, 100 µg/ml, 200 µg/ml, 300 µg/ml, 400 µg/ml, 500 µg/ml, 600 µg/ml, 700 µg/ml, 800 µg/ml, 900 µg/ml, 1000 µg/ml, 1250 µg/ml or 1500 µg/ml, inclusive of values and ranges falling in between these concentrations.

IV. Use of Humanized C3 Non-Human Animals for Identifying or Assessing in Vivo Therapeutic Efficacy of Agents Capable of Treating Complement-Related Nephropathies A. Identifying Agents that Ameliorate Complement-Related Nephropathy or Liver Fibrosis In some aspects, provided herein are methods for 1) identifying a candidate agent (i.e. a compound or therapeutic molecule) or 2) assessing the in vivo therapeutic efficacy of a candidate agent for use in the treatment of a complement-related nephropathy, such as, without limitation aHUS, DDD, C3 glomerulonephritis, and/or C3 glomerulopathy. The method utilizes any of the humanized C3 non-human animals (for example, mice or rats) disclosed herein. In some embodiments, candidate compounds are administered directly to non-human animals exhibiting symptoms of a complement-related nephropathy to determine if the agent or compound can reduce one or more symptoms of the complement-related nephropathy and/or liver fibrosis. In other embodiments, candidate compounds are contacted with serum obtained from these non-human animals and complement activity is assessed using any commonly used in vitro assessment technique (such as, but not limited to CH50 assays).

In some embodiments, the candidate compound or agent can modulate complement activation by reducing, decreasing, or inhibiting complement activation (such as, but not limited to alternative pathway complement activation and/or C3-mediated complement pathway activation) or C3 protein cleavage and/or deposition in the kidneys or livers of the humanized C3 non-human animals (such as rodents, for example, mice or rats) described herein. The compound or agent may reduce complement activation or C3 protein cleavage and/or deposition in any of the non-human animals disclosed herein by any of about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent.

In another embodiment, the candidate compound can reduce, decrease, or inhibit complement activation (such as, but not limited to, alternative pathway complement activation or C3-mediated complement pathway activation) or C3 protein cleavage and/or deposition in the kidneys or livers of any of the humanized C3 non-human animals (such as rodents, for example, mice or rats) described herein for up to 1 hour, 2 hours, 3 hours, 4 hours, 5 hours, 6 hours, 7 hours, 8 hours, 9 hours, 10, hours, 11, hours, 12 hours, 18 hours, 24 hours, 30 hours, 36 hours, 42 hours, 48 hours, 54 hours, 60 hours, 66 hours, 72 hours, 4 days, 5 days, 6 days, 7 days, 8 days, 9 days, 10 days, 11 days, 12 days, 13 days, 14 days, or three weeks, (including any periods of time in between these values).

The candidate compound can further modulate complement activation in other embodiments by increasing, amplifying or activating complement activity (such as, but not limited to, alternative pathway complement activity or C3-mediated complement pathway activity) in the kidneys or livers of any of the humanized C3 non-human animals (such as rodents, for example, mice or rats) described herein. The compound may increase complement activity in any of the rodents disclosed herein by any of 100/o, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent.

In another embodiment, the candidate compound can increase, amplify or activate complement activity (such as, but not limited to, alternative pathway complement activity or C3-mediated complement pathway activity) in the kidneys or livers of any of the humanized C3 non-human animals (such as rodents, for example, mice or rats) described herein for up to 1 hour, 2 hours, 3 hours, 4 hours, 5 hours, 6 hours, 7 hours, 8 hours, 9 hours, 10, hours, 11, hours, 12 hours, 18 hours, 24 hours, 30 hours, 36 hours, 42 hours, 48 hours, 54 hours, 60 hours, 66 hours, 72 hours, 4 days, 5 days, 6 days, 7 days, 8 days, 9 days, 10 days, 11 days, 12 days, 13 days, 14 days, or three weeks, (including any periods of time in between these values).

In other embodiments, the candidate agent or compound ameliorates or treats one or more symptoms of a complement-related nephropathy or liver fibrosis in a non-human animal (such as a rodent, for example a mouse or a rat) compared to a control non-human animal who has not been administered the candidate agent or compound. The terms "ameliorate" or "treat," as used herein, unless otherwise specified, means to eliminate, delay the onset of, or reduce the prevalence, frequency, or severity of one or more symptoms associated with a complement-related nephropathy (such as, without limitation aHUS, DDD, C3 glomerulonephritis, and/or C3 glomerulopathy) or liver fibrosis.

The one or more symptoms of complement-related nephropathy (such as, without limitation aHUS, DDD, C3 glomerulonephritis, and/or C3 glomerulopathy) can in some embodiments be spontaneous death. As such, the candidate compound or agent can ameliorate the occurrence of spontaneous death in any of the humanized C3 non-human animals (such as rodents, for example, mice or rats) described herein by any of 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent.

As shown in Example 2 below, the homozygotic humanized C3 rodents described herein exhibit decreased weight (i.e. the inability to gain weight normally), decreased bone density and/or mineral content, and/or decreased body fat relative to wildtype littermates or rodents that do not express a human or humanized C3 protein. Accordingly, in some embodiments, the one or more symptoms of complement-related nephropathy (such as, without limitation aHUS, DDD, C3 glomerulonephritis, and/or C3 glomerulopathy) ameliorated by the candidate agent or compound is one or more of decreased weight, decreased bone density, or decreased body fat. As such, the candidate compound or agent can ameliorate one or more of low body weight, decreased bone density or mineral content, and/or decreased body fat in any of the humanized C3 non-human animals (such as mice or rats) described herein by any of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent. Determination of weight loss or gain, bone density or mineral content, and body fat is routine and can be accomplished according to methods that are well known in the art.

Additionally, as described in Example 4 below, the homozygotic humanized C3 rodents described herein exhibit high levels of C3 protein deposition in the kidney, particularly in the nephron (for example, in the glomerulus) relative to wildtype littermates or rodents that do not express a human or humanized C3 protein. Accordingly, in some embodiments, the one or more symptoms of complement-related nephropathy (such as, without limitation aHUS, DDD, C3 glomerulonephritis, and/or C3 glomerulopathy) ameliorated by the candidate agent or compound is C3 protein deposition in the kidney. As such, the candidate compound or agent can ameliorate kidney C3 protein deposition in any of the humanized C3 non-human animals (such as mice or rats) described herein by any of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent. Determination of kidney C3 protein deposition can be analyzed by any number of means known in the art, including, but not limited to, immunohistochemistry, immunofluorescence, and electron microscopy (including immunoelectron microscopy).

Example 4 also showed increased C5b-9 membrane attack complex deposition in the kidney glomerulus of humanized C3 rodents relative to wildtype littermates or rodents that do not express a human or humanized C3 protein, which is indicative of an activated complement pathway. Accordingly, in some embodiments, the one or more symptoms of complement-related nephropathy (such as, without limitation aHUS, DDD, C3 glomerulonephritis, and/or C3 glomerulopathy) ameliorated by the candidate agent or compound is increased formation of the C5b-9 membrane attack complex. As such, the candidate compound or agent can ameliorate formation of the C5b-9 membrane attack complex in any of the humanized C3 non-human animals (such as mice or rats) described herein by any of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent. C5b-9 membrane attack complex formation can be determined by any number of means known in the art, including, but not limited to, immunohistochemistry, immunofluorescence (such as an immunofluorescently labeled anti-C9 antibody), and electron microscopy (including immunoelectron microscopy).

As shown in Example 3, the homozygotic humanized C3 rodents described herein exhibit elevated levels of serum and/or plasma blood urea nitrogen (BUN), lipase, cystatin, and non-high density lipoproteins relative to wildtype littermates or rodents that do not express a human or humanized C3 protein. Accordingly, in some embodiments, the one or more symptoms of complement-related nephropathy (such as, without limitation aHUS, DDD, C3 glomerulonephritis, and/or C3 glomerulopathy) ameliorated by the candidate agent or compound is elevated levels of serum and/or plasma BUN, lipase, cystatin, and non-high density lipoproteins. As such, the candidate compound or agent can ameliorate elevated levels of serum and/or plasma BUN, lipase, cystatin, and non-high density lipoproteins in any of the humanized C3 non-human animals (such as mice or rats) described herein by any of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent. Assessing serum and/or plasma levels of BUN, lipase, cystatin, and non-high density lipoproteins can be accomplished using any number of methods which are well known in the art.

Example 3 further shows that the homozygotic humanized C3 rodents described herein exhibit elevated urinary albumin concentrations relative to wildtype littermates or rodents that do not express a human or humanized C3 protein. Example 4 shows that the homozygotic humanized C3 rodents described herein exhibit elevated urinary C5a levels relative to wildtype littermates or rodents that do not express a human or humanized C3 protein. Accordingly, in some embodiments, the one or more symptoms of complement-related nephropathy (such as, without limitation aHUS, DDD, C3 glomerulonephritis, and/or C3 glomerulopathy) ameliorated by the candidate agent or compound is increased urinary albumin and/or C5a. As such, the candidate compound or agent can ameliorate elevated levels of urinary albumin and/or C5a in any of the humanized C3 non-human animals (such as mice or rats) described herein by any of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 569%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent. Assessing urinary albumin levels can be accomplished using any number of methods which are well known in the art.

The homozygotic humanized C3 rodents described herein further exhibit symptoms consistent with liver injury or fibrosis. Fibrosis is the formation of excess fibrous connective tissue in an organ or tissue in a reparative or reactive process. Physiologically, fibrosis acts to deposit connective tissue, which can obliterate the architecture and function of the underlying organ or tissue. Defined by the pathological accumulation of extracellular matrix (ECM) proteins, fibrosis results in scarring and thickening of the affected tissue, it is in essence an exaggerated wound healing response which interferes with normal organ function. Fibrosis of the liver is often called cirrhosis and can be caused by a number of conditions such as alcoholic liver disease (ALD), nonalcoholic steatohepatitis (NASH), chronic hepatitis C, chronic hepatitis B, primary sclerosing cholangitis, autoimmune hepatitis, hereditary hemochromatosis, Wilson's disease, alpha 1-antitrypsin deficiency, galactosemia, glycogen storage disease type IV, cystic fibrosis, or exposure to Hepatotoxic drugs or toxins, among many others.

Example 3 further shows that the homozygotic humanized C3 rodents described herein exhibit elevated levels of the liver enzymes alanine aminotransferase (ALT), aspartate aminotransferase (AST), or alkaline phosphatase (ALP). Accordingly, in some embodiments, the one or more symptoms of liver fibrosis ameliorated by the candidate agent or compound is elevated levels of ALT, AST, or ALP. As such, the candidate compound or agent can ameliorate elevated levels of ALT, AST, and/or ALP in any of the humanized C3 non-human animals (such as mice or rats) described herein by any of 10%, 11%, 120%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 990%, or 100% in comparison to control non-human animals that are not treated with the candidate compound or agent. Assessing ALT, AST, or ALP liver enzyme levels can be accomplished using any number of methods which are well known in the art.

In some embodiments, the one or more symptoms of complement-related nephropathy or liver fibrosis are reflected by a disease gene signature, i.e., a gene signature characteristic of the disease, i.e., complement-related nephropathy or liver fibrosis. The disease gene signature includes a set of genes that are differentially expressed in a subject (e.g., a rodent) having the disease as compared to wildtype control subjects without the disease. By "differentially expressed" it is meant that the expression of a signature gene is increased or decreased, as compared to the expression of the signature gene in a wildtype control without the disease, by at least 20%, 25%, 30%, 35%, 40%, 45%, 50%, 55%, 60%, 65%, 70%, 75%, 80%, 85%, 90%, 95%, 100%, or greater. In some embodiments, the gene signature for complement-related liver fibrosis includes one or more of the genes listed in FIG. 17, or one or more of the differentially expressed genes in FIG. 19. In some embodiments, the gene signature for complement-related nephropathy includes one or more of the nephrotoxicity genes listed in FIG. 21B, one or more of the extracellular matrix (ECM) genes listed in FIG. 21C, one or more of the cytokine genes listed in FIG. 21D, one or more of the chemokine genes listed in FIG. 21E, or a combination thereof. In some embodiments, the gene signature for complement-related nephropathy and for liver fibrosis includes one or more the genes listed in FIG. 29C, e.g., one or more of ECM genes selected from the group consisting of Timp1, Spp1, Col13a1, Mmp14, Tgfbi, Mmp2, Col1a1, and Tnc; one or more of cytokine and receptor genes selected from the group consisting of Ccl22, Ccr1, Tnfsf8, Il1f6, Ccl5, Il1rn, Tlr1, Itgb2, Ccr2, C3ar1, and Fos; one or of the immune signaling molecules selected from the group consisting of Btla, Cd86, Cd3e, Icos, H2-Abl, Cd14, Cd28, H2-Eb1, Tyrobp, Tlr8, Cd200r1, Itgam, Cd2, Cd84, Klrk1, C1qc, H2-Oa, and H2-Aa; one or more of T-cell associated genes selected from the group consisting of Cd4, Cd3g, Lcp2, H2-Oa, H2-Aa, Cd247, Ptprc, and Lck; one or more of complement and coagulation genes selected from the group consisting of C5ar1, Cfi, C3ar1, C6, C1qc, C7, C1qa, C1qb, Serpine1, F13a1, and Cfh; one or more of lipid metabolism genes selected from the group consisting of Cyp7b1, Akr1c188, Agps, and Lpl. In some embodiments, the gene signature for complement-related nephropathy and for liver fibrosis includes one or more of immune cell type markers listed in FIG. 29B, e.g., markers selected from the group consisting of Ms4a1, Cd79a, Cd79b, Cd19, Cd3d, Cd3e, Cd3g, Cd8a, Cd8b1, Cd4, Foxp3, Prf1, Gzma, Kird1, Kirk1, Ncr1, Ccl22, Clec9a, Cd207, Adam23, Marco, Msr1, C1qb, Ms4a7, Cxcr2, Csf3r, Robo4, Tek, Tie1, Cdh5, Kdr, Esam, Tagln, Acta2, Fap, and Tnc.

In some embodiments, the one or more symptoms of complement-related nephropathy or liver fibrosis are assessed by determining the expression of one or more, e.g., multiple or a collection, of disease signature genes. A candidate compound can be assessed in its ability to ameliorate, i.e., reverse fully or partially, the elevated or decreased expression of disease signature genes, as illustrated in Example 7. For example, the candidate compound or agent can ameliorate elevated or decreased expression levels of one or more genes in the disease gene signature set in any of humanized C3 non-human animals (such as mice or rats) described herein by any of 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% in comparison to control non-human animals that are not treated with the candidate compound or agent.

B. Candidate Agents or Compounds

Candidate therapeutic agents or compounds can be, without limitation, small molecule chemical compounds, antibodies, proteins, inhibitory nucleic acids, or any combination thereof.

1. Antibodies

In some aspects, the candidate agent or compound binds (such as preferentially binds) to a complement protein (such as, but not limited to, C5, C3, or proteolytic products thereof (e.g. C3a or C3b)) and is an antibody. The terms "antibody" and "antibodies" refer to fully human antibodies, humanized antibodies, camelised antibodies, chimeric antibodies, CDR-grafted antibodies, single-chain Fvs (scFv), disulfide-linked Fvs (sdFv), Fab fragments, F(ab') fragments, and antigen-binding fragments of any of the foregoing. In particular, the antibodies include immunoglobulin molecules and antigen-binding active fragments of immunoglobulin molecules, i.e., molecules that contain an antigen binding site. Such fragments may or may not be fused to another immunoglobulin domain including, but not limited to, an Fc region or fragment thereof. The skilled person will appreciate that other fusion products may be generated, including but not limited to, scFv-Fc fusions, variable region (e.g., VL and VH)-Fc fusions, and scFv-scFv-Fc fusions. Immunoglobulin molecules can be of any type, including, IgG, IgE, IgM, IgD, IgA and IgY, and of any class, including IgG$_1$, IgG$_2$, IgG$_3$, IgG$_4$, IgA$_1$ and IgA$_2$), or of any subclass. In some embodiments, the antibodies are C5 and/or C3 antagonists and can decrease complement activation (such as alternative complement pathway activation, for example, in the kidney or the liver). In other embodiments, the antibodies are C5 and/or C3 agonists and can increase complement activation.

Variants of antibodies can also be made based on information known in the art, without substantially affecting the activity of antibody. For example, antibody variants can have at least one amino acid residue in the antibody molecule replaced by a different residue. For antibodies, the sites of greatest interest for substitutional mutagenesis generally include the hypervariable regions, but framework region (FR) alterations are also contemplated.

For antibodies, one type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Nucleic acid molecules encoding amino acid sequence variants of the antibody can be prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides, thereby generating a Fc region variant. The Fc region variant may comprise a human Fc region sequence (e.g. a human IgG1, IgG2, IgG3 or IgG4 Fc region) comprising an amino acid modification (e.g. a substitution) at one or more amino acid positions including that of a hinge cysteine.

Fc region variants with altered (improved or diminished) C1q binding and/or Complement Dependent Cytotoxicity (CDC) are described in International Patent Application Publication No.: WO99/51642 (incorporated herein by reference). Such variants may comprise an amino acid substitution at one or more of amino acid positions of the Fc region. See, also, Duncan & Winter, Nature 322:738-40 (1988); U.S. Pat. Nos. 5,648,260; 5,624,821; and International Patent Application Publication No.: WO94/29351 concerning Fc region variants, the disclosures of each of which are incorporated by reference herein.

2. Non-Antibody Binding Polypeptides

In some aspects, the candidate compound binds (such as preferentially binds) to a complement protein (such as, C5, C3, or proteolytic products thereof (e.g. C3a or C3b)) and is a non-antibody binding polypeptide. In some embodiments, the non-antibody binding polypeptide is a C5 and/or C3 antagonist and can decrease complement activation (such as alternative complement pathway activation, for example, in the kidney or the liver). In other embodiments, the non-antibody binding polypeptide is a C5 and/or C3 agonist and can increase complement activation.

Binding polypeptides may be chemically synthesized using known polypeptide synthesis methodology or may be prepared and purified using recombinant technology. Binding polypeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more, wherein such binding polypeptides that are capable of binding to a target, such as any of the complement proteins (e.g. C5, C3, C3a, or C3b) discussed herein.

Binding polypeptides may be identified without undue experimentation using well known techniques. In this regard, it is noted that techniques for screening polypeptide libraries for binding polypeptides that are capable of binding to a polypeptide target are well known in the art (see, e.g., U.S. Pat. Nos. 5,556,762, 5,750,373, 4,708,871, 4,833,092, 5,223,409, 5,403,484, 5,571.689, 5,663,143; PCT Application Publication Nos. WO 84/03506 and WO84/03564; Geysen et al, *Proc. Natl. Acad. Sci. U.S.A.,* 81:3998-4002 (1984); Geysen et al, *Proc. Natl. Acad. Sci. U.S.A.,* 82: 178-182 (1985); Geysen et al., *J. Immunol. Meth,* 102:259-274 (1987); Clackson, T. et al., (1991) *Nature,* 352: 624; Kang, A. S. et al., (1991) *Proc. Natl. Acad. Sci. USA,* 88:8363, and Smith, G. P. (1991) *Current Opin. Biotechnol,* 2:668, the disclosures of each of which are incorporated by reference herein.

Methods for generating peptide libraries and screening these libraries are also disclosed in U.S. Pat. Nos. 5,723,286, 5,432,018, 5,580,717, 5,427,908, 5,498,530, 5,770,434, 5,734,018, 5,698,426, 5,763,192, and 5,723,323, the disclosures of each of which are incorporated by reference herein.

Binding polypeptides can be modified to enhance their inhibitory and/or therapeutic effect (including, for example, enhanced affinity, improved pharmacokinetic properties such as half-life, stability, and clearance rate, reduced toxicity, etc.). Such modifications include, without limitation, glycosylation, pegylation, substitution with non-naturally occurring but functionally equivalent amino acid, linking groups, etc.

3. Small Molecule Chemical Compounds

In some aspects, the candidate compound binds (such as preferentially binds) to a complement protein (such as, C5, C3, or proteolytic products thereof (e.g. C3a or C3b)) and is a small molecule. In some embodiments, the small molecule is a C5 and/or C3 and can decrease complement activation (such as alternative complement pathway activation, for example, in the kidney or the liver). In other embodiments, the small molecule is a C5 and/or C3 agonist and can increase complement activation.

Small molecules are preferably organic molecules other than binding polypeptides or antibodies as defined herein. Organic small molecules may be identified and chemically synthesized using known methodology (see, e.g., PCT Application Publication Nos. WO 00/00823 and WO 00/39585). Organic small molecules are usually less than about 2000 Daltons in size, alternatively less than about 1500, 750, 500, 250 or 200 Daltons in size, wherein such organic small molecules that are capable of binding to a polypeptide as described herein may be identified without undue experimentation using well known techniques. In this regard, it is noted that techniques for screening organic small molecule libraries for molecules that are capable of binding to a polypeptide target are well known in the art (see, e.g., PCT Application Publication Nos. WO 00/00823 and WO 00/39585).

Organic small molecules may be, for example, aldehydes, ketones, oximes, hydrazones, semicarbazones, carbazides, primary amines, secondary amines, tertiary amines, N-substituted hydrazines, hydrazides, alcohols, ethers, thiols, thioethers, disulfides, carboxylic acids, esters, amides, ureas, carbamates, carbonates, ketals, thioketals, acetals, thioacetals, aryl halides, aryl sulfonates, alkyl halides, alkyl sulfonates, aromatic compounds, heterocyclic compounds, anilines, alkenes, alkynes, diols, amino alcohols, oxazolidines, oxazolines, thiazolidines, thiazolines, enamines, sulfonamides, epoxides, aziridines, isocyanates, sulfonyl chlorides, diazo compounds, acid chlorides, or the like.

In some aspects, the small molecule chemical compound is a component of a combinatorial chemical library. Combinatorial chemical libraries are a collection of multiple species of chemical compounds comprised of smaller subunits or monomers. Combinatorial libraries come in a variety of sizes, ranging from a few hundred to many hundreds of thousand different species of chemical compounds. There are also a variety of library types, including oligomeric and polymeric libraries comprised of compounds such as carbohydrates, oligonucleotides, and small organic molecules, etc. Such libraries have a variety of uses, such as immobilization and chromatographic separation of chemical compounds, as well as uses for identifying and characterizing ligands capable of binding a target molecule (for example, C5, C3, C3a or C3b) or mediating a biological activity of interest (such as, but not limited to, inhibition or activation of complement activity).

Various techniques for synthesizing libraries of compounds on solid-phase supports are known in the art. Solid-phase supports are typically polymeric objects with surfaces that are functionalized to bind with subunits or monomers to form the compounds of the library. Synthesis of one library typically involves a large number of solid-phase supports. To make a combinatorial library, solid-phase supports are reacted with one or more subunits of the compounds and with one or more numbers of reagents in a carefully controlled, predetermined sequence of chemical reactions. In other words, the library subunits are "grown" on the solid-phase supports. The larger the library, the greater the number of reactions required, complicating the task of keeping track of the chemical composition of the multiple species of compounds that make up the library. In some embodiments, the small molecules are less than about 2000 Daltons in size, alternatively less than about 1500, 750, 500, 250 or 200 Daltons in size.

The small molecule agents described in any of the aspects herein can be derived from any type of chemical reaction that can be carried out on a solid support. Such chemical reactions include, but are not limited to, 2+2 cycloadditions including trapping of butadiene; [2+3] cycloadditions including synthesis of isoxazolines, furans and modified peptides; acetal formation including immobilization of diols, aldehydes and ketones; aldol condensation including derivatization of aldehydes, synthesis of propanediols; benzoin condensation including derivatization of aldehydes; cyclocondensations including benzodiazepines and hydantoins, thiazolidines, turn mimetics, porphyrins, phthalocyanines; Dieckmann cyclization including cyclization of diesters; Des-Alder reaction including derivatization of acrylic acid; Electrophilic addition including addition of alcohols to alkenes; Grignard reaction including derivatization of aldehydes; Heck reaction including synthesis of disubstituted alkenes; Henry reaction including synthesis of nitrile oxides in situ (see 2+3 cycloaddition); catalytic hydrogenation including synthesis of pheromones and peptides (hydrogenation of alkenes); Michael reaction including synthesis of sulfanyl ketones, bicyclo[2.2.2]octanes; Mitsunobu reaction including synthesis of aryl ethers, peptidyl phosphonates and thioethers; nucleophilic aromatic substitutions including synthesis of quinolones; oxidation including synthesis of aldehydes and ketones; Pausen-Khand cycloaddition including cyclization of norbornadiene with pentynol; photochemical cyclization including synthesis of helicenes; reactions with organo-metallic compounds including derivatization of aldehydes and acyl chlorides; reduction with complex hydrides and tin compounds including reduction of carbonyl, carboxylic acids, esters and nitro groups; Soai reaction including reduction of carboxyl groups; Stille reactions including synthesis of biphenyl derivatives; Stork reaction including synthesis of substituted cyclohexanones; reductive amination including synthesis of quinolones; Suzuki reaction including synthesis of phenylacetic acid derivatives; and Wittig-Horner reactions including reactions of aldehydes, pheromones, and sulfanyl ketones.

References disclosing the synthesis of chemical libraries as well as the deconvolution of the individual compounds of those libraries onto individual solid phase supports, can be found in U.S. Patent Application No. 2009/0032592; Needels et al., (1993), *Proc. Natl. Acad. Sci. USA* 90:10700-10704; and PCT Application Publication No. WO 97/15390, the disclosures of which are incorporated by reference herein.

4. Inhibitory Nucleic Acids

In one aspect of this disclosure, the candidate complement modulatory compound is one or more oligonucleotides targeted to a component (such as an mRNA) of the complement system. The inhibitory nucleic acid can be, without limitation, any of an antisense oligonucleotide, a small inhibitory RNA (siRNA), or a ribozyme.

The oligonucleotide of this disclosure may be an mRNA encoding a protein component of the complement system. The oligonucleotides will bind to the mRNAs and interfere with their functions, either by mediating their destruction or by preventing translation into proteins. Absolute complementarity, although preferred, is not required. An oligonucleotide sequence "complementary" to a portion of an RNA, as referred to herein, means a sequence having sufficient complementarity to be able to hybridize with the RNA, forming a stable duplex. The ability to hybridize will depend on both the degree of complementarity and the length of the oligonucleotide. Generally, the longer the hybridizing nucleic acid, the more base mismatches with an RNA it may contain and still form a stable duplex. Those skilled in the art can ascertain a tolerable degree of mismatch by use of standard procedures to determine the melting point of the hybridized complex.

In general, complementary oligonucleotides manufactured to hybridize with mRNAs for proteins of the complement system are targeted to any region of the mRNA, including to the 5 untranslated region of the mRNA, to the complement of the AUG start codon, or to the 3' untranslated region.

The oligonucleotides can have alternate internucleoside linkages, such as, but not limited to, phosphorothioate (Mag at al., *Nucleic Acids Res.* 19:1437-1441, 1991; and U.S. Pat. No. 5,644,048), peptide nucleic acid or PNA (Egholm, *Nature,* 3685:566-568, 1993; and U.S. Pat. No. 6,656,687), phosphoramide (Beaucage, *Methods Mol. Biol.* 20:33-61, 1993), phosphorodithioate (Capaldi et al., *Nucleic Acids*

Res., 28:E40, 2000). Other oligonucleotide analogs include such as, but not limited to, morpholino (Summerton, *Biochim. Biophys. Acta.*, 1489:141-158, 1999), locked oligonucleotides (Wahlestedt wt al., *Proc. Natl. Acad. Sci. USA*, 97:5633-5638, 2000), peptidic nucleic adds or PNA (Nielsen et al., 1993; Hyrup and Nielsen, 1996) or 2-o-(2-methoxyl) ethyl modified 5' and 3' end oligonucleotides (McKay et al., *J. Biol. Chem.*, 274:1715-1722, 1999). All of these references are hereby expressly incorporated by reference. The nucleic acids may contain any combination of deoxyribo- and ribo-nucleotides, and any combination of bases, including uracil, adenine, thymine, cytosine, guanine, inosine, xathanine hypoxathanine, isocytosine, isoguanine, etc.

The complementary oligonucleotides according to this disclosure may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine. N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diaminopurin.

The complementary oligonucleotides may also comprise at least one modified sugar moiety selected from the group including but not limited to arabinose, 2-fluoroarabinose, xylulose, and hexose.

The complementary oligonucleotides should be at least ten nucleotides in length, and may range from 10 to about 50 nucleotides in length, such as 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length.

V. Treatment of Complement-Related Nephropathies

Additionally provided herein are methods for treating one or more complement related neuropathies (such as, without limitation, atypical hemolytic uremic syndrome (aHUS) or C3 glomerulopathy (C3G; such as dense deposit disease (DDD) or C3 glomerulonephritis (C3GN)). As illustrated in Examples 6-7, treatment of humanized C3 mice exhibiting one or more symptoms of complement related neuropathies with a clinically effective amount of a therapeutic that inhibits the expression or activity of C5 can result in improved survival and kidney function, decreased histological signs of kidney and glomerular damage associated with complement related neuropathies, and fully or partially reversed disease signature gene expression. In addition, as illustrated in Example 9, treatment of humanized C3 mice exhibiting one or more symptoms of complement related neuropathies with a clinically effective amount of a therapeutic that inhibits the expression of activity of C3, or the activity of its proteolytic cleavage products (C3a or C3b), can also result in improved survival.

As used herein, a "therapeutic that inhibits the expression or activity of C5" refers to any agent capable of inhibiting the biological function or activity of complement factor 5 (C5). This includes agents, substances, or compounds that prevent the C5 protein from functioning as it normally does in the complement pathway, prevent expression of the C5 gene, prevent processing of the C5 pre-RNA to a mature mRNA, prevent translation of the C5 mRNA to a C5 polypeptide, prevent posttranslational modification or processing of the C5 polypeptide necessary for its normal physiological functioning, and/or blocks or interferes with the activity of the C5 protein.

As used herein, a "therapeutic that inhibits the expression or activity of C3" refers to any agent capable of inhibiting the biological function or activity of complement factor 3 (C3). This includes agents, substances, or compounds that prevent the C3 protein from functioning as it normally does in the complement pathway, prevent expression of the C3 gene, prevent processing of the C3 pre-RNA to a mature mRNA, prevent translation of the C3 mRNA to a C3 polypeptide, prevent posttranslational modification or processing of the C3 polypeptide necessary for its normal physiological functioning, and/or blocks or interferes with the activity of the C3 protein.

A "therapeutic that inhibits the activity of C3a or C3b" refers to any agent capable of inhibiting the biological function or activity of C3a or C3b.

In some embodiments, the therapeutic is one or more of an inhibitory nucleic acid, a non-antibody binding polypeptide, or a small molecule chemical compound, such as any of the antibodies, inhibitory nucleic acids (such as, without limitation, an antisense oligonucleotide, an siRNA, a micro-RNA (miR), or a ribozyme) or non-antibody binding polypeptides discussed herein.

In other embodiments, the therapeutic is an antibody or functional fragment thereof (such as, without limitation, a monoclonal antibody a polyclonal antibody, a human antibody, a humanized antibody, a camelised antibody, a chimeric antibody, a CDR-grafted antibody, a single-chain Fv (scFv), a disulfide-linked Fv (sdFv), a Fab fragment, or a F(ab') fragment). The antibody can be administered to the individual daily, every other day, every three days, every four days, every five days, every six days, once a week, or once a fortnight. In some instances, about 40 mg/kg to about 60 mg/kg of the antibody can be administered to an individual diagnosed with or thought to have a complement-related nephropathy (such as any of about 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, or more). Antibody administration can be via any means known in the art, including, without limitation, injection, arterial delivery, insufflation, ingestion, or via suppository. Anti-C5 antibody therapy can continue for 8-56 weeks (such as any of about 8, 9, 10, 11, 12, 13, 14, 15, 16, 17, 18, 19, 20, 21, 22, 23, 24, 25, 26, 27, 28, 29, 30, 35, 40, 45, 50, 55, or 56 weeks), 1-5 years, or indefinitely. In some embodiments, anti-C5 antibodies appropriate for use in any of the therapeutic methods disclosed herein can be made using known methods, e.g., as described in U.S. patent application Ser. No. 15/621,689, the disclosure of which is incorporated by reference herein. In some embodiments, anti-C3, anti-C3a or anti-C3b antibodies appropriate for use in any of the therapeutic methods disclosed herein can be made using known methods.

Provided herein are methods for improving kidney function in an individual diagnosed with or thought to have a complement-related nephropathy. The method includes administering a clinically effective amount of a therapeutic, such as any of the therapeutics described above. Administration of the therapeutic results in improved kidney function relative to individuals diagnosed with a complement-related nephropathy who have not been administered the therapeutic. In some embodiments, improved kidney function can be shown by decreased blood urea nitrogen (BUN) levels. Specifically, administering a clinically effective amount of a therapeutic that inhibits the expression or activity of C5 to an individual diagnosed with or thought to have a complement-related nephropathy can result in about 10-50% decreased BUN levels (such as any of about 10%, 11%, 12%, 13%, 15%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49/O, or 50% decreased BUN levels) relative to the BUN levels in individuals diagnosed with a complement-related nephropathy that have not been administered a therapeutic that inhibits the expression or activity of C5. Measurement of BUN is routine in the art and can be performed by any known means.

In other embodiments, improved kidney function can be shown by decreased serum cystatin C concentration. For example, administration of a clinically effective amount of a therapeutic that inhibits the expression or activity of C5 to an individual diagnosed with or thought to have a complement-related nephropathy can result in about 10-60% decreased serum cystatin C concentration (such as any of about 10%, 11%, 12%, 13%, 15%, 15%, 16%, 17%, 18%, 19%, 20%, 21%, 22%, 23%, 24%, 25%, 26%, 27%, 28%, 20%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% decreased serum cystatin C concentration) relative to the serum cystatin C concentration in individuals diagnosed with a complement-related nephropathy who have not been administered a therapeutic that inhibits the expression or activity of C5. Measurement of serum cystatin C concentration is routine in the art and can be performed by any known means.

In further embodiments, improved kidney function can be shown by decreased urinary C5a concentration. Specifically, administering a clinically effective amount of a therapeutic that inhibits the expression or activity of C5 to an individual diagnosed with or thought to have a complement-related nephropathy can result in about 40-85% decreased urinary C5a concentration (such as any of about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 56%, 66%, 67%, 68%, 69%, 70%, 71%, 72%, 73%, 74%, 75%, 76%, 77%, 78%, 79%, 80%, 81%, 82%, 83%, 84%, or 85% decreased urinary C5a concentration) relative to the urinary C5a concentration in individuals diagnosed with a complement-related nephropathy who have not been administered a therapeutic that inhibits the expression or activity of C5. Measurement of urinary C5a concentration is routine in the art and can be performed by any known means.

Also provided herein are methods for decreasing glomerular membrane attack complex (MAC) formation in an individual diagnosed with or thought to have a complement-related nephropathy. The method includes administering a clinically effective amount of a therapeutic, such as any of the therapeutics described above. Administration of the therapeutic results in decreased glomerular MAC formation relative to glomerular MAC formation in individuals diagnosed a complement-related nephropathy that have not been administered the therapeutic. For example, administering a clinically effective amount of a therapeutic that inhibits the expression or activity of C5 to an individual diagnosed with or thought to have a complement-related nephropathy can result in about 5-20% decreased MAC formation (such as any of about 5%, 6%, 7%, 8%, 9%, 10%, 11%, 12%, 13%, 15%, 15%, 16%, 17%, 18%, 19%, or 20% decreased MAC formation) relative to the MAC formation in individuals diagnosed with a complement-related nephropathy that have not been administered a therapeutic that inhibits the expression or activity of C5. Measurement of MAC formation is routine in the art and can be performed by any known means (such as, without limitation, immunohistochemical staining of the C9 component of the MAC on glomerular tufts in kidney tissue from the individual).

Further provided herein are methods for decreasing immune cell infiltration in into the glomerulus or interstitium of a kidney of an individual diagnosed with or thought to have a complement-related nephropathy. The method requires administering a clinically effective amount of a therapeutic, such as any of the therapeutics described above. Administration of the therapeutic results in decreased immune cell infiltration in the kidneys of the individual relative to immune cell infiltration in the kidneys of individuals diagnosed with a complement-related nephropathy who have not been administered the therapeutic. In some embodiments, the immune cell is a neutrophil that infiltrates the glomerulus. The immune cell can also be a macrophage that infiltrates the interstitium. For example, administering a clinically effective amount of a therapeutic that inhibits the expression or activity of C5 to an individual diagnosed with or thought to have a complement-related nephropathy can result in about 50-100% decreased glomerular neutrophil infiltration (such as any of about 50%, 51%, 52%, 53%, 54%, 55%, 56%, 57%, 58%, 59%, 60%, 61%, 62%, 63%, 64%, 56%, 66%, 67%, 68%, 69%, 70%, 71%, 72%, 73%, 74%, 75%, 76%, 77%, 78%, 79%, 80%, 81%, 82%, 83%, 84%, 85%, 86, 87, 88, 89, 90, 91, 92, 93, 94, 95, 96, 97, 98, 99, or 100% decreased glomerular neutrophil infiltration) relative to glomerular neutrophil infiltration in the kidneys of individuals diagnosed with a complement-related nephropathy who have not been administered a therapeutic that inhibits the expression or activity of C5. As another example, administering a clinically effective amount of a therapeutic that inhibits the expression or activity of C5 to an individual diagnosed with or thought to have a complement-related nephropathy can result in about 30-70% decreased interstitial macrophage infiltration (such as any of about 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 560, 57%, 58%, 59%, 60%, 61%, 62%, 63%, 64%, 56%, 66%, 67%, 68%, 69%, or 70%, decreased interstitial macrophage infiltration) relative to interstitial macrophage infiltration in the kidneys of individuals diagnosed with a complement-related nephropathy who have not been administered a therapeutic that inhibits the expression or activity of C5. Measurement of immune cell infiltration is commonly known in the art and can be performed by any known means (such as, without limitation, immunohistochemical staining of Gr-1 on the surface of neutrophils or staining of F4/80 on the surface of macrophages).

Additionally provided herein are methods for decreasing glomerular size and/or mesangial matrix expansion in a kidney of an individual diagnosed with or thought to have a complement-related nephropathy. The method includes administering a clinically effective amount of a therapeutic, such as any of the therapeutics described above. Administration of the therapeutic results in decreased decreasing glomerular size and/or mesangial matrix expansion relative to glomerular size and/or mesangial matrix expansion in the kidneys of individuals diagnosed with a complement-related nephropathy who have not been administered the therapeutic. Specifically, administering a clinically effective amount of a therapeutic that inhibits the expression or activity of C5 to an individual diagnosed with or thought to have a complement-related nephropathy can result in about 15-30% decreased glomerular size and/or mesangial matrix expansion (such as any of about 15%, 15%, 160%, 17%, 18%, 19%, 20%, 21%, 22%, 23%, 24%, 25%, 26%, 27%, 28%, 29%, or 30%, decreased glomerular size and/or mesangial matrix expansion) relative to glomerular size and/or mesangial matrix expansion in individuals diagnosed with a complement-related nephropathy that have not been administered a therapeutic that inhibits the expression or activity of C5. Measurement of glomerular size and/or mesangial matrix expansion is routine in the art and can be performed by any known means (such as by staining and light microscopic evaluation of kidney tissue derived from the individual).

Also provided herein are methods for improving life expectancy of an individual diagnosed with or thought to have a complement-related nephropathy. The method includes administering a clinically effective amount of a therapeutic, such as any of the therapeutics described above. Administration of the therapeutic results in increased life expectancy relative to life expectancy of individuals diagnosed with a complement-related nephropathy who have not been administered the therapeutic. Specifically, administering a clinically effective amount of a therapeutic that inhibits the expression or activity of C5 to an individual diagnosed with or thought to have a complement-related nephropathy can result in about 10-70% increased life expectancy (such as any of about 10%, 11%, 12%, 13%, 15%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 56%, 66%, 67%, 68%, 69%, or 70% increased life expectancy) relative to life expectancy in individuals diagnosed with a complement-related nephropathy that have not been administered a therapeutic that inhibits the expression or activity of C5.

Further provided herein are methods for decreasing weight loss in an individual diagnosed with or thought to have a complement-related nephropathy. The method includes administering a clinically effective amount of a therapeutic, such as any of the therapeutics described above. Administration of the therapeutic results in decreased weight loss relative to weight loss of individuals diagnosed with a complement-related nephropathy who have not been administered the therapeutic. Specifically, administering a clinically effective amount of a therapeutic that inhibits the expression or activity of C5 to an individual diagnosed with or thought to have a complement-related nephropathy can result in about 10-70% decreased weight loss (such as any of about 10%, 11%, 12%, 13%, 15%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 56%, 66%, 67%, 68%, 69%, or 70% decreased weight loss) relative to weight loss in individuals diagnosed with a complement-related nephropathy that have not been administered a therapeutic that inhibits the expression or activity of C5.

The methods disclosed herein can be further understood by reference to the following examples, which are provided by way of illustration and are not in any way meant to be limiting.

EXAMPLES

Example 1: Replacement of the Endogenous Mouse C3 Gene with a Human C3 Gene (I) Creation of MAID 6149 HO and MAID 6156 HO Mice.

MAID 6149 Mice—Replacement with Human C3 Promoter and Coding Exons 1 Through 41:

The human C3 gene containing 5' regulatory elements and all of the coding exons 1 through 41 of the human C3 gene replaced the murine C3 gene locus spanning 5' regulatory elements and all of the coding exons 1 through 41 (FIG. 1A).

Preliminarily, a targeted deletion of 25 kb of the mouse C3 gene was generated in mouse ES cells by replacement of coding exons 2 through 41 and including 900 bp 3' to the polyadenylation site with a floxed neo cassette. The resultant mouse ES cells, 12132 ES cells, are a heterozygous C3 knockout. 12132 cells were used to generate C3 knockout mice according to procedures known in the art.

A targeting construct was generated containing mouse C3 upstream and downstream homology arms flanking a human C3 sequence extending from 5' regulatory elements upstream of coding exon 1 through coding exon 41 and the 3' untranslated region and a floxed hygro selection cassette, and electroporated into 12132 ES cells. Correctly targeted ES cells (MAID 6148) were further electroporated with a transient Cre-expressing vector to remove the drug selection cassette. Targeted ES cell clones without drug cassette (MAID 6149) were introduced into an 8-cell stage mouse embryo. F0 mice fully derived from the donor ES cell bearing the humanized C3 gene were identified by genotyping for loss of mouse allele and gain of human allele using a modification of allele assay (see, Valenzuela et al. (2003)). MAID 6149 mice contain about 53.4 kb of human sequence including about 9 kb upstream of human C3 exon 1, the entire human C3 gene of about 42.8 kb, and about 1.5 kb of human sequence downstream of the polyA signal; and this 53.4 kb human sequence has replaced about 30.6 kb of mouse sequence including about 6.5 kb of mouse sequence upstream of mouse C3 exon 1, and the mouse C3 gene of about 24.1 kb from the beginning of exon 1 to the stop codon.

Confirmation that the floxed neo cassette replaced the deleted mouse C3 gene sequence in the C3 knockout 12132 ES cells was confirmed by a TaqMan™ qPCR assay that comprises the following primer-probe sets (written 5' to 3'): 12132TU, mouse C3 intron 1: forward primer, GGCCTGATTA CATGGACCTG TC (SEQ ID NO: 1); reverse primer, CCCAGGCTTG GCTGGAATG (SEQ ID NO:2); probe, FAM-TGTCCACTCT GGAAGCCCAG GC-BHQ (SEQ ID NO:3); 12132TD, 3' of mouse C3 exon 41: forward primer, GCCAGGAGAG GAAGCTGGAG (SEQ ID NO:4); reverse primer, TGGCTCAGCA GTAAAGAACA C (SEQ ID NO:5); probe, FAM-ACAGATTGCT GTGAGCT-GCC CAAA-BHQ (SEQ ID NO:6); neo cassette: forward primer, GGTGGAGAGG CTATTCGGC (SEQ ID NO:7);

reverse primer, GAACACGGCG GCATCAG (SEQ ID NO:8); probe, FAM-TGGGCACAAC AGACAATCGG CTG-BHQ (SEQ ID NO:9).

Confirmation that the human C3 gene sequence replaced the deleted mouse C3 gene sequence in the humanized allele was confirmed by a TaqMan™ qPCR assay that comprises the following primer-probe sets (written 5' to 3'): mC3-1, mouse C3 promoter: forward primer, GCCAGCCTAG CCTACTTCA (SEQ ID NO: 10); reverse primer, GCCAC-CCATC CCAGTTCT (SEQ ID NO: 11); probe, FAM-CAGCCCAGGC CCTTTAGATT GCA-BHQ (SEQ ID NO:12); mC3-2, mouse C3 3' untranslated region, forward primer, TACGGTGTTA GGTTCACTAT TGGT (SEQ ID NO:13); reverse primer, GTCGCCAGCA GTCTCATACA G (SEQ ID NO:14); probe, CAL Orange-AGTGGGCATC CCTTGCCAGG C-BHQ (SEQ ID NO:26); hygro cassette: forward primer, TGCGGCCGAT CTTAGCC (SEQ ID NO: 15); reverse primer, TTGACCGATT CCTTGCGG (SEQ ID NO: 16); probe, FAM-ACGAGCGGGT TCGGCCCATT C-BHQ (SEQ ID NO:27); hC3-1, human C3 promoter: forward primer, GGGCCTCCTA AGTTTGTTGA GTATC (SEQ ID NO: 17); reverse primer, CAGGGCTGGT TCCCTAGAAA TC (SEQ ID NO: 18); probe, FAM-TA-CAATAGCA GGCACAGCAC CCA-BHQ (SEQ ID NO:19); hC3-2, human C3 intron 1: forward primer, GGCT-GAGAGT GGGAGTCATG (SEQ ID NO:20); reverse primer, GCACTTGCCA ATGCCATTAT C (SEQ ID NO:21); probe, FAM-CTGCTGTCCT GCCCATGTGG TTG-BHQ (SEQ ID NO:22); hC3-3, human C3 exon 41: forward primer, CGAATGCCAA GACGAAGAGA AC (SEQ ID NO:23); reverse primer, GGGCACCCAA AGA-CAACCAT (SEQ ID NO:24); probe, CAL Orange-CA-GAAACAAT GCCAGGACCT CGGC-BHQ (SEQ ID NO:25).

The same LONA assay is used to assay DNA purified from tail biopsies for mice derived from the targeted ES cells to determine their C3 genotypes and confirm that the humanized C3 allele had transmitted through the germ-line. Two pups heterozygous for the replacement are bred to generate a mouse that is homozygous for the replacement of the endogenous mouse C3 gene by the human C3 gene. Pups that are homozygous for the replacement are used for phenotyping.

The sequences of the junction of the murine C3 locus and the sequence containing the human C3 gene, the junction of the sequence containing the human C3 gene and the floxed hygro selection cassette, and the junction of the sequence of the floxed hygro selection cassette and the murine C3 locus are determined as described above in U.S. Patent Application Publication No. 20150313194, the disclosure of which is incorporated by reference herein.

Figure 1B:
FIG. 1B provides an illustration, not to scale, of the mouse (mC3) and humanized (hC3) C3 genomic loci. The mouse C3 gene spanning a portion of intron 1 and the coding region from exon 2 through exon 41 are deleted and replaced by a portion of intron 1 and the coding region from exon 2 through exon 41 of the human C3 gene and a loxP site, as indicated by a bold line and an arrow, respectively.
Figure 1B:
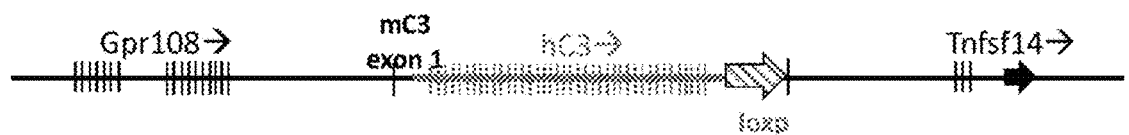

MAID 6156 Mice—Replacement with Human C3 Coding Exons 2 Through 41:

The human C3 gene containing coding exons 2 through 41 of the human C3 gene replaced the murine C3 gene locus spanning coding exons 2 through 41. The methods described above were basically used to replace the mouse C3 gene sequences with human C3 gene sequences (FIG. 1B).

Preliminarily, a targeted deletion of 25 kb of the mouse C3 gene was generated in mouse ES cells by replacement of coding exons 2 through 41 and including 900 bp 3' to the polyadenylation site with a floxed neo cassette. The resultant mouse ES cells, 12132 ES cells, are a heterozygous C3 knockout.

A targeting construct was generated containing mouse C3 upstream and downstream homology arms flanking a human C3 sequence extending from upstream of coding exon 2 through coding exon 41 and the 3' untranslated region and a floxed hygro selection cassette, and electroporated into 12132 ES cells. Correctly targeted ES cells (MAID 6155) were further electroporated with a transient Cre-expressing vector to remove the drug selection cassette. Targeted ES cell clones without drug cassette (MAID 6156) were introduced into an 8-cell stage mouse embryo. F0 mice fully derived from the donor ES cell bearing the humanized C3 gene were identified by genotyping for loss of mouse allele and gain of human allele as described above.

Confirmation that the floxed neo cassette replaced the deleted mouse C3 gene sequence in the C3 knockout 12132 ES cells, and that the human C3 gene sequence replaced the deleted mouse C3 gene sequence in the humanized allele, was confirmed by a TaqMan™ qPCR assay that comprises the same primer-probe sets (written 5' to 3') as described above for MAID 6149 mice.

The same LONA assay is used to assay DNA purified from tail biopsies for mice derived from the targeted ES cells to determine their C3 genotypes and confirm that the humanized C3 allele had transmitted through the germ-line. Two pups heterozygous for the replacement are bred to generate a mouse that is homozygous for the replacement of the endogenous mouse C3 gene by the human C3 gene. Pups that are homozygous for the replacement are used for phenotyping.

The sequences of the junction of the murine C3 locus and the sequence containing the human C3 gene, the junction of the sequence containing the human C3 gene and the floxed hygro selection cassette, and the junction of the sequence of the floxed hygro selection cassette and the murine C3 locus are determined as described above.

(II) Assays for C3 Serum Concentration.

Serum C3 concentrations were assayed in MAID 6149 mice and MAID 6156 mice using ELISA and Western blot. Briefly, Western blot analysis was done as follows: mouse or normal human serum (NHS) was diluted in PBS. Purified human C3b protein (Calbiochem) was used as a positive control. Mouse C3 deficient serum was used as a negative control. Serum or purified hC3 protein were added to electrophoresis sample loading buffer containing mercaptoethanol and SDS and run on a polyacrylamide gel under reducing/denaturing conditions, then transferred onto nitrocellulose membrane. Blots were blocked, then probed with either polyclonal goat anti-mouse C3 primary antibody (Abnova) or polyclonal goat anti-sera to human C3 (Quidel), followed by detection with donkey anti-goat IgG HRP (Santa Cruz). ThermoScientific Super Signal West Pico Chemiluminescent Substrate was used to develop the blot. GE Image Quant LAS4000 was used for imaging. Serum C3 concentrations were determined with Complement C3 Human ELISA kit and Complement C3 Mouse ELISA kit (Abcam), as per manufacturer's directions. Protein levels were assayed by ELISA as follows: Mouse and human C3 were measured with Complement C3 Mouse ELISA kit (Abcam) and Complement C3 Human ELISA kit (Abcam), respectively, as per manufacturer's directions. Human C3a was measured with BD OptEIA™ Human C3a ELISA Kit (BD Biosciences). Mouse C3a was measured with the following reagents from BD Biosciences: Purified Rat Anti-Mouse C3a Antibody, Biotin Rat Anti-Mouse C3a Antibody, and Purified Mouse C3a Protein (native), as per manufacturer's directions.

Figure 2A:
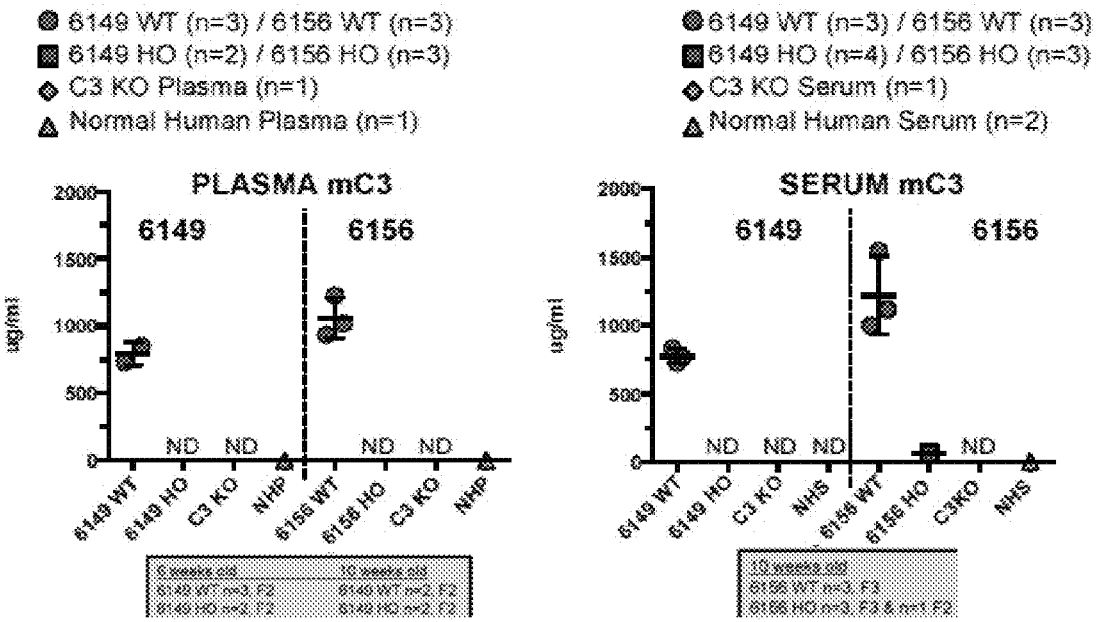
FIG. 2A and FIG. 2B are graphs depicting the results of an ELISA analysis of serum and plasma derived from MAID 6156 and MAID 6149 homozygous mice performed for murine C3 (FIG. 2A) or murine C3a (FIG. 2B). Circles represent 6149 or 6156 wild type (WT) controls; squares represent MAID 6156 and MAID 6149 homozygous mice (HO), diamonds represent C3 knockout (null) animals; and triangles represent normal human plasma (NHP) or normal human serum (NHS). ND=Not detected.
Figure 2B:
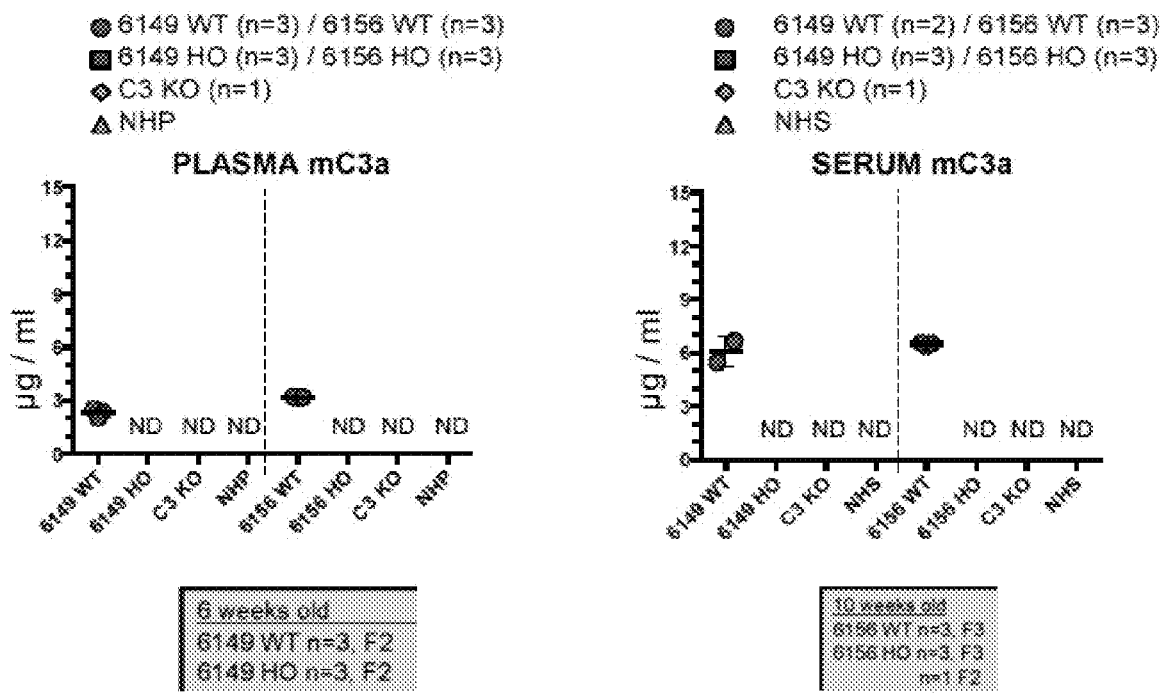
Figure 3A:
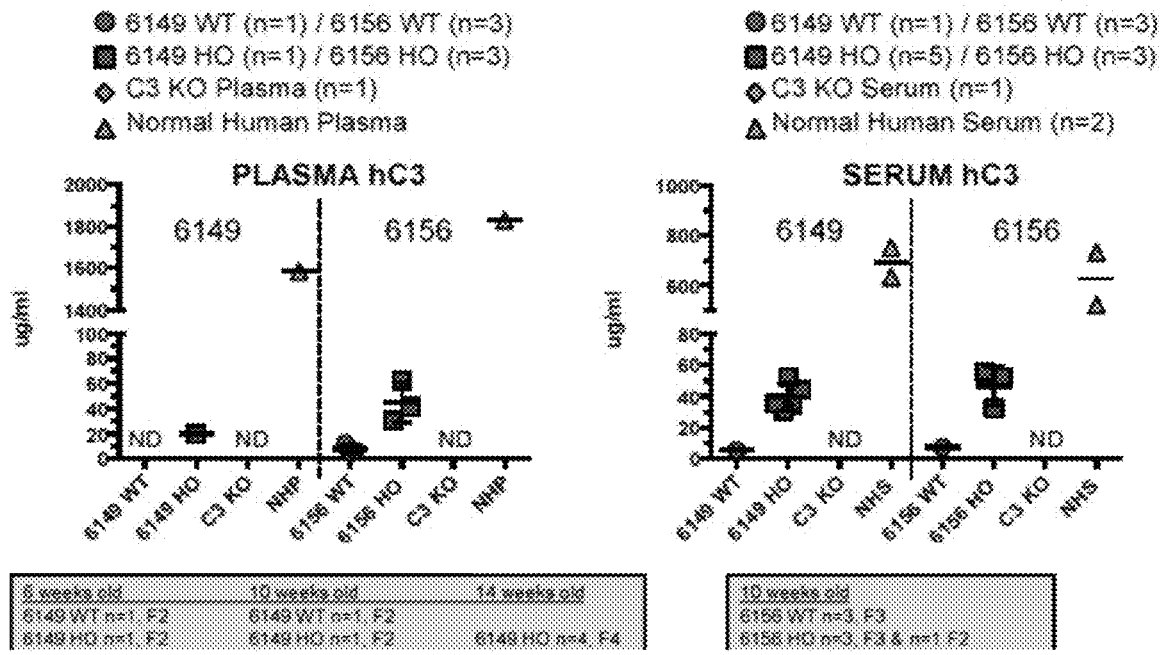
FIG. 3A and FIG. 3B. are graphs depicting the results of ELISA analysis of serum and plasma derived from MAID 6156 and MAID 6149 homozygous mice performed for human C3 (FIG. 3A) or human C3a (FIG. 3B). Circles represent 6149 or 6156 wild type (WT) controls; squares represent MAID 6156 and MAID 6149 homozygous mice (HO), diamonds represent C3 knockout animals; and triangles represent normal human plasma (NHP) or normal human serum (NHS). ND=Not detected.
Figure 3B:
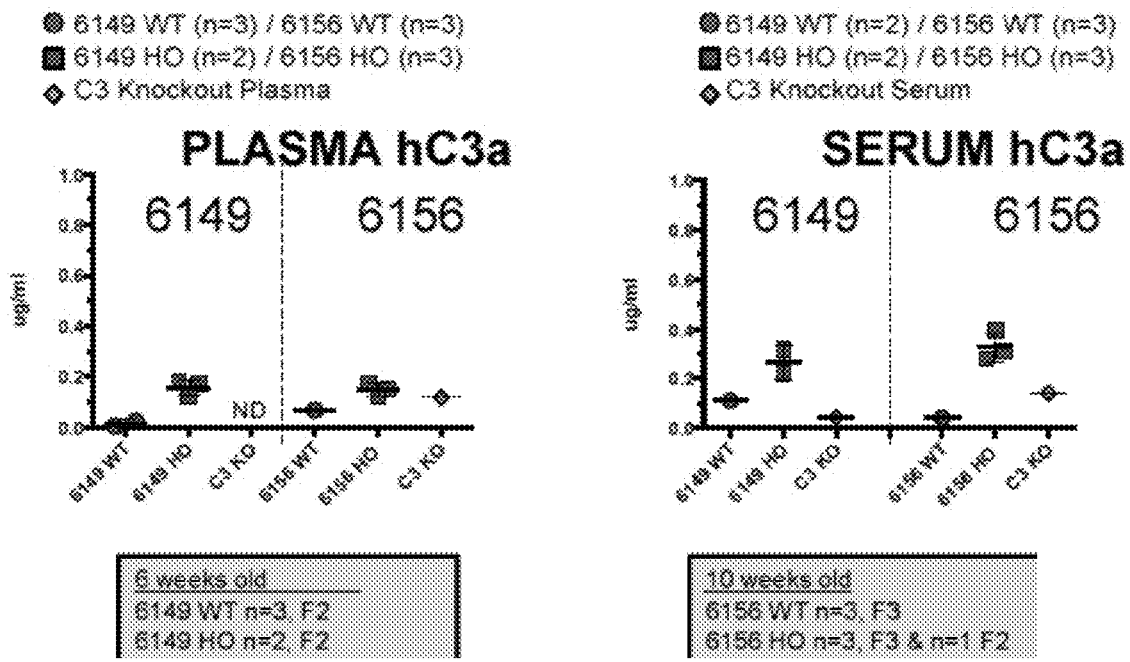
Figure 4:
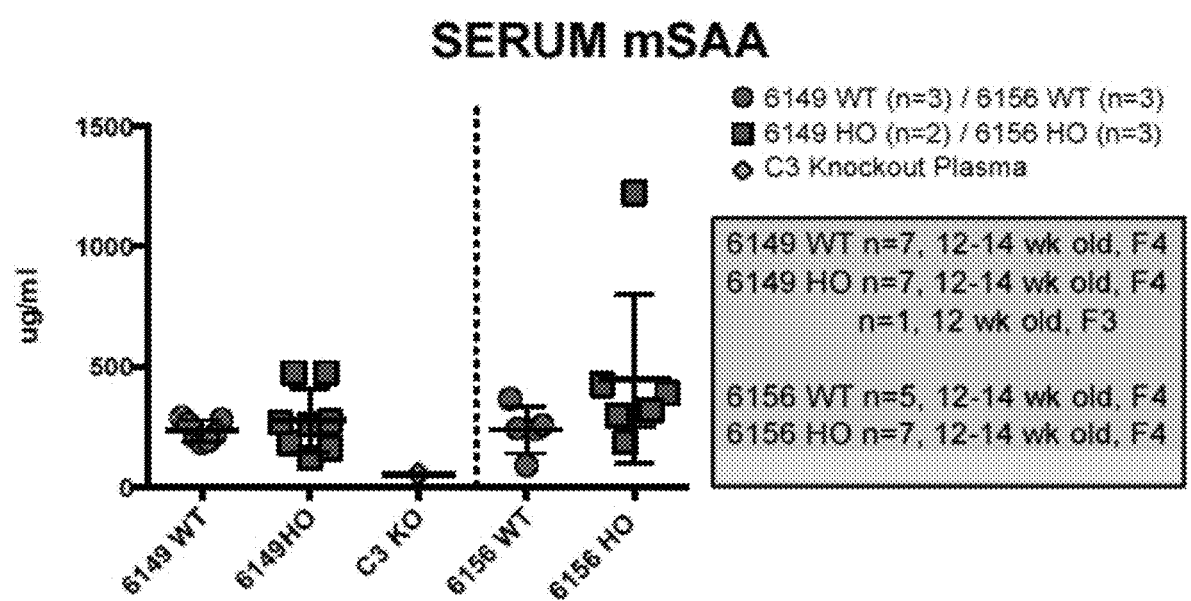
FIG. 4 is a graph depicting the results of ELISA analysis of serum and plasma derived from MAID 6156 and MAID 6149 homozygous mice performed for mouse serum amyloid A protein (mSAA). Circles represent 6149 or 6156 wild type (WT) controls; squares represent MAID 6156 and MAID 6149 homozygous mice (HO), diamonds represent plasma from C3 knockout animals.
Figure 5A:
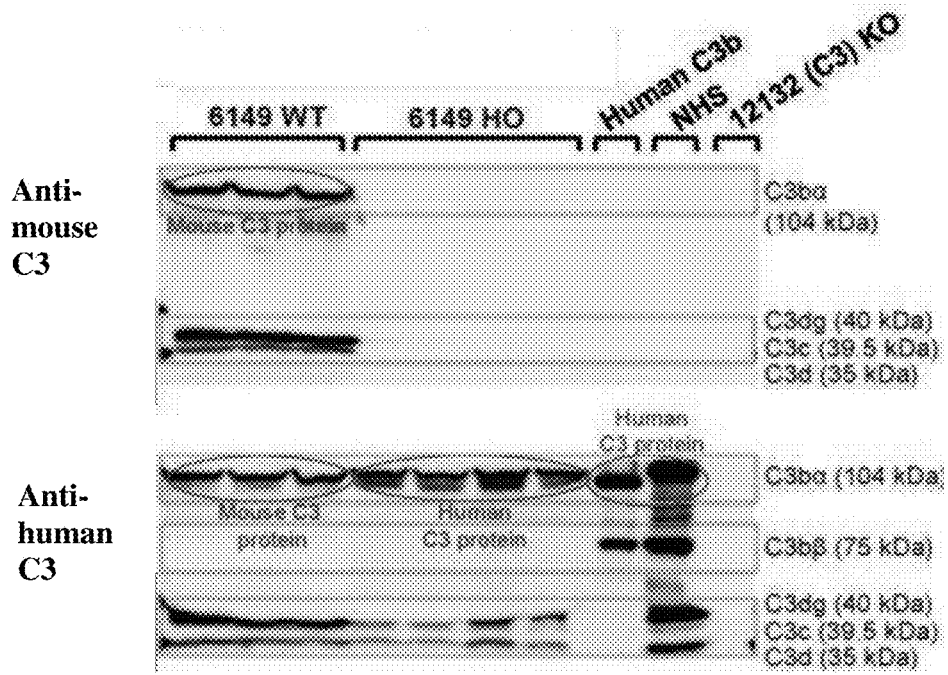
FIG. 5 depicts Western blots performed on serum derived from MAID 6149 (FIG. 5A) and MAID 6156 homozygous mice (FIG. 5B). The anti-human C3 antibody used in this study is cross-reactive with mouse C3.
Figure 5B:
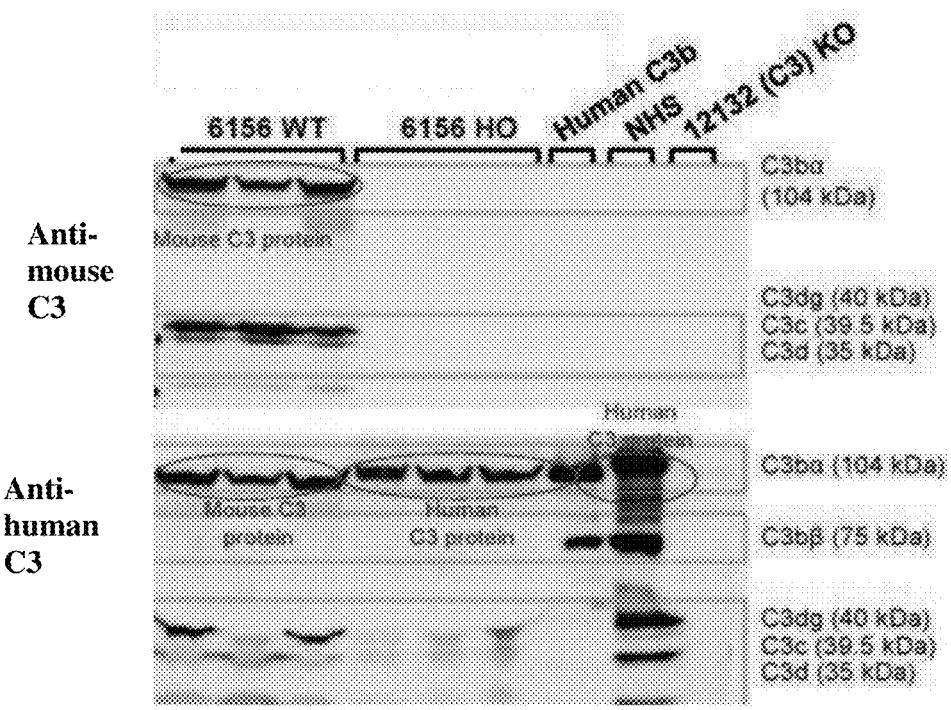

As shown in FIG. 2, ELISA assays revealed that both mouse C3 (FIG. 2A) and mouse C3a (FIG. 2B) were undetectable in serum as well as plasma derived from 6156 homozygous and 6149 homozygous mice at both six and 10 weeks of age relative to wild type controls. In contrast, FIG. 3 shows that human C3 (FIG. 3A) as well as human C3a (FIG. 3B) were detected in plasma and serum derived from 6156 homozygous and 6149 homozygous mice, albeit at lower concentrations than that observed for these proteins in normal human plasma or serum. A control experiment that assayed for the presence of mouse serum amyloid A protein (mSAA) found comparable levels expressed in the C3 humanized homozygous mice compared to their wildtype counterparts. Western blots performed on serum derived from both MAID 6149 and MAID 6156 homozygous animals demonstrated that they express human, but not murine, C3 proteins. The anti-hC3 antibody used in these experiments cross reacted with mouse C3 proteins (FIG. 5A and FIG. 5B).

In summary, this Example demonstrates the creation of humanized C3 mice. Both the MAID 6156 homozygous and MAID 6149 homozygous mice express human C3 protein and do no express any murine C3 protein.

Example 2: Lifespan and Gross Morphology of C3 Humanized Mice (I) Average Age at Death and Weight of C3 Humanized Mice Versus Wildtype.

For these experiments, mortality and age of death were acquired from vivarium records. Additionally, weights of MAID 6156 homozygous and MAID 6149 homozygous mice were monitored in a cohort of mice. Lastly, lean tissue volume, whole body fat volume and % fat volume were determined as follows: Mice were scanned using in vivo Quantum μCT system (PerkinElmer). The X-ray source was set to a current of 160 μA, voltage of 90 kVp. The mouse was anesthetized by isofluorane, and the whole body, excluding the head, was scanned with a field of view at 60 mm×120 mm. The scan took 34 seconds, with a voxel size at 240 μm. The imaging was analyzed by Analyze software (Mayo Clinic). Bone, fat, and lean tissues were segmented by the grey value, and tissues volumes, fat volume fraction, bone mineral density (BMD) and bone mineral content were calculated.

Figure 6:
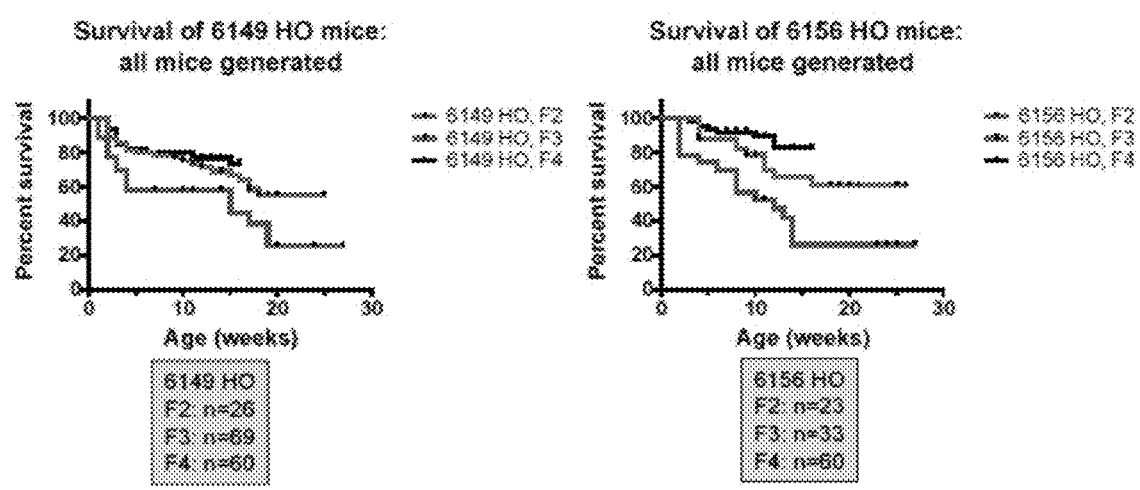
FIG. 6 depicts survival curves for F2, F3, and F4 generations of MAID 6149 (left) and MAID 6156 homozygous mice (right) over time.

Both MAID 6156 homozygous and MAID 6149 homozygous mice exhibited high rates of spontaneous death, particularly in the F2 generation. However, survival was observed to increase in subsequent generations (F3 and F4; FIG. 6).

Figure 7:
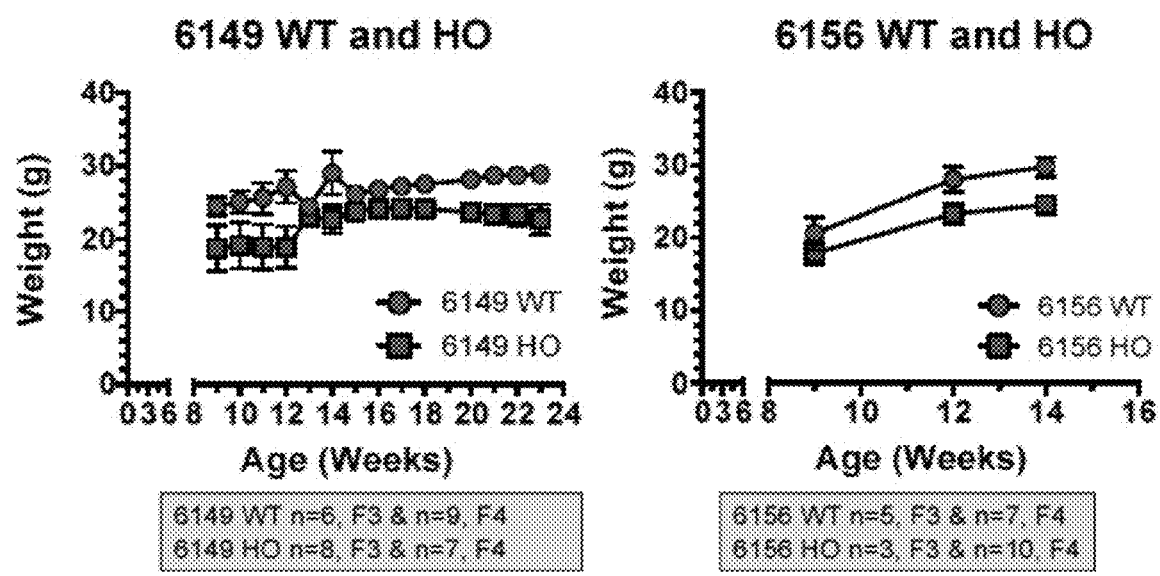
FIG. 7 depicts a graph showing weight loss/gain over time of MAID 6149 (left) and MAID 6156 (right) homozygous (HO) and wildtype (WT) mice.
Figure 8A:
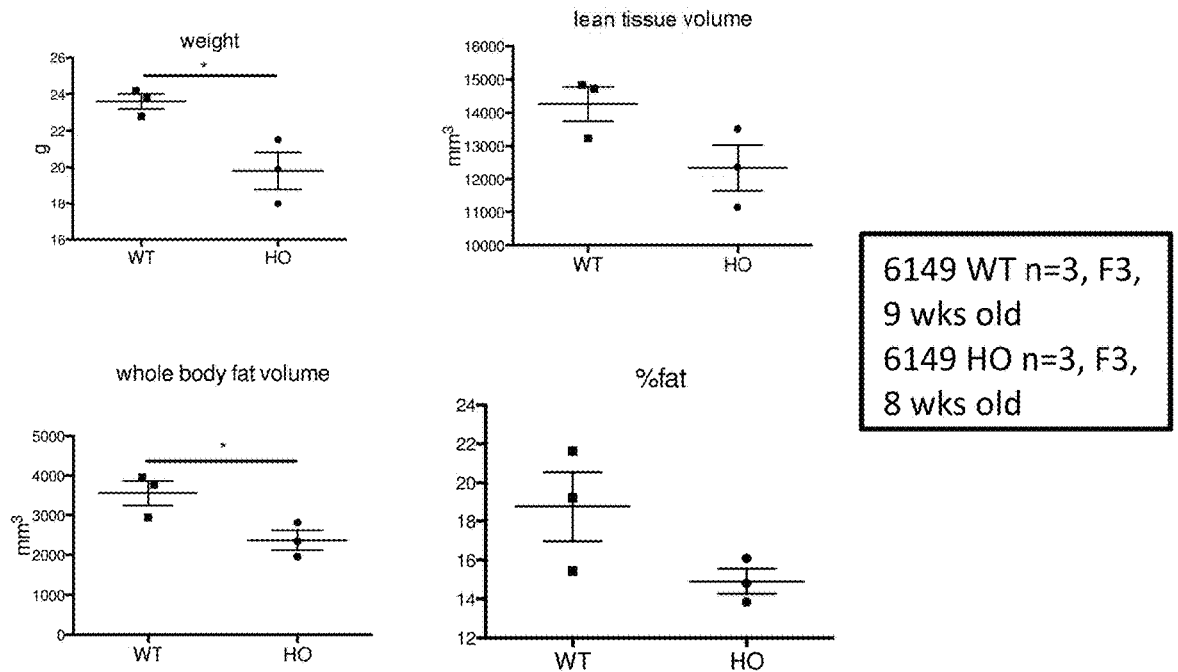
FIG. 8A and FIG. 8B depict graphs showing the results of a body fat analysis conducted on wildtype (WT) and MAID 6149 (FIG. 8A) and MAID 6156 (FIG. 8B) homozygous (HO) mice.
Figure 8B:
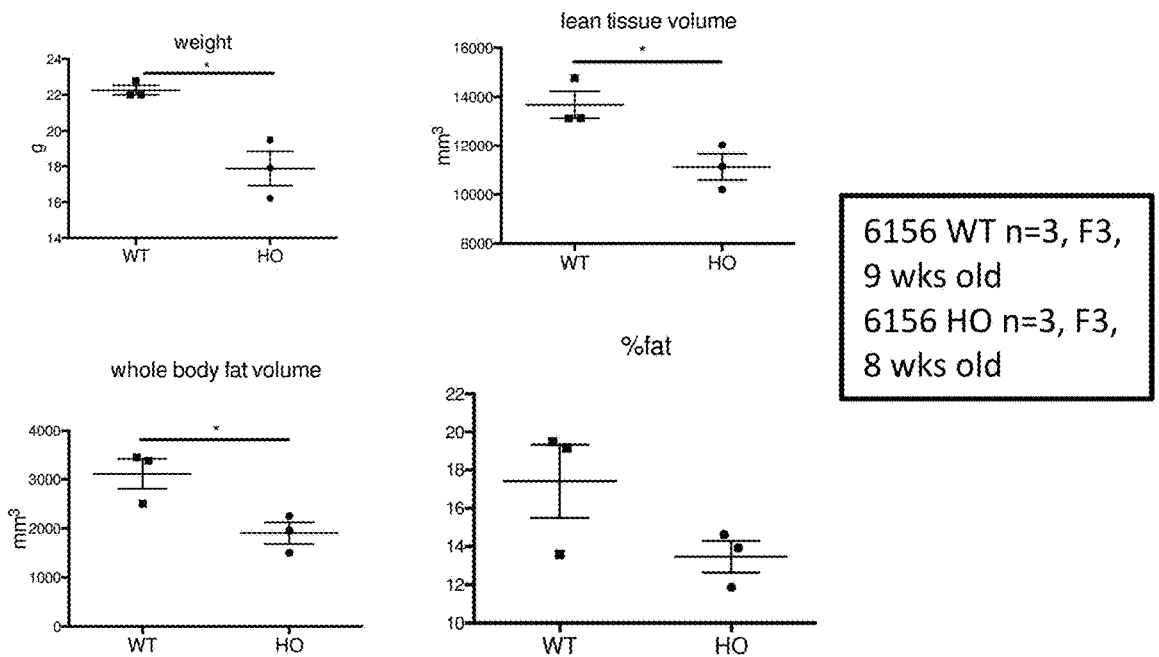
Figure 9A:
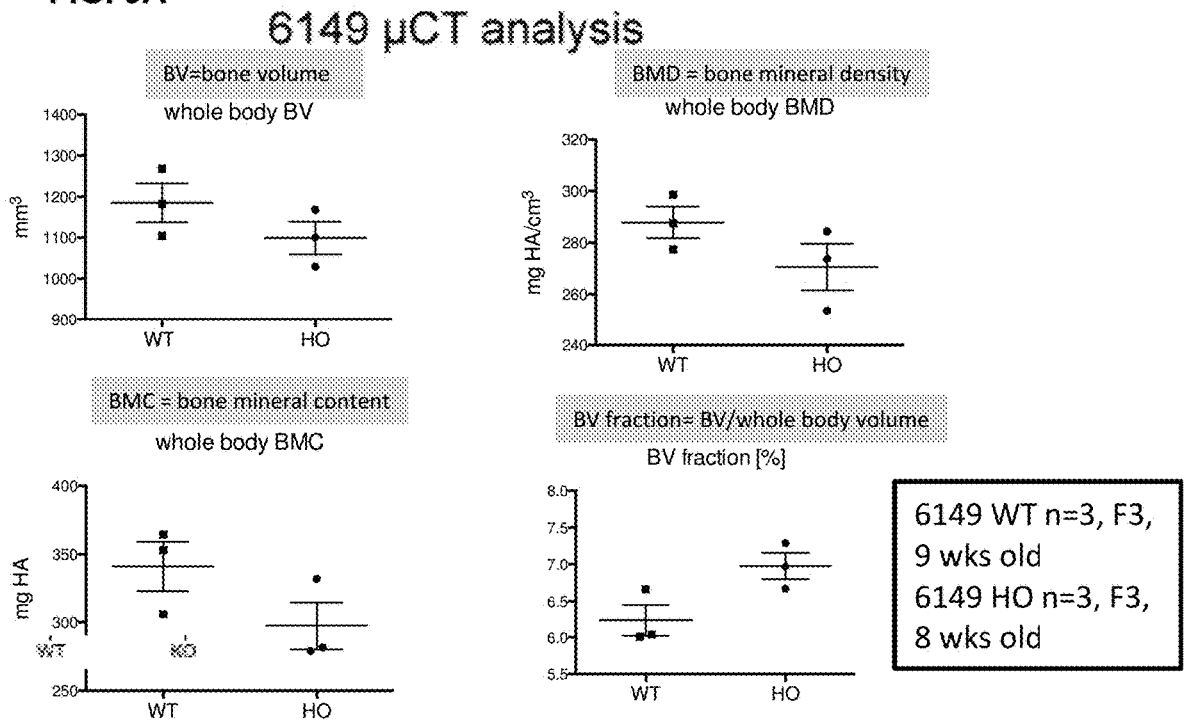
FIG. 9A and FIG. 9B depict graphs showing the results of bone density and bone mineral content analysis conducted on wildtype (WT) and MAID 6149 (FIG. 9A) and MAID 6156 (FIG. 9B) homozygous (HO) mice.
Figure 9B:
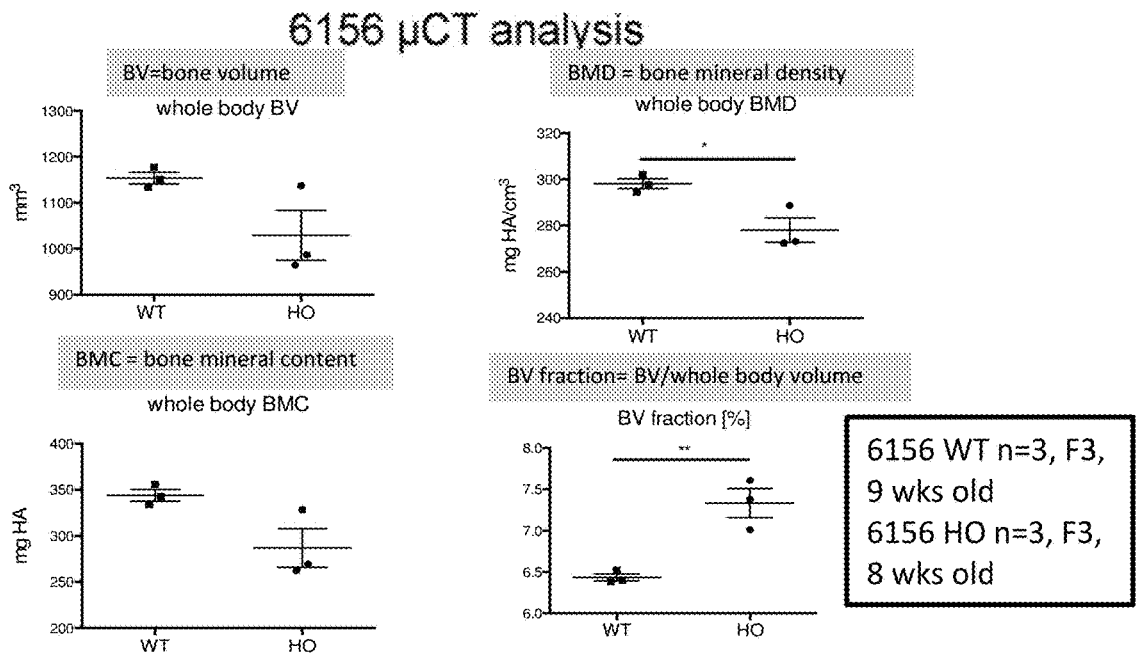

Additionally, both strains of mice exhibited decreased weight compared to comparably-aged wild type mice (FIG. 7). In particular, MAID 6149 mice began to lose weight around week 20 of age. Similarly, both strains of mice exhibited decreases in lean tissue volume, whole body fat volume, and body fat percentage compared to wildtype counterparts (FIG. 8A and FIG. 8B). As shown in FIG. 9, both MAID 6149 (FIG. 9A) and MAID 6156 (FIG. 9B) homozygous mice exhibited both decreased bone density and decreased bone mineral content compared to wildtype counterparts.

In summary, this Example demonstrates that humanized C3 mice exhibit high rates of spontaneous death, decreased weights, decreased body fat percentage, bone density and bone mineral content in comparison to wildtype counterparts.

(II) Gross Morphology of C3 Humanized Mice Versus Wildtype

Gross morphology was assessed in MAID 6156 homozygous C3 humanized mice following spontaneous death by a qualified veterinarian. Post-mortem examination revealed that homozygous mice exhibited brittle bones (ribs, skull, and all other bones) and a noticeable lack of subcutaneous fat compared to wildtype counterparts.

Example 3: Characterization of Kidney and Liver Injury in C3 Humanized Mice (I) Kidney Histopathology In brief, Hematoxylin and Eosin (H&E) stain involves staining with hematoxylin, differentiating with acid alcohol, followed by staining with eosin. Periodic acid-Schiff (PAS) staining of the kidney sections was executed using a commercial vendor (Histoserv Inc.). In brief, 5-micron thin sections were made from formalin-fixed, paraffin-embedded mouse kidney tissues along the sagittal plane to include all the anatomical regions of the kidney. The section were deparaffinized and stained with PAS to detect glycoproteins, glycolipids and mucins in the tissue. Quantitative determination of mesangial matrix expansion in PAS-stained sections was performed as follows. In brief, PAS-stained sections were imaged in an Aperio AT2 Slide Scanner with the 40× objective. For measurements of mesangial cell matrix expansion, at least 25 glomeruli per section were subjected to measurement of PAS-positive area. An optical density-based threshold was applied to each glomerular tuft using a modification of Indica Labs Area Quantification algorithm, separating nuclear staining (dark blue) and background (light pink) from Schiff-positive matrix (bright purple). Matrix and total tuft area were measured and reported, along with mesangial cell matrix as a percentage of tuft area.

Figure 10A:
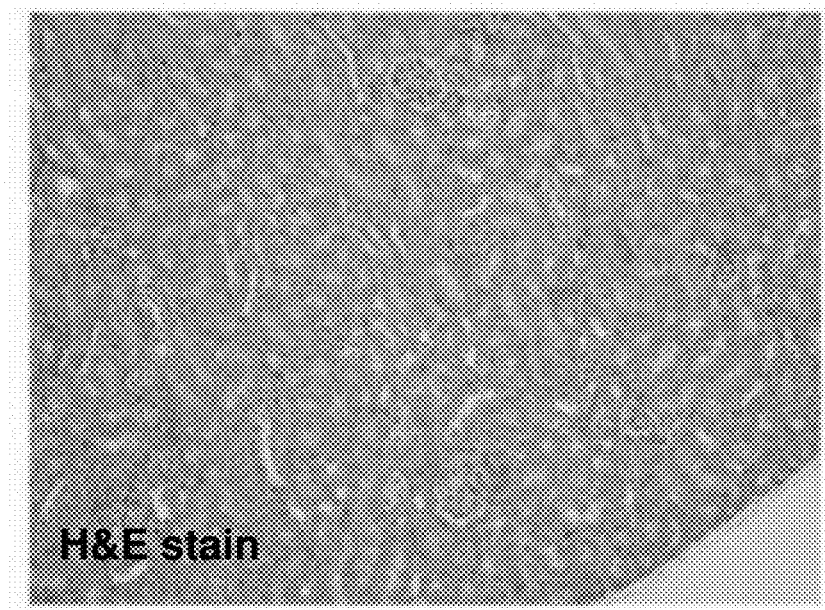
FIG. 10A depicts a cross section of hematoxylin and eosin (H&E) stained kidney tissue obtained from normal mice.
Figure 10B:
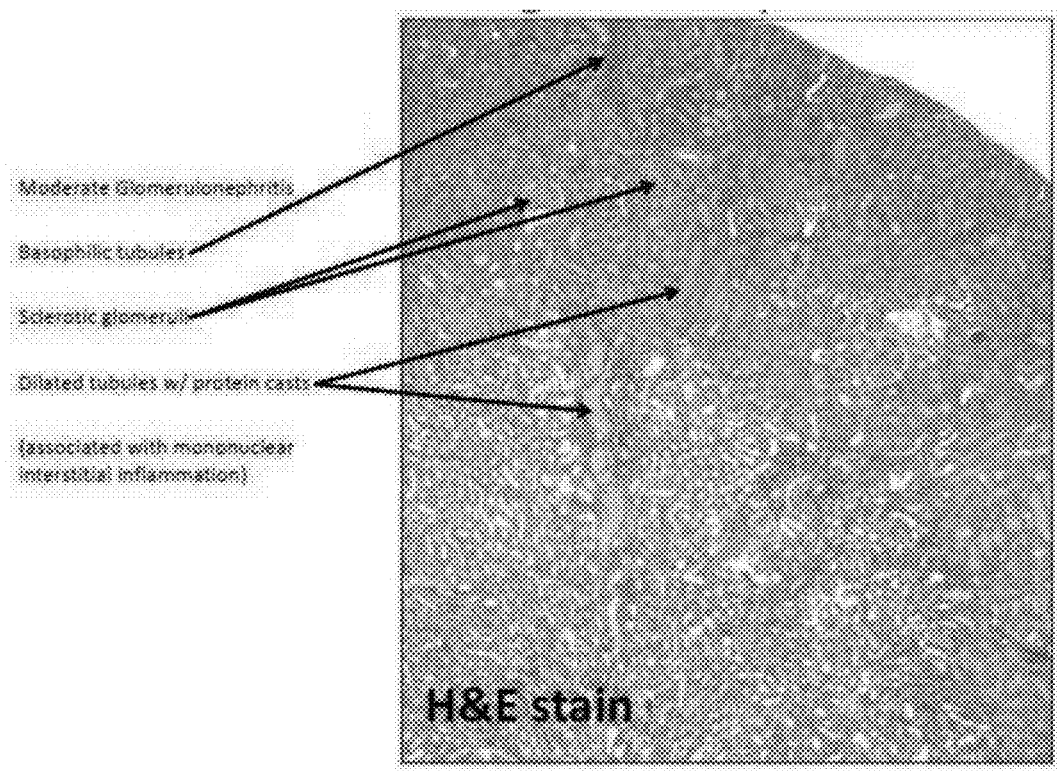
FIG. 10B depicts H&E stained kidney tissue obtained from MAID 6156 homozygous (HO) mice.
Figure 11A:
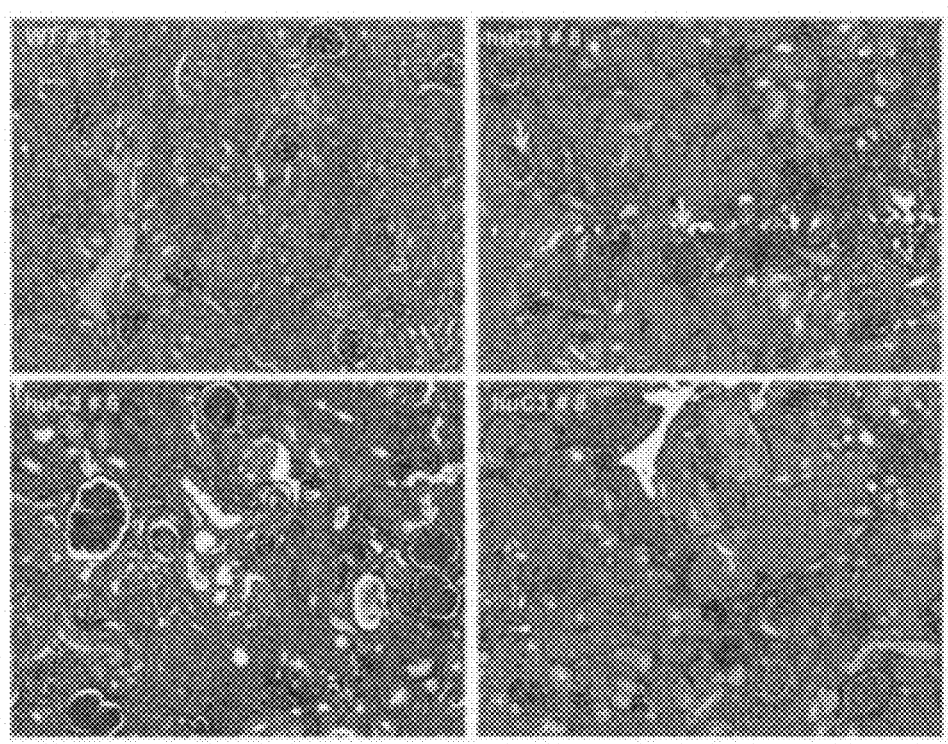
FIG. 11A depicts a cross section of periodic acid-Schiff (PAS)-stained kidney tissue obtained from wildtype (WT) and homozygous humanized C3 mice (huC3) MAID 6149 mice. Images represent mean pathology of the sections. Arrows point to examples of sclerotic glomeruli.
Figure 11B:
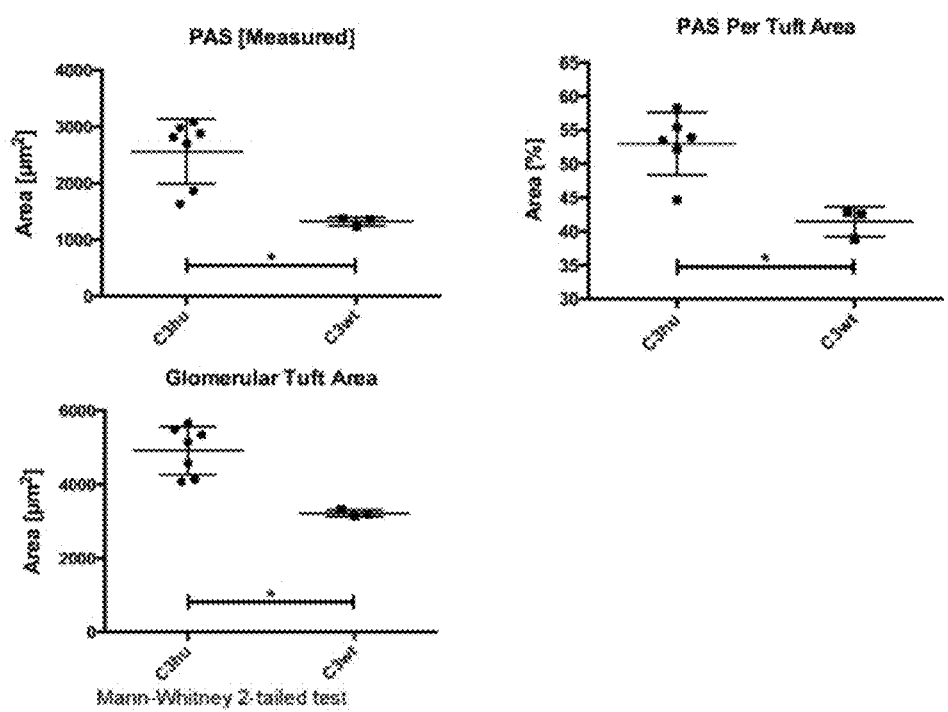
FIG. 11B depicts graphs showing quantification of mesangial matrix expansion in the kidneys of humanized C3 mice (huC3) mice compared to wildtype (C3 wt) mice. Increased glomerular tuft area was indicative of glomerular hypertrophy. Increases in PAS-stained area in the glomerulus were indicative of mesangial matrix expansion.

Histological comparison between the kidneys of normal (FIG. 10A) and MAID 6156 homozygotic mice (FIG. 10B) revealed evidence of glomerulonephritis which included basophilic tubules, sclerotic glomeruli, and dilated tubules with protein casts, which are associated with mononuclear interstitial inflammation. Spontaneous renal disease was present in 6/7 mice observed. Three of these mice had significant glomerulonephritis which, given the young age of the mice, was considered to be early onset for this condition. Further, homozygous mice exhibited evidence of immunosuppression with decreased numbers of lymphocytes being observed in the spleen and Peyer's patches. Further, as shown in FIG. 11A and as quantitated in FIG. 11B, periodic acid-Schiff (PAS)-stained kidneys from humanized C3 mice exhibited mesangial matrix expansion compared to wildtype mice. With respect to the quantitation shown in FIG. 11B, increased glomerular tuft area was indicative of glomerular hypertrophy. Increases in PAS-stained area in the glomerulus was indicative of mesangial matrix expansion.

(II) Serum, Liver, and Urinary Chemistry

Serum levels of sodium, potassium, chloride, calcium, glucose, BUN, lipase, total protein, creatinine, creatine kinase, albumin, amylase, bilirubin, magnesium, phosphate, uric acid, phosphorous, free fatty acids, cholesterol, triglycerides, HDL, non-HDL, and LDL were determined as follows. In brief, serum was tested on an ADVIA Chemistry System, as per manufacturer's directions. Similarly, serum liver enzymes were also tested on an ADVIA Chemistry System, as per manufacturer's directions.

Urinary albumin, urinary creatinine (Exocell Inc.), BUN (BioAssay Systems) and serum cystatin C (BioVendor) were measured according to manufacturers' instructions.

Figure 12:
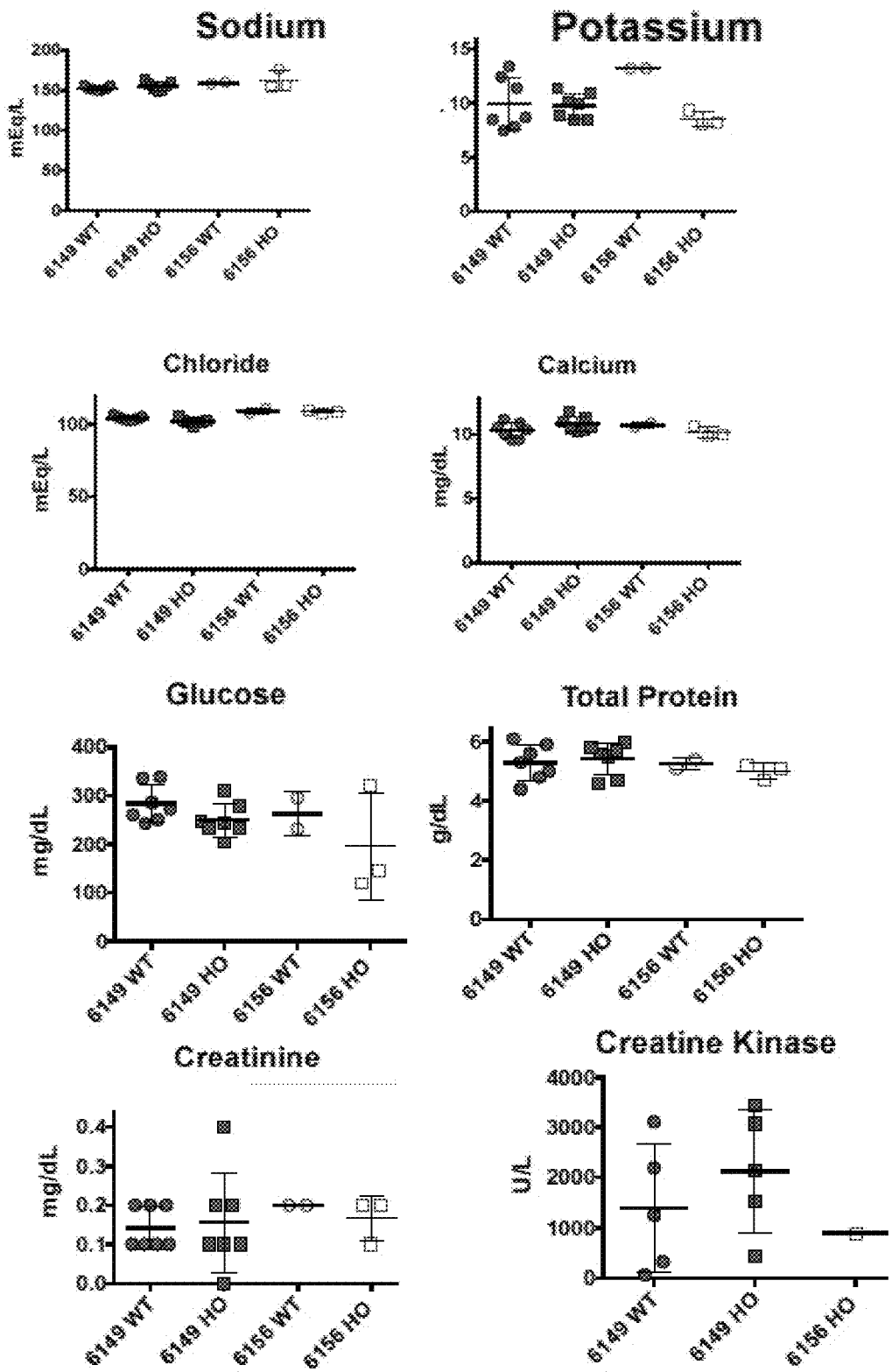
FIG. 12 depicts graphs showing the results of serum chemistry panel analyses for sodium, potassium, chloride, calcium, glucose, total protein, creatinine, creatine kinase, albumin, amylase, total bilirubin, magnesium, inorganic phosphate, uric acid, phosphorus, non-esterified fatty acid, total cholesterol, triglyceride, high density lipoproteins (HDL), and low density lipoprotein (LDL) levels between wildtype (WT) and MAID 6149 and MAID 6156 homozygous (HO) mice.
Figure 12:
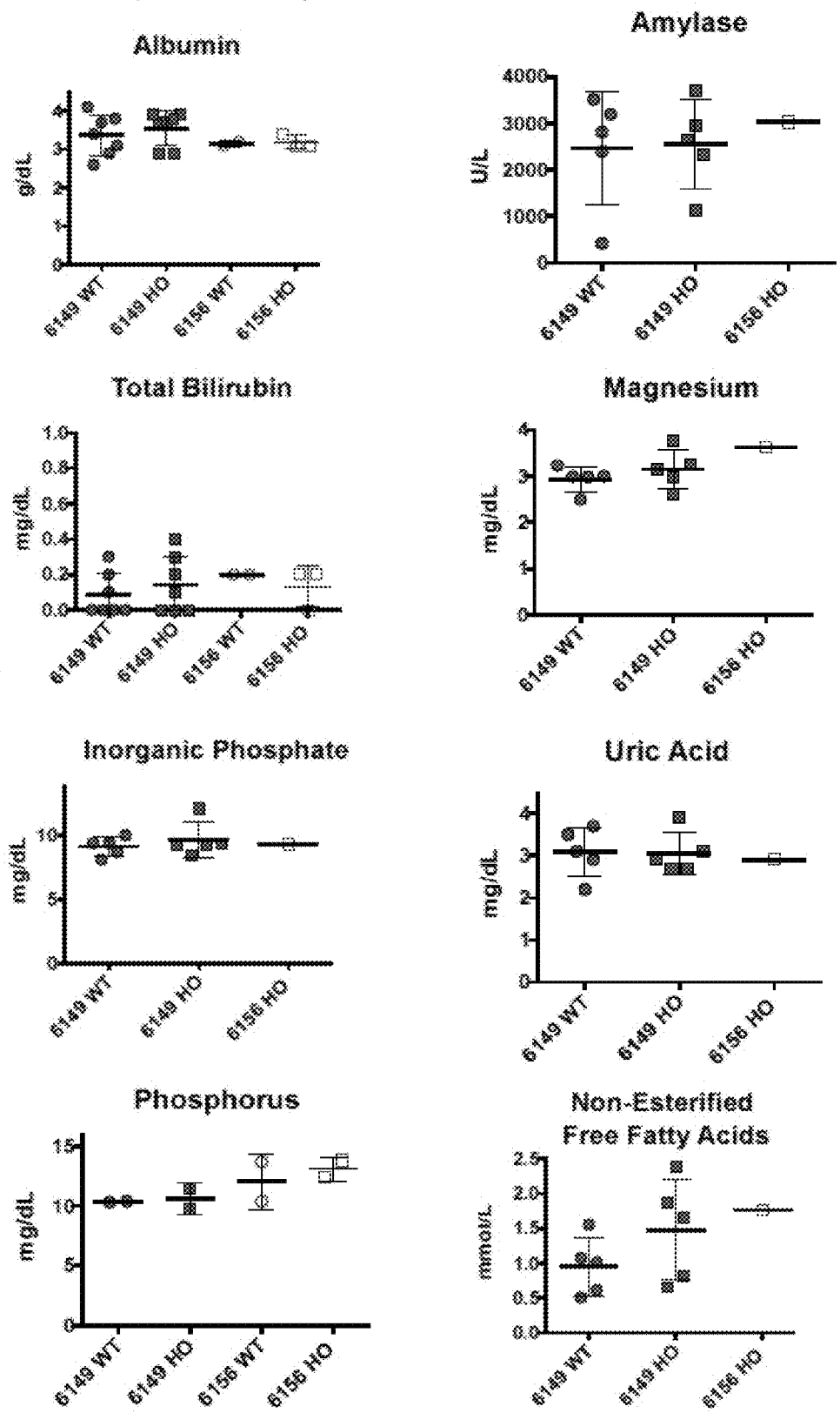
Figure 12:
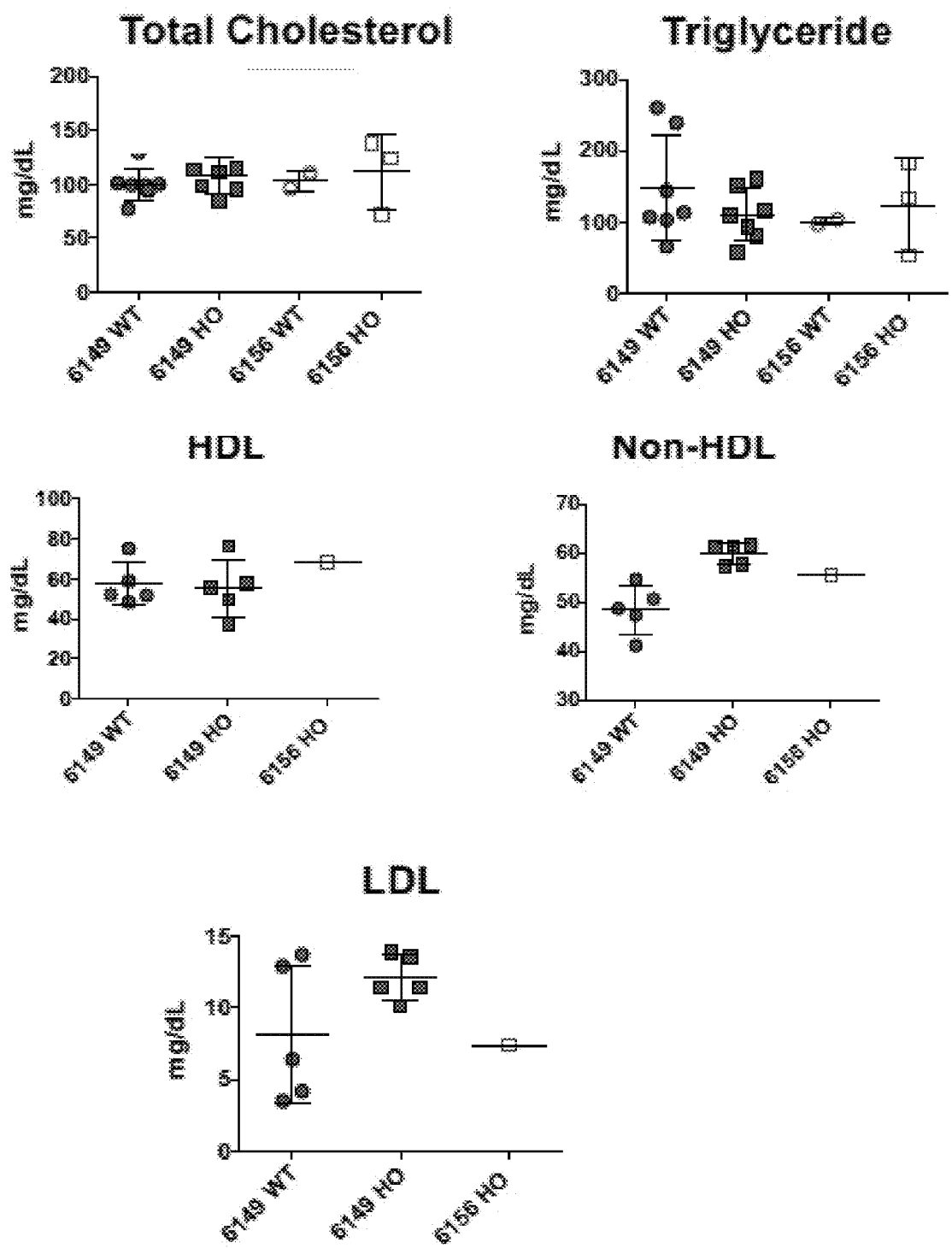
Figure 13A:
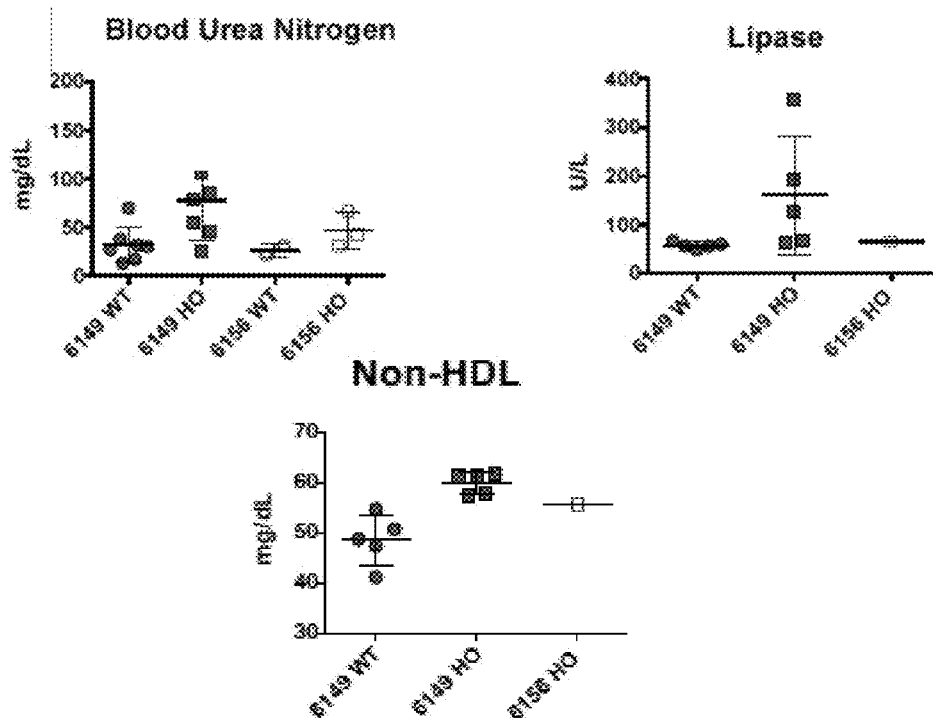
FIG. 13A depicts graphs showing the results of serum chemistry panel analyses for blood urea nitrogen, non-high density lipoproteins (non-HDL), and lipase levels between wildtype (WT) and MAID 6149 and MAID 6156 homozygous (HO) mice.
Figure 13B:
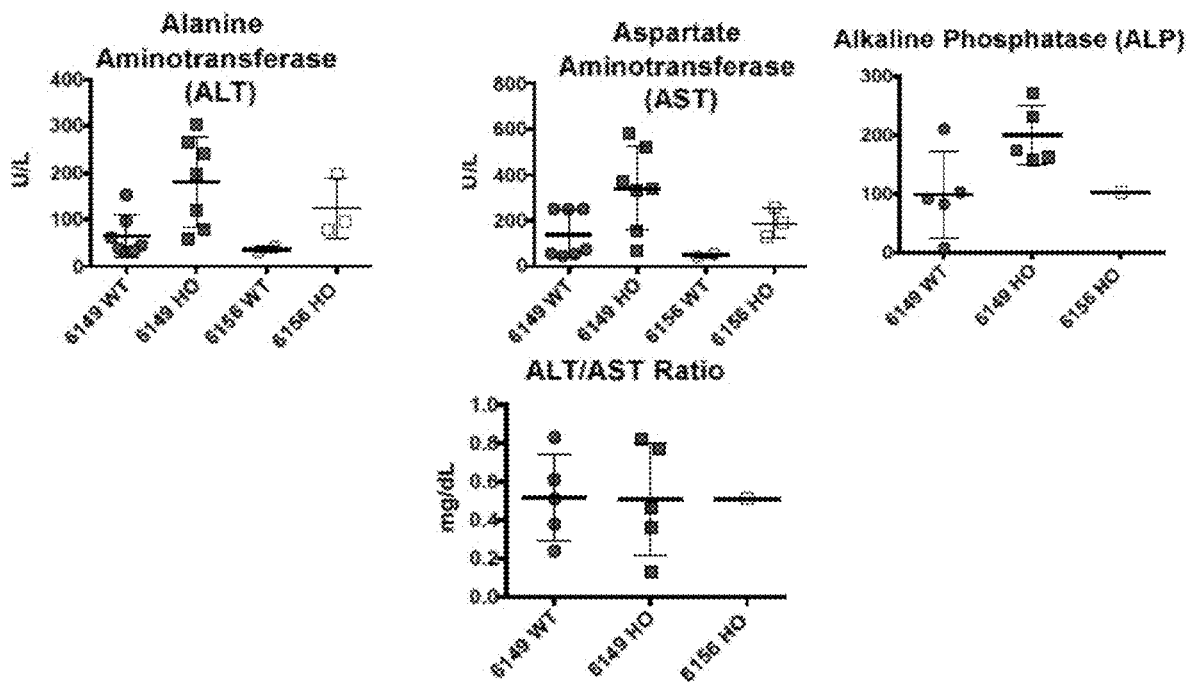
FIG. 13B depicts graphs showing the results of a liver enzyme analyses for alanine aminotransferase (ALT), aspartate aminotransferase (AST), ALT/AST ratio, and alkaline phosphatase (ALP) levels between wildtype (WT) and MAID 6149 and MAID 6156 homozygous (HO) mice.
Figure 14A:
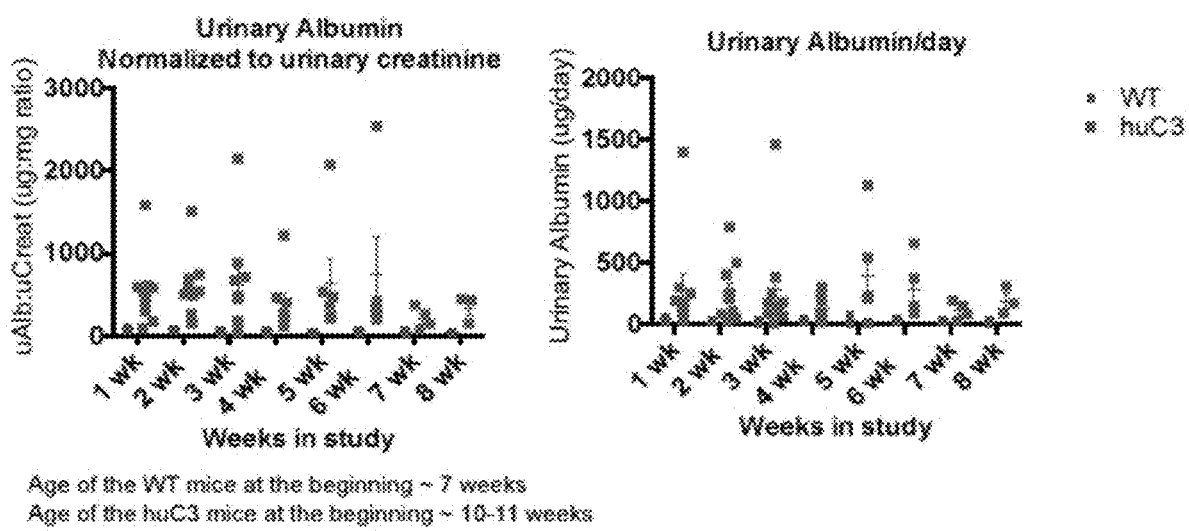
FIG. 14A depicts graphs showing the results of a urinary panel analysis for albumin in wildtype (WT) and humanized C3 (huC3) MAID 6149 mice.
Figure 14B:
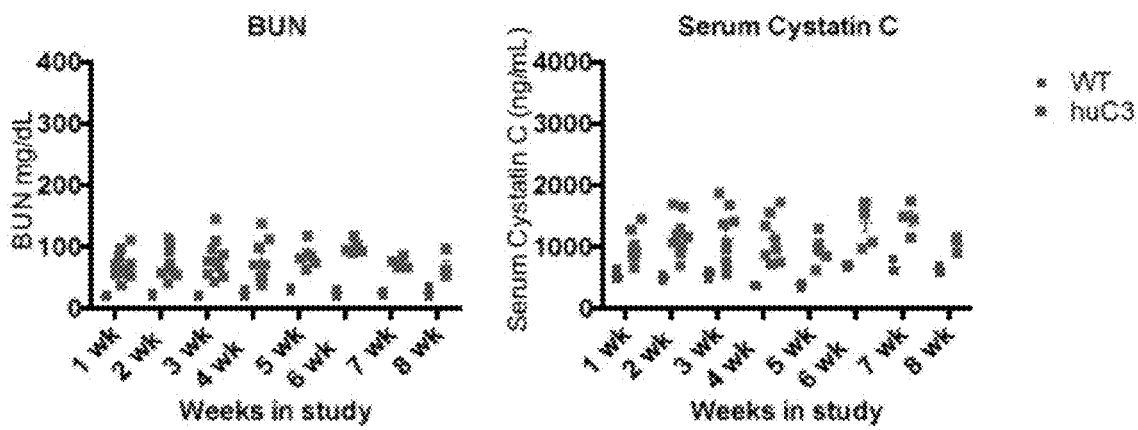
FIG. 14B depicts analysis of serum BUN and cystatin C in wildtype (WT) and humanized C3 (huC3) mice.

No differences were found in the serum chemistry panel analysis for sodium, potassium, chloride, calcium, glucose, total protein, creatinine, creatine kinase, albumin, amylase, total bilirubin, magnesium, inorganic phosphate, uric acid, phosphorus, non-esterified fatty acids, total cholesterol, triglyceride, HDL, and LDL between wildtype and humanized C3 mice (FIG. 12). However, elevated blood urea nitrogen (BUN) as well as elevated levels of lipase and non-HDL were observed in serum obtained from humanized C3 mice compared to wildtype counterparts (FIG. 13A). These results are indicative of kidney dysfunction and also are associated with cardiovascular conditions such as congestive heart failure or recent myocardial infarction. Further, results of a liver enzyme panel showed elevated alanine aminotransferase, aspartate aminotransferase, and alkaline phosphatase levels, which is indicative of liver damage (FIG. 13B). Urinary analysis showed that albumin was elevated in humanized C3 mice in comparison to wildtype counterparts, suggesting kidney dysfunction (FIG. 14A). Further time-course serum analysis revealed that serum BUN and cystatin C were increased in humanized C3 mice indicating of kidney failure (FIG. 14B).

In conclusion, the results of serum, liver enzyme, and urinary analysis on humanized C3 mice are indicative of kidney dysfunction and/or failure as well as liver defects consistent with fibrosis.

Example 4: Abnormal Complement Deposition in the Kidney in C3 Humanized Mice

Cross sections of kidney tissue from MAID 6149 homozygous and wildtype mice were assessed immunofluorescently for the presence of C3 deposition and the C5b-9 membrane attack complex in accordance with the following protocol. In brief, sagittal sections were made from frozen OCT-embedded kidneys, and stained with either rat-anti-mouse C3 monoclonal antibody (Abcam) or rabbit polyclonal C5b-9 antibody (Abcam). A Cy3 donkey anti-rat (Jackson ImmunoResearch) or Cy3 donkey anti-rabbit secondary antibody (Jackson ImmunoResearch) was used to visualize the staining, respectively. Fluorescent images were taken using Leica DM5500 or DM6000 microscope, respectively.

Figure 15A:
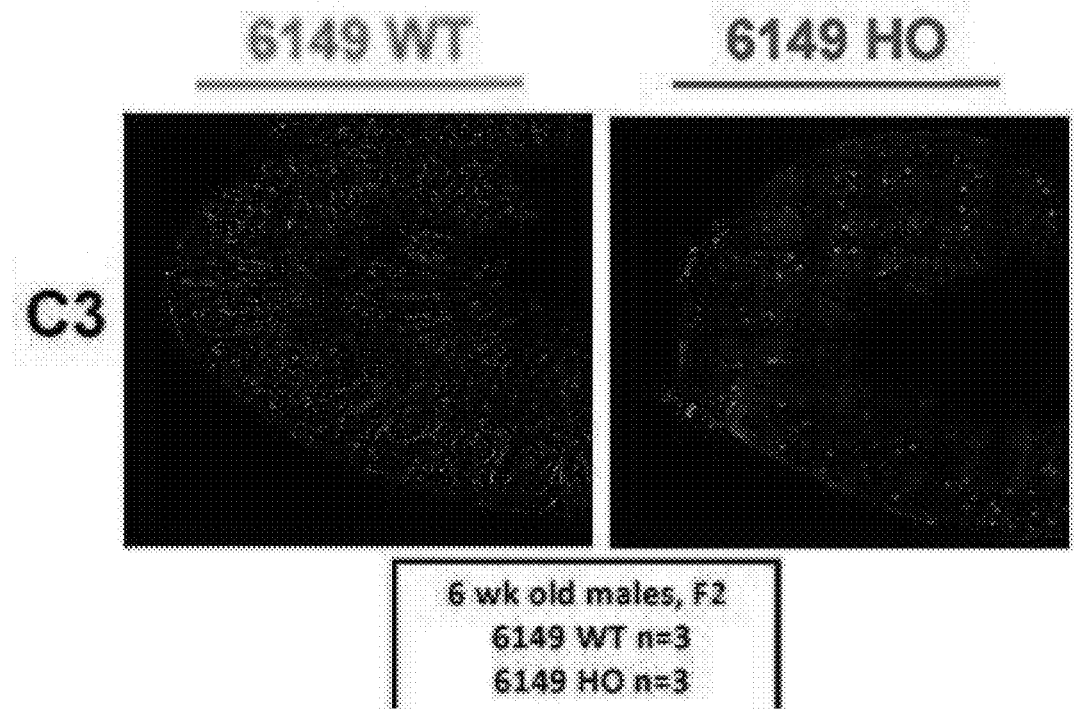
FIG. 15A depicts an immunofluorescent micrograph showing cross sections of kidney tissue obtained from wildtype (WT) and homozygous (HO) humanized C3 MAID 6149 mice stained for human C3 protein.
Figure 15B:
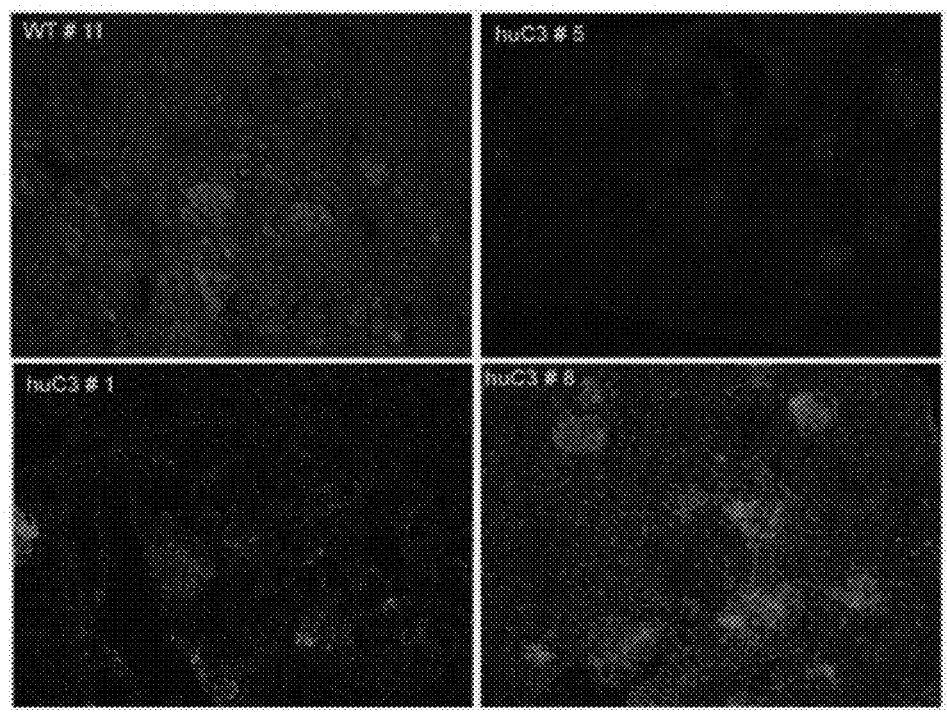
FIG. 15B depicts an immunofluorescent micrograph showing cross sections of kidney tissue obtained from wildtype (WT) and humanized C3 (huC3) mice stained for the C5b-9 membrane attack complex (red). DNA is stained blue with DAPI.
Figure 15C:
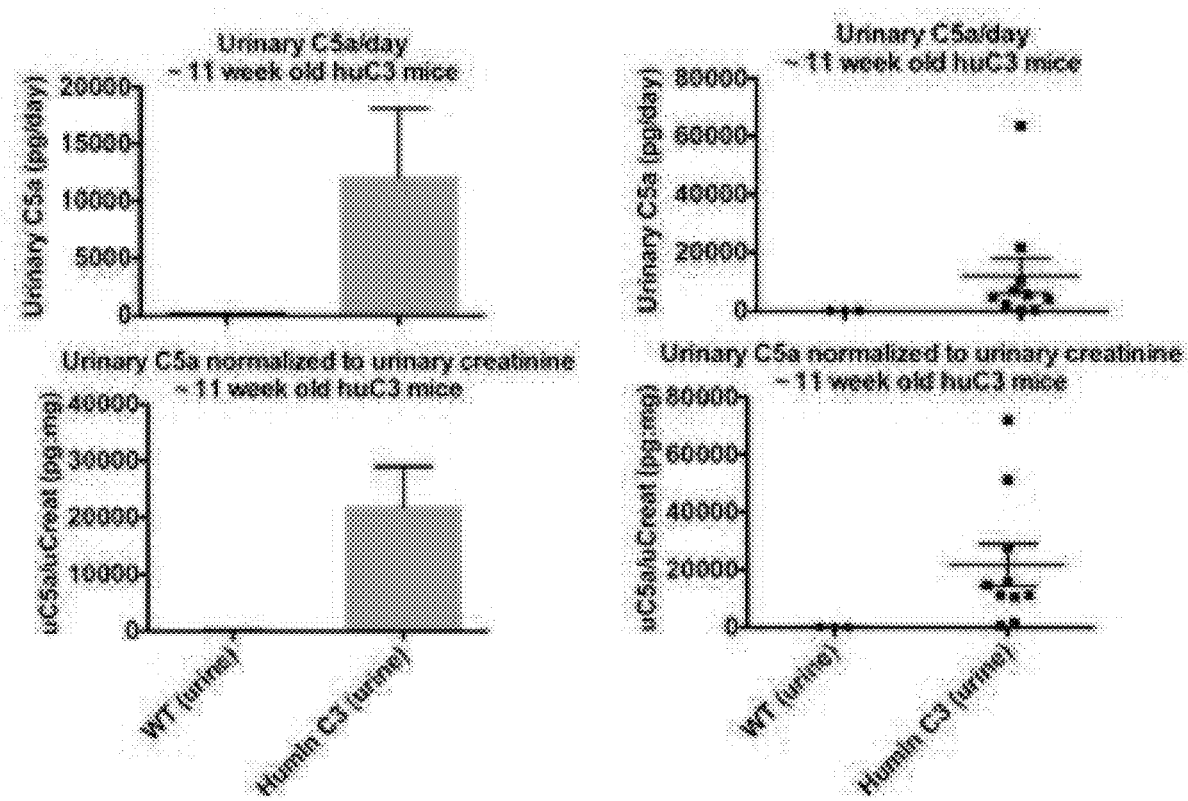
FIG. 15C depicts urinary C5a levels obtained from wildtype (WT) and humanized C3 (huC3) MAID 6149 mice.

Fluorescent staining revealed large pockets of C3 deposition in the kidneys of humanized C3 mice (FIG. 15A). Additional staining showed increased C3b-9 membrane attack complex deposition in the kidney glomerulus of huC3 mice, which is indicative of an activated complement pathway (FIG. 15B). Abnormal regulation of the alternative complement pathway, which is suggested by these findings as well as those of glomerular C3 fragment deposition and increased mesangial matrix and electron dense deposits discussed previously, correlate with nephropathies such as C3 glomerulopathy. Urinary C5a levels were measured in huC3 mice using Mouse Complement Component C5a DuoSet (R&D systems) according to manufacturer's protocol. Urinary C5a levels are highly elevated in huC3 mice compared to WT mice (FIG. 15C).

Increased C5b-9 staining in the kidney in addition to elevated urinary C5a levels suggests local activation of complement pathways in the kidneys of huC3 mice.

Example 5: RNA Sequence Signatures of C3 Humanized Mice

Determination of expressed RNA sequence signatures comparing both MAID 6149 and MAID 6156 homozygous mice against each other as well as wildtype counterparts was performed as follows.

Transcriptome Sequencing Data Generation and Read Mapping:

Total RNA was extracted from the mouse tissue samples using MagMAX kit (Life tech, Carlsbad, Calif.). mRNA was purified from 4 µg total RNA using Dynabeads® mRNA Purification Kit (Invitrogen, Waltham, Mass.). Strand-specific RNA-seq libraries were prepared using ScriptSeq™ mRNA-Seq Library Preparation Kit (Epicentre), followed by twelve PCR amplification cycles. Sequencing was performed on Illumina HiSeqE2000 (Illumina) by multiplexed single-read run with 33 cycles. Sequenced reads in Illumina Hiseq2000 image files (BCL files) were converted to FASTQ format via Illumina Casava 1.8.2. Reads were decoded based on their barcodes and merged for each individual samples. The overall read quality per sample was evaluated with FastQC to retain only samples with sufficient quality. Subsequently, the reads were mapped to mouse genome (build mm 10) using commercial software CLCBio with one allowed mismatch.

Statistical Analysis of Differentially Expressed Genes:

For each gene, the reads mapped to the sense-strand exons of the gene were identified and counted. Detectable genes are flagged based on their total exonic sense-strand read counts summarized at the gene level. An empirical minimum exonic read count of 10 was applied to determine the absence and presence of genes in each sample. For comparison between two groups of samples, genes were eliminated if they were not flagged as present in all the samples in the higher expressing group. Next, fold changes and p-values associated with the comparison were calculated using DESeq package [Genome Biology 2010, 11:R106]. Genes with a fold change (i.e., ratio) ≥1.5 in either directions and with a p-value <0.01 were selected as the significantly perturbed gene signatures.

Figure 16:
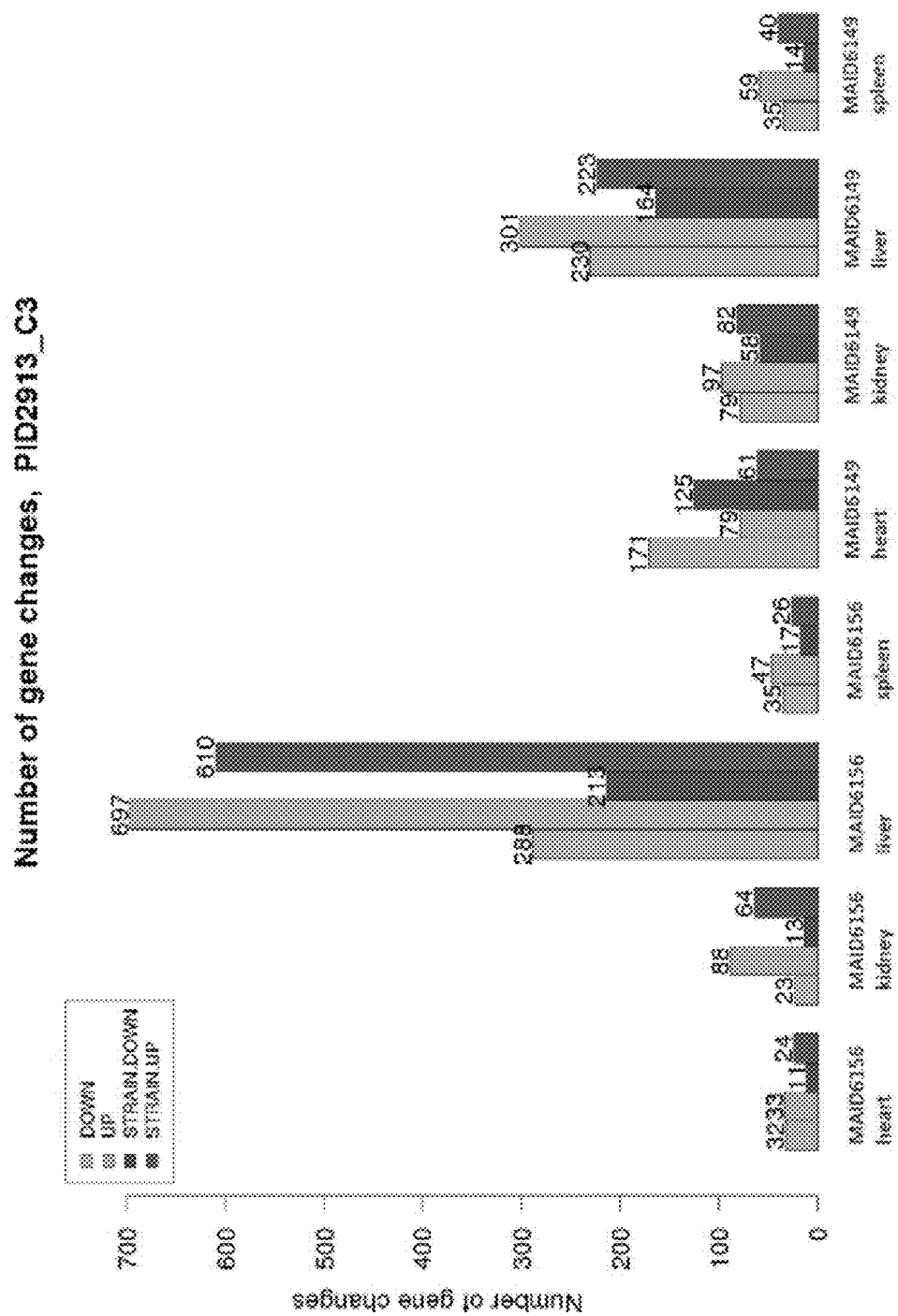
FIG. 16 depicts a bar graph showing organ-specific global changes in RNA expression in MAID 6149 and MAID 6156 homozygous (HO) mice.

As shown in FIG. 16, organ-specific analysis of RNA expression shows that, compared to wildtype counterparts, humanized C3 mice had the most gene expression changes in the liver and, to a lesser extent, the kidney. The analysis also showed that the MAID 6149 mice had a higher number of gene expression changes in the heart versus that observed in the MAID 6156 mice.

Figure 17:
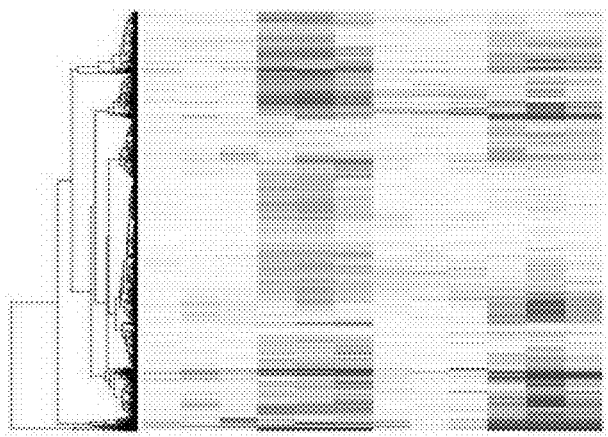
FIG. 17 depicts a gene signature map and table showing overlap among RNA signatures in the livers of MAID 6149 and MAID 6156 homozygous (HO) mice versus wildtype (WT) counterparts.
Figure 17:
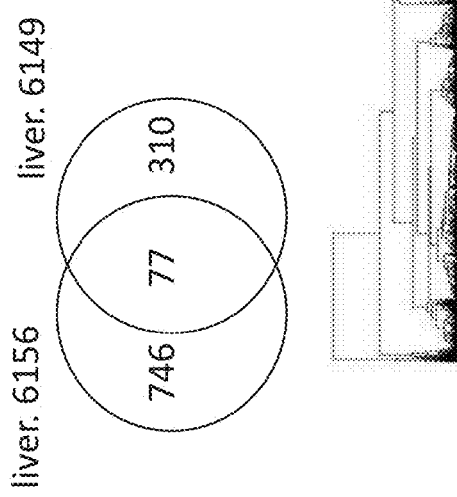
Figure 18:
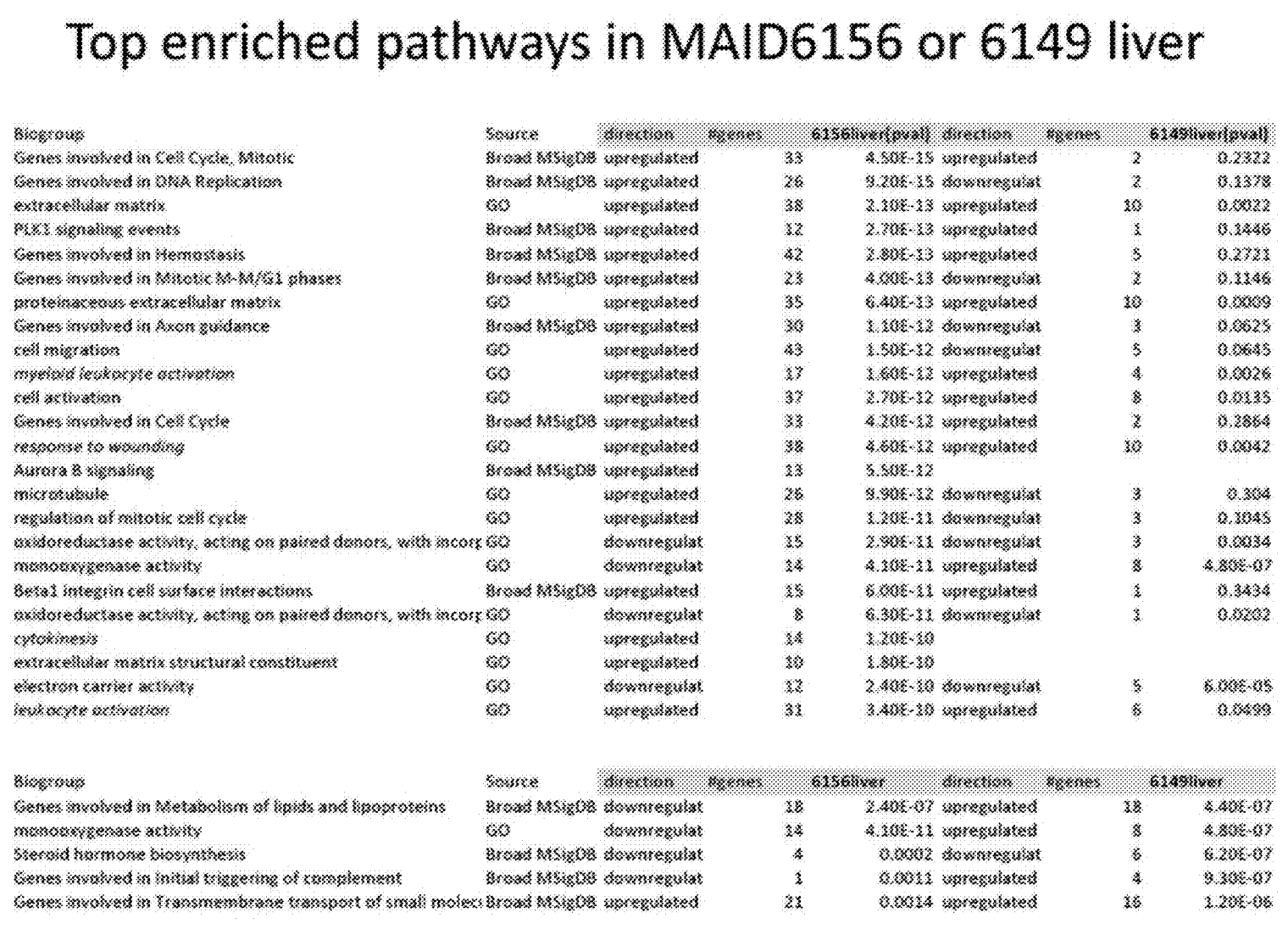

A comparison of liver gene expression signatures between MAID 6149 and MAID 6156 mice showed significant overlap in the number of genes being upregulated or downregulated between the two mouse strains (FIG. 17). The gene expression pathways being most perturbed between the two strains involved those related to the production of extracellular matrix, response to wounding, and transmembrane transport of small molecules (FIG. 18). In particular, gene expression patterns related to fibrosis of the liver was shown to be particularly elevated in MAID 6156 homozygous mice (FIG. 19).

Figure 20:
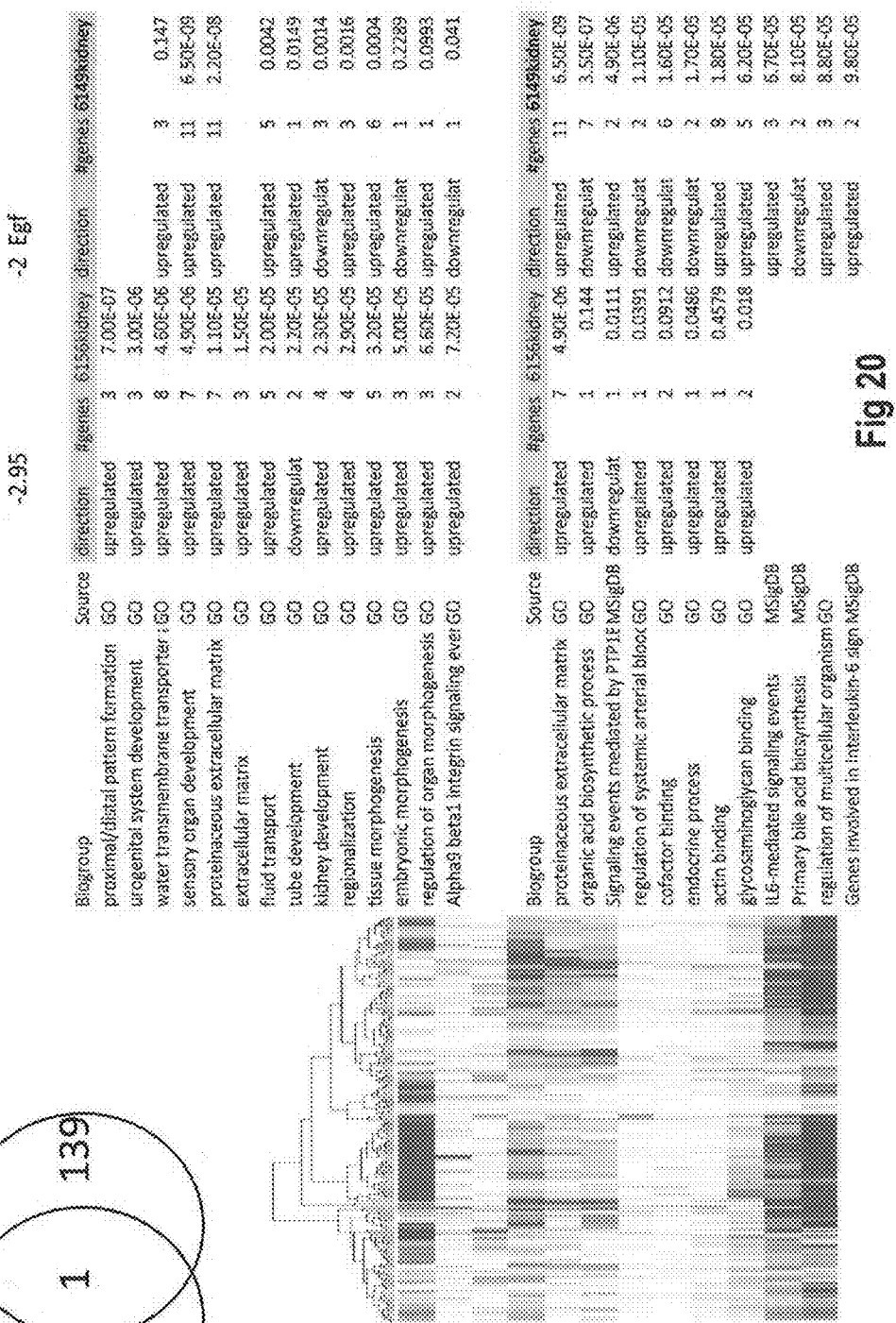
FIG. 20 depicts a gene signature map and table showing overlap among RNA signatures in the kidneys of MAID 6149 and MAID 6156 homozygous (HO) mice versus wildtype (WT) counterparts.

A similar comparison performed for the kidney showed limited gene signature overlap but overall the MAID 6149 and MAID 6156 mice shared consistency in the perturbation trend/pattern of RNA expression (FIG. 20). In particular, genes related to kidney damage were enriched in both humanized C3 strains.

Overall, the analysis of RNA expression indicates that liver genes are the most perturbed in both the MAID 6149 and MAID 6156 homozygous mouse strains. With respect to the MAID 6156 strain, genes related to cell cycle and fibrosis as well as inflammation had the most significant signatures. Inflammation and steroid metabolism gene signatures were enriched in the MAID 6149 homozygous mouse. In particular, the Tnfsf14 gene was highly upregulated in the livers of both strains of humanized C3 mice. The Tnfsf14 gene encodes the LIGHT protein, also known as tumor necrosis factor superfamily member 14 (TNFSF14), which is a secreted protein of the TNF superfamily. However, as this gene is the 3' neighbor to C3 in the mouse genome, its overexpression may be an artifact. Prok1, which is a gene that encodes a protein related to angiogenesis and development, was the top downregulated gene between the homozygous mouse strains.

Figure 21A:
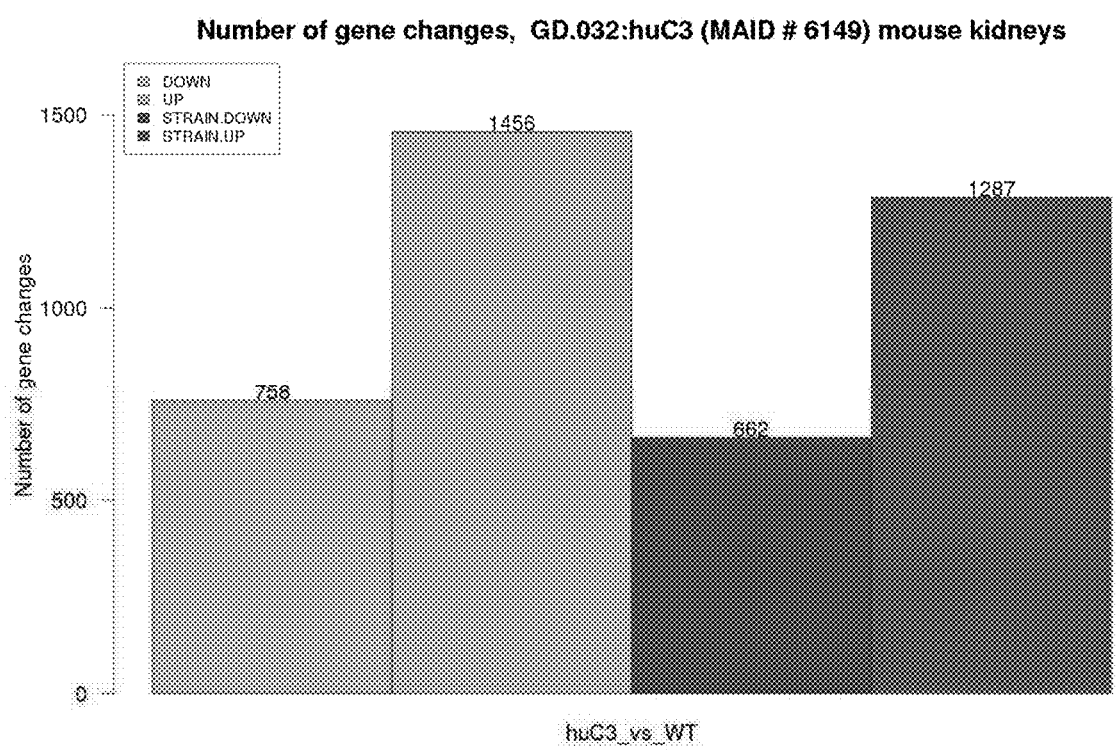
FIG. 21A depicts a bar graph showing kidney-specific gene expression changes in MAID 6149 humanized C3 (huC3) mice compared to wild-type (WT) mice.

Further characterization of gene expression in the kidneys of huC3 mice with advanced kidney disease (BUN levels in these mice are 60-120 mg/dl compared to 20-35 mg/dl in WT mice) was performed by RNASeq. huC3 mice showed several upregulated or downregulated gene expression changes (FIG. 21A). Further analysis of the data revealed upregulated expression of several nephrotoxicity genes (FIG. 21B), ECM genes (FIG. 21C), cytokines (FIG. 21D) and chemokines (FIG. 21E).

Overall, the gene expression data in the kidneys of huC3 mice with advanced kidney disease indicate ongoing injury and inflammation.

Example 6: Efficacy of Anti-C5 Antibodies in Treating Complement-Related Nephropathy As described above, mice that were humanized for C3 were found to have spontaneous mortality, normal to low hemolytic activity, low circulatory C3 (about 40 ug/mL as opposed to 1000 ug/mL seen in normal mice), and multi-organ pathology including kidney inflammation and presence of C3 depositions in the kidney.

In this Example, 8-week old C3 humanized mice were treated subcutaneously with 50 mg/kg of anti-C5 antibody M1M17628N or with isotype control, three times a week for 9 weeks. Mortality, blood urea nitrogen, serum cystatin C, urinary albumin and C5a levels were studied as described above. C3 and C5b-9 were studied by histopathological staining as described above.

Figure 22:
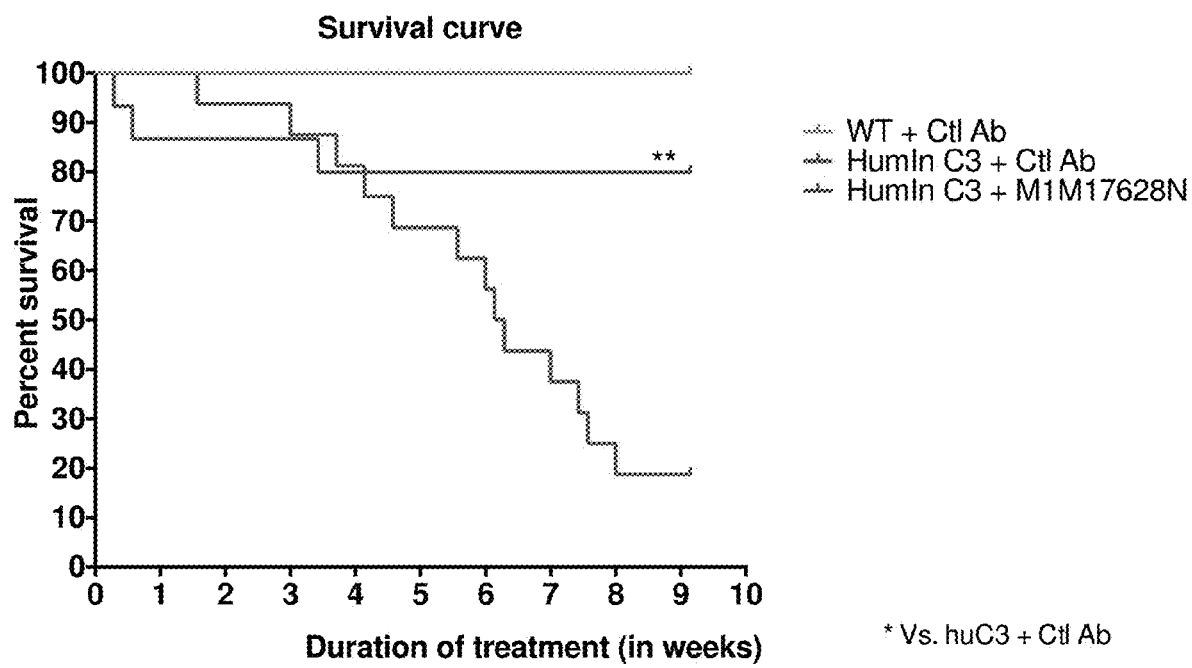
FIG. 22 depicts a survival curve of wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).
Figure 23:
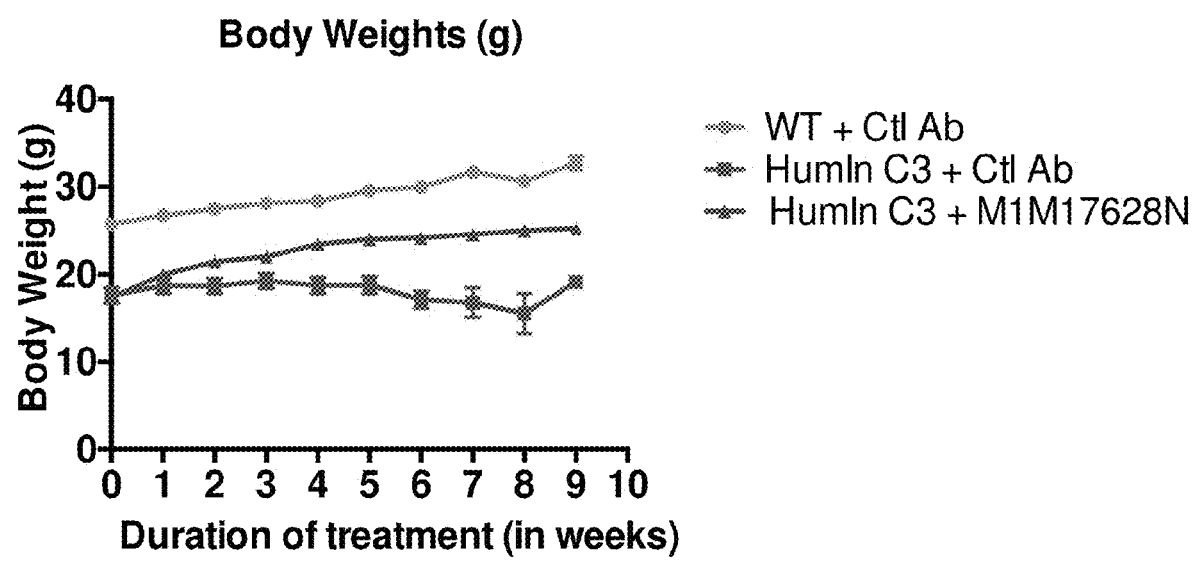
FIG. 23 depicts a graph of body weights of wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).
Figure 24A:
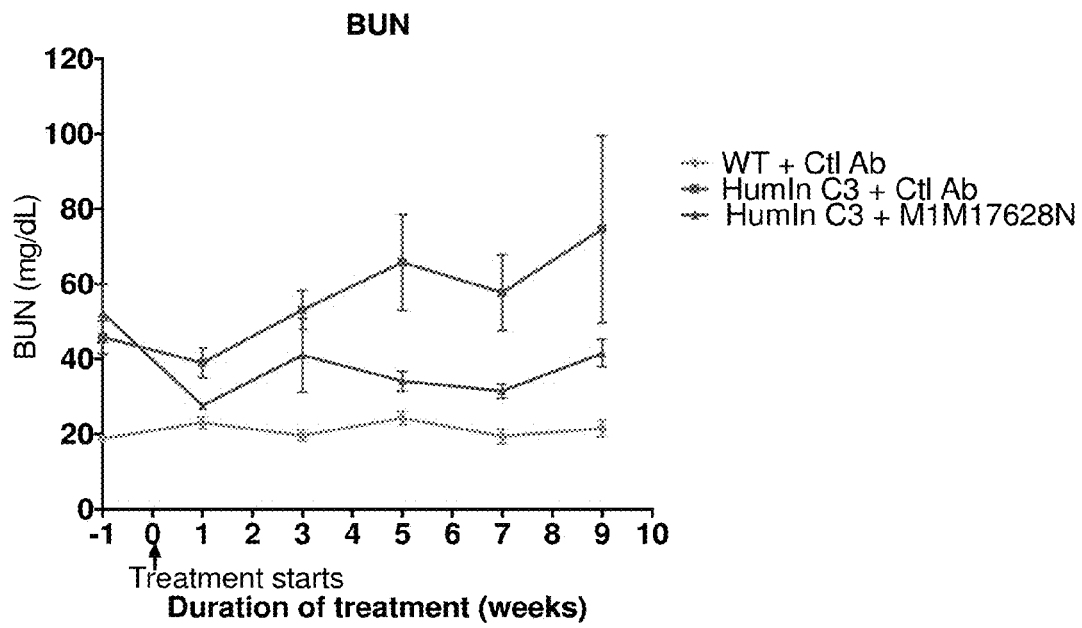
FIG. 24A and FIG. 24B depict levels of markers of kidney function in wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).
Figure 24B:
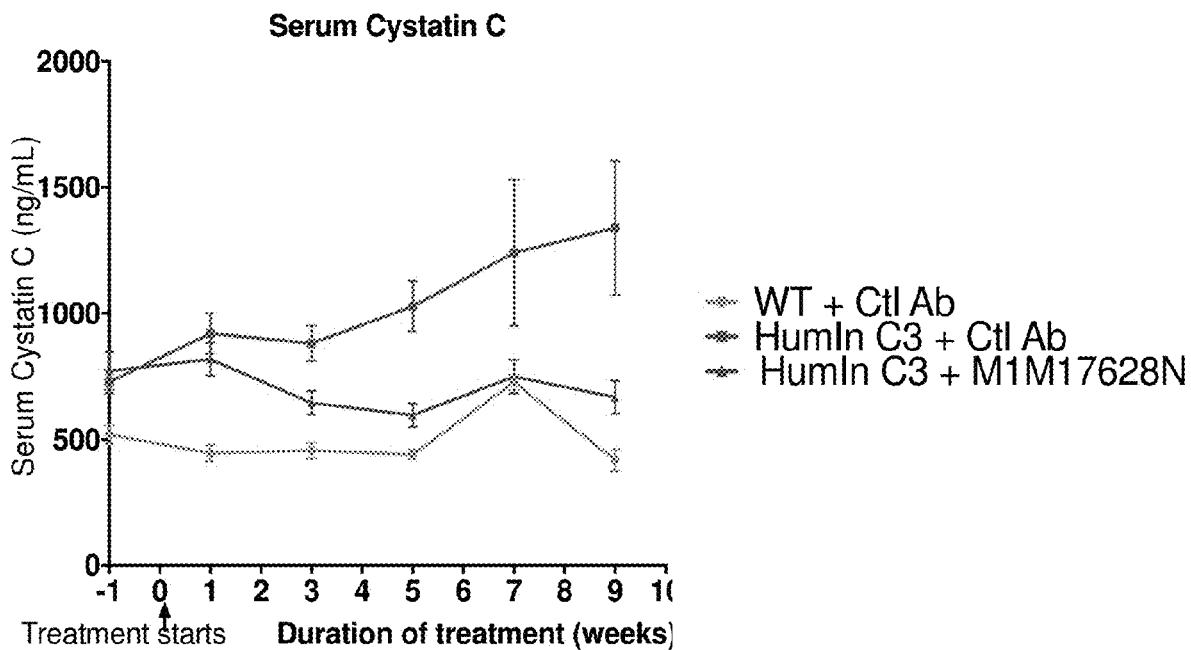
Figure 25:
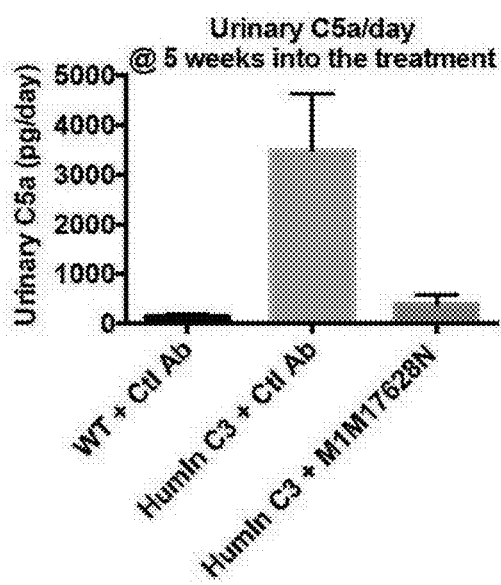
FIG. 25 depicts graphs showing urinary C5a levels (left) and normalized C5a levels (right) in wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).
Figure 25:
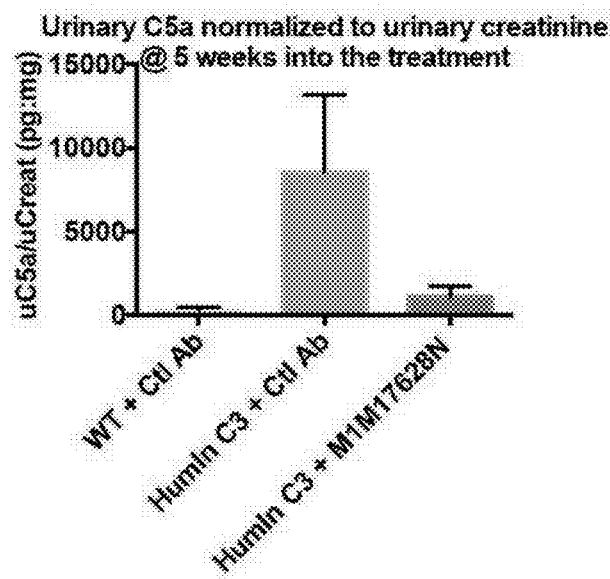

Treatment with anti-C5 antibody significantly improved survival rate in the humanized C3 mice, with mice treated with anti-C5 antibody showing only 20% mortality as compared to 81% mortality in mice treated with isotype control (FIG. 22). Treatment with anti-C5 antibody improved body weight in humanized C3 mice (FIG. 23) and improved markers of kidney function, such as BUN (FIG. 24A) and serum cystatin C (FIG. 24B). There was no effect seen on urinary albumin (data not shown), however urinary C5a levels were decreased upon treatment with anti-C5 antibody (FIG. 25).

Figure 26:
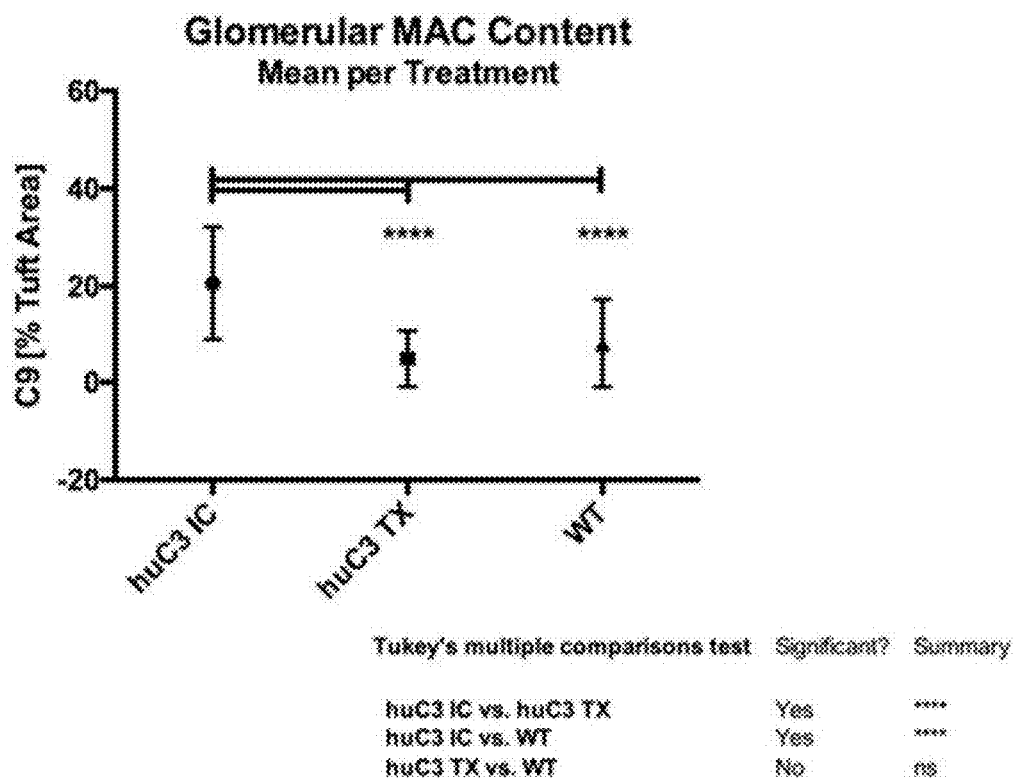
FIG. 26 depicts a graph quantifying immunofluorescent staining of glomerular membrane attack complex (MAC) content (C5b-9) in wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).
Figure 26:
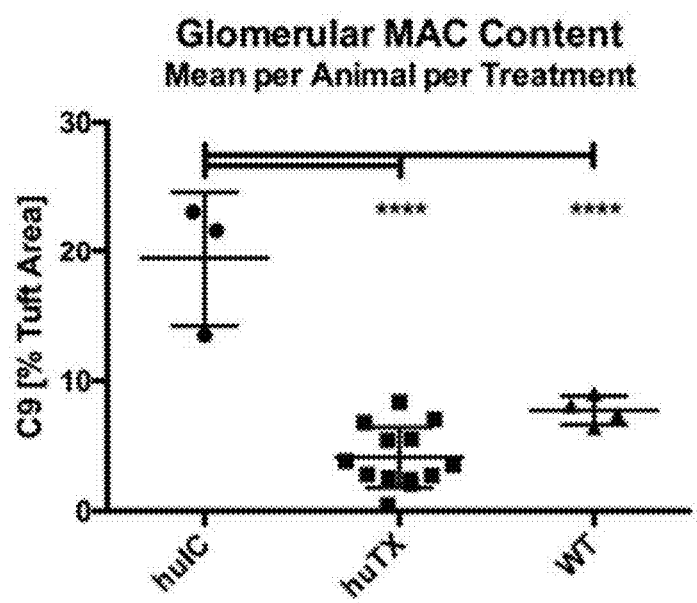
Figure 27A:
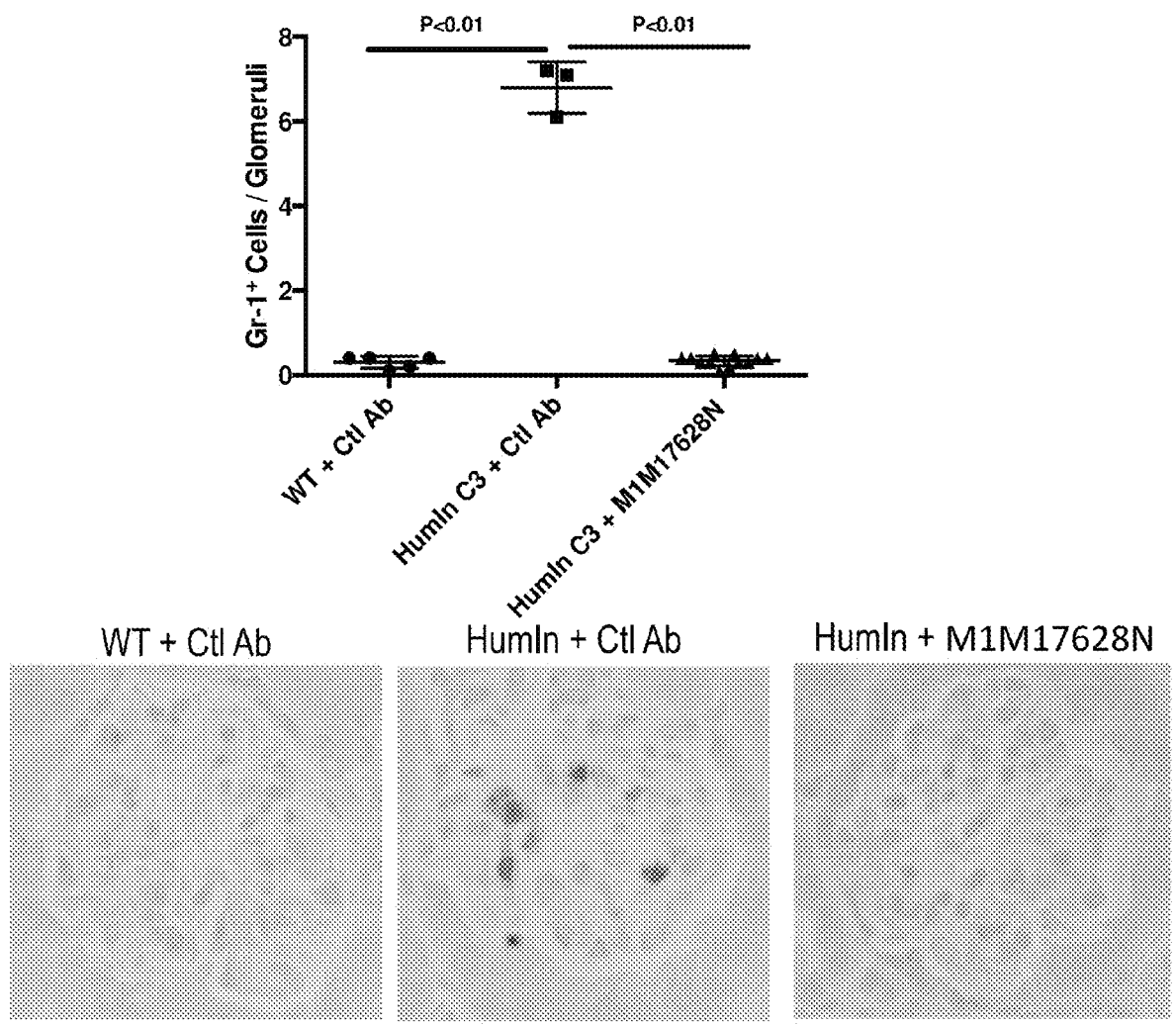
FIG. 27A depicts a graph (top) showing glomerular Gr-1$^+$ neutrophil infiltration in wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N) as well as immunohistochemical staining (bottom) for Gr-1$^+$ neutrophils in kidney tissue derived from wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).
Figure 27B:
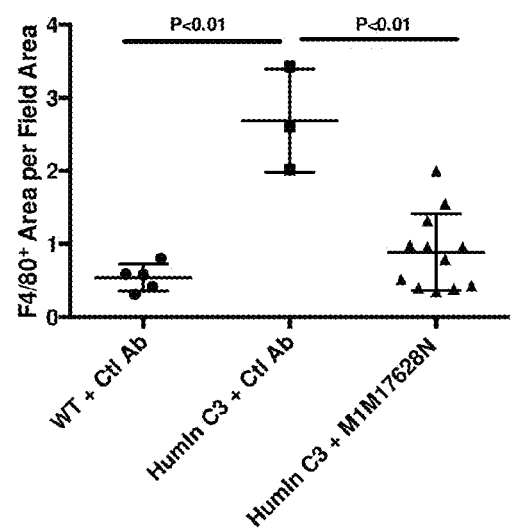
FIG. 27B depicts a graph (top) showing interstitial F4/80$^+$ macrophage infiltration in wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N) as well as immunohistochemical staining (bottom) for F4/80$^+$ macrophages in kidney tissue derived from wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).
Figure 27B:
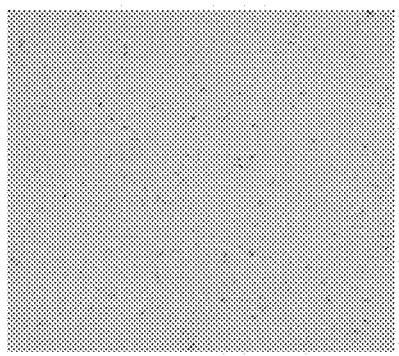
Figure 27B:
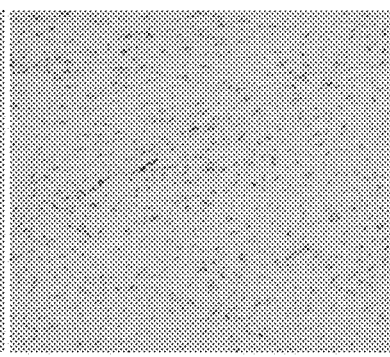
Figure 27B:
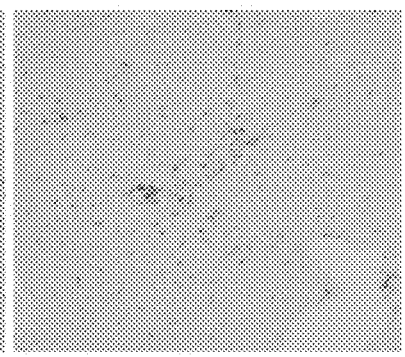
Figure 28:
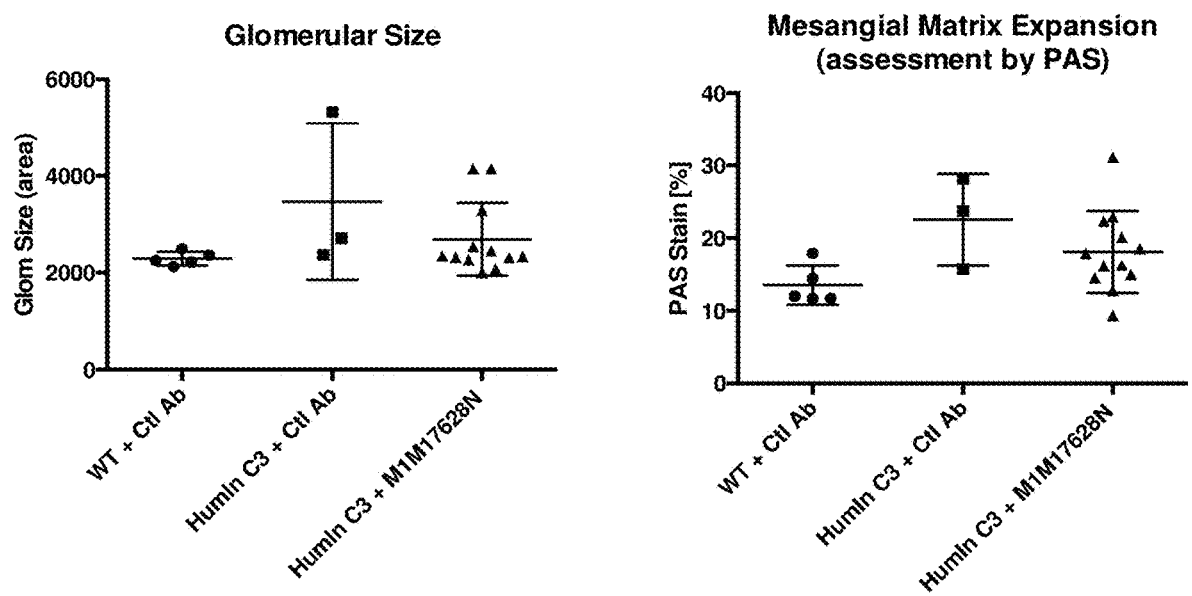
FIG. 28 depicts graphs quantifying glomerular size (left) and mesangial matrix expansion (right; assessed by PAS) in wild type mice treated with isotype control (WT+Ctl Ab), and C3 humanized MAID 6149 mice treated with isotype control (HumIn C3+Ctl Ab) or anti-C5 antibody M1M17628N (HumIn C3+M1M17628N).

Histopathological staining showed increased glomerular membrane attack complex (MAC) content (C5b-9) in C3 humanized mice treated with isotype control as compared to C3 humanized mice treated with anti-C5 antibody and wild-type mice treated with isotype control (FIG. 26). Treatment with anti-C5 antibody significantly decreased glomerular neutrophil (FIG. 27A) and interstitial macrophage infiltration (FIG. 27B) into the kidneys of the humanized C3 animals. Moreover, C3 humanized mice treated with isotype control as compared to C3 humanized mice treated with anti-C5 antibody and wild-type mice treated with isotype control exhibited increased glomerular size as well as mesangial matrix expansion (FIG. 28).

In conclusion, the results indicate that anti-C5 therapy can significantly improve mortality and kidney function as well as decrease histological signs of damage in the kidneys of rodents exhibiting symptoms of complement-related nephropathies.

Example 7: Anti-C5 Treatment LED to Profound Rescuing of Disease Gene Signature in Humanized C3 Mice (MAID 6149)

Humanized C3 mice (MAID 6149) were treated with either a mouse anti-mouse C5 antibody, or an isotype control antibody (n=16), starting at 8 weeks of age. Wild-type mice were treated with isotype control (n=5). The antibodies were administered at 50 mg/kg, subcutaneously, thrice/week. The treatment continued until 17 weeks of age. Gene expression was examined by Next Generation Sequencing (NGS) in the kidneys of survived mice at the end of the study.

Figure 29A:
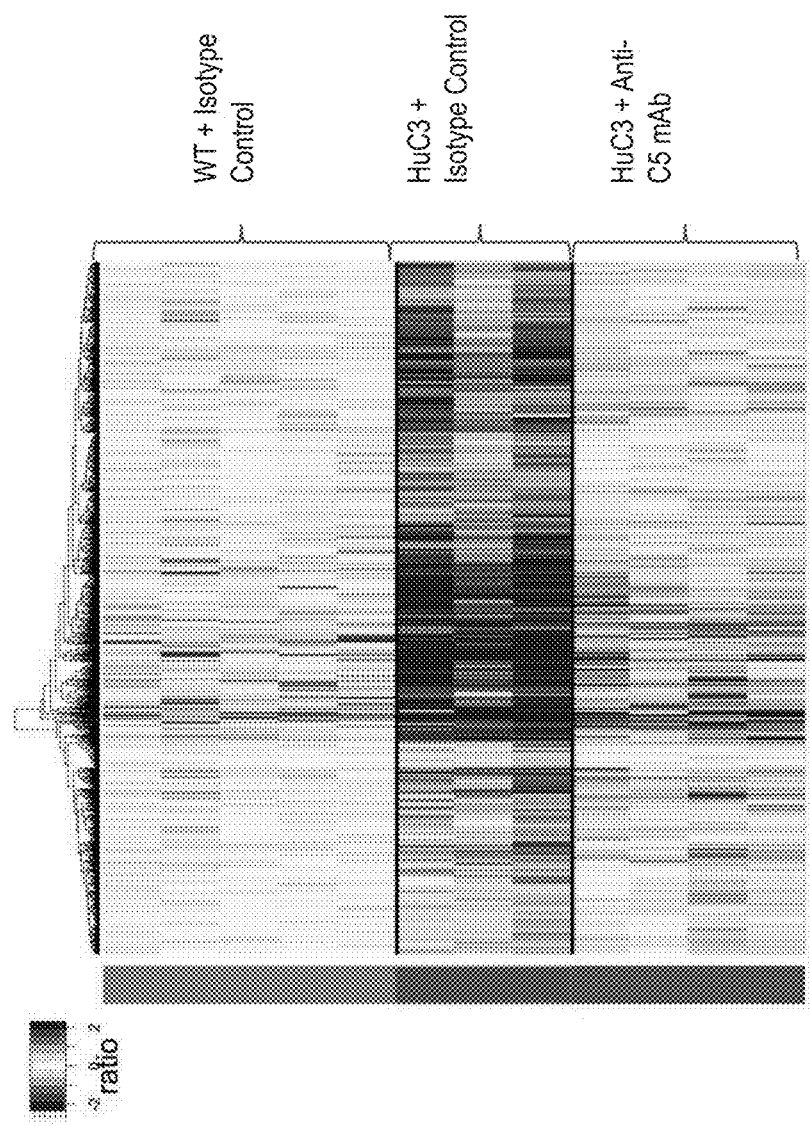
FIGS. 29A, 29B and 29C show that anti-C5 treatment led to profound rescuing of disease gene signature in humanized C3 mice (MAID 6149).
Figure 29A:
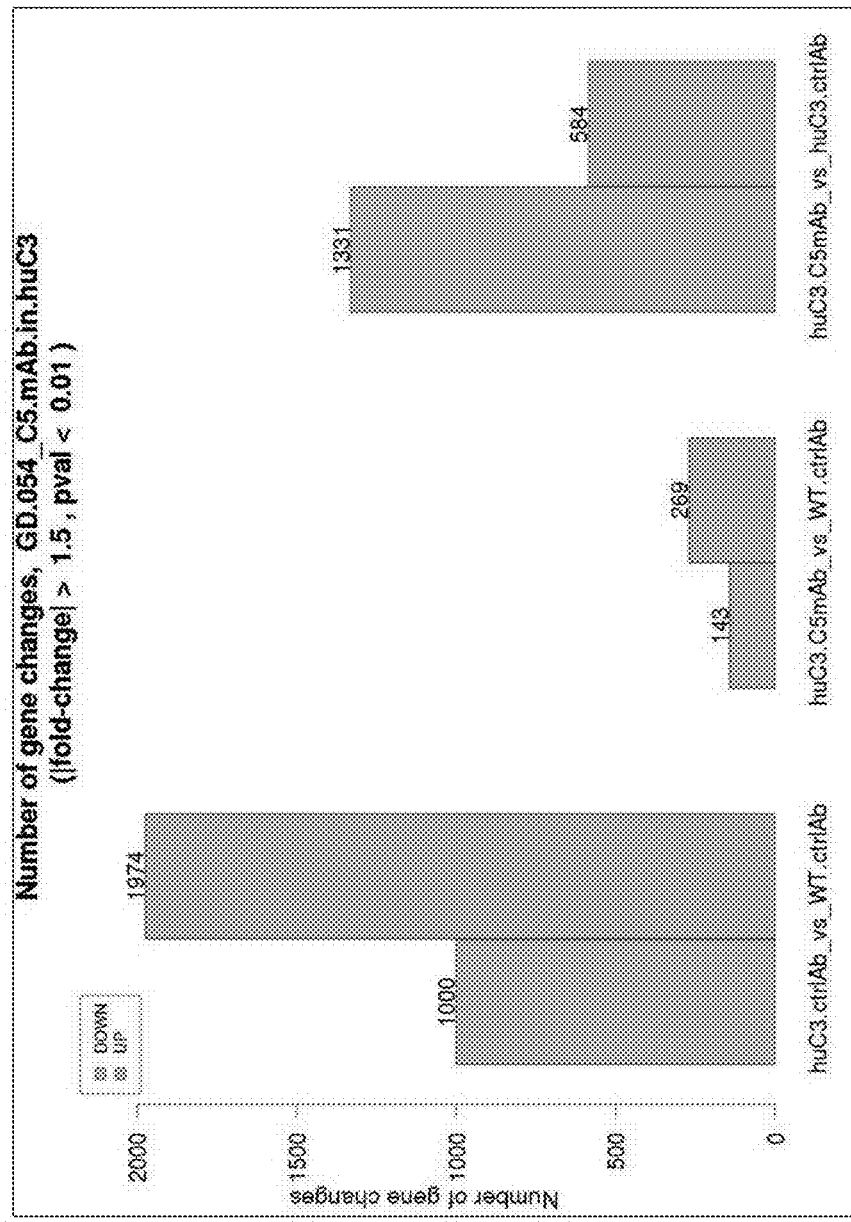
Figure 29B:
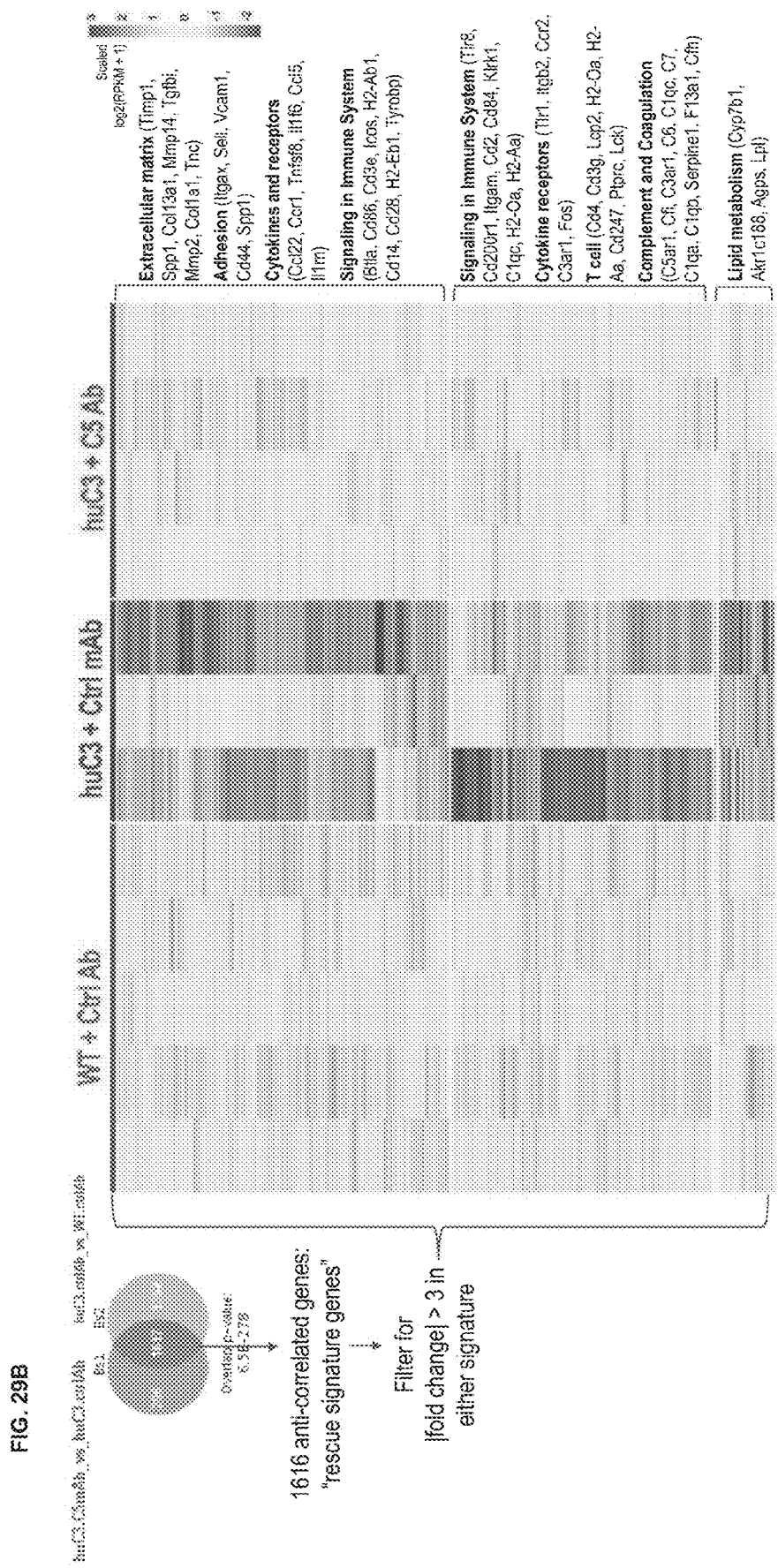
Figure 29C:
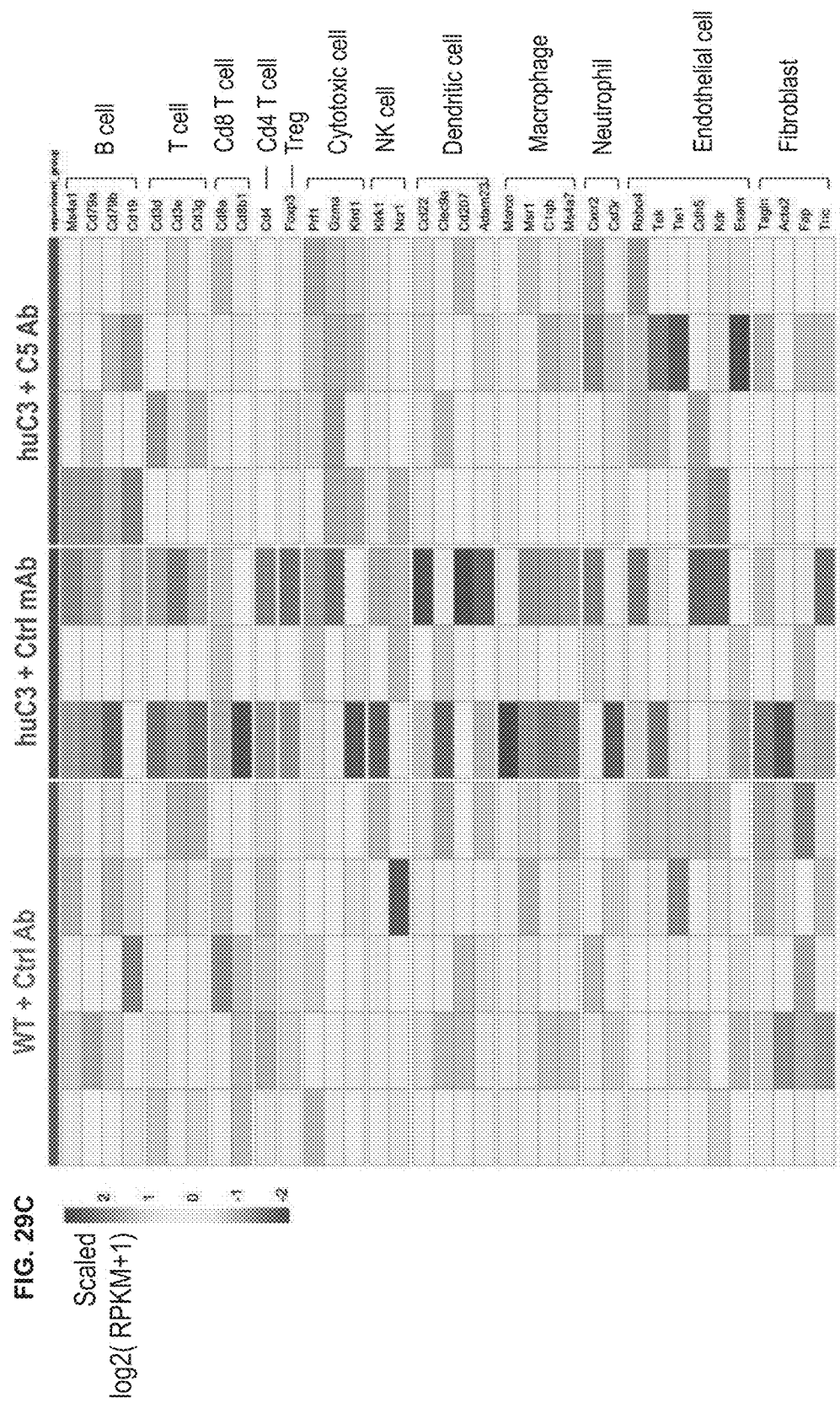

A shown in FIG. 29A, anti-C5 antibody treatment reversed disease signature genes in humanized C3 MAID 6149 mice. Rescued disease signature included immune, extracellular matrix, cytokine, complement and metabolism related genes (FIG. 29B). Immune cell type markers that were upregulated in humanized C3 mice were shown to be subsequently attenuated by anti-C5 antibody treatment (FIG. 29C).

Example 8: Continuous Blockade of C5 May be Necessary to Prolong the Survival of Humanized C3 Mice (MAID 6149)

Humanized C3 mice were treated with either a mouse anti-mouse C5 antibody, or an isotype control antibody (n=15), starting at 8 weeks of age. The antibodies were administered at 50 mg/kg, subcutaneously, thrice/week. The treatment stopped at 24 weeks of age.

Figure 30:
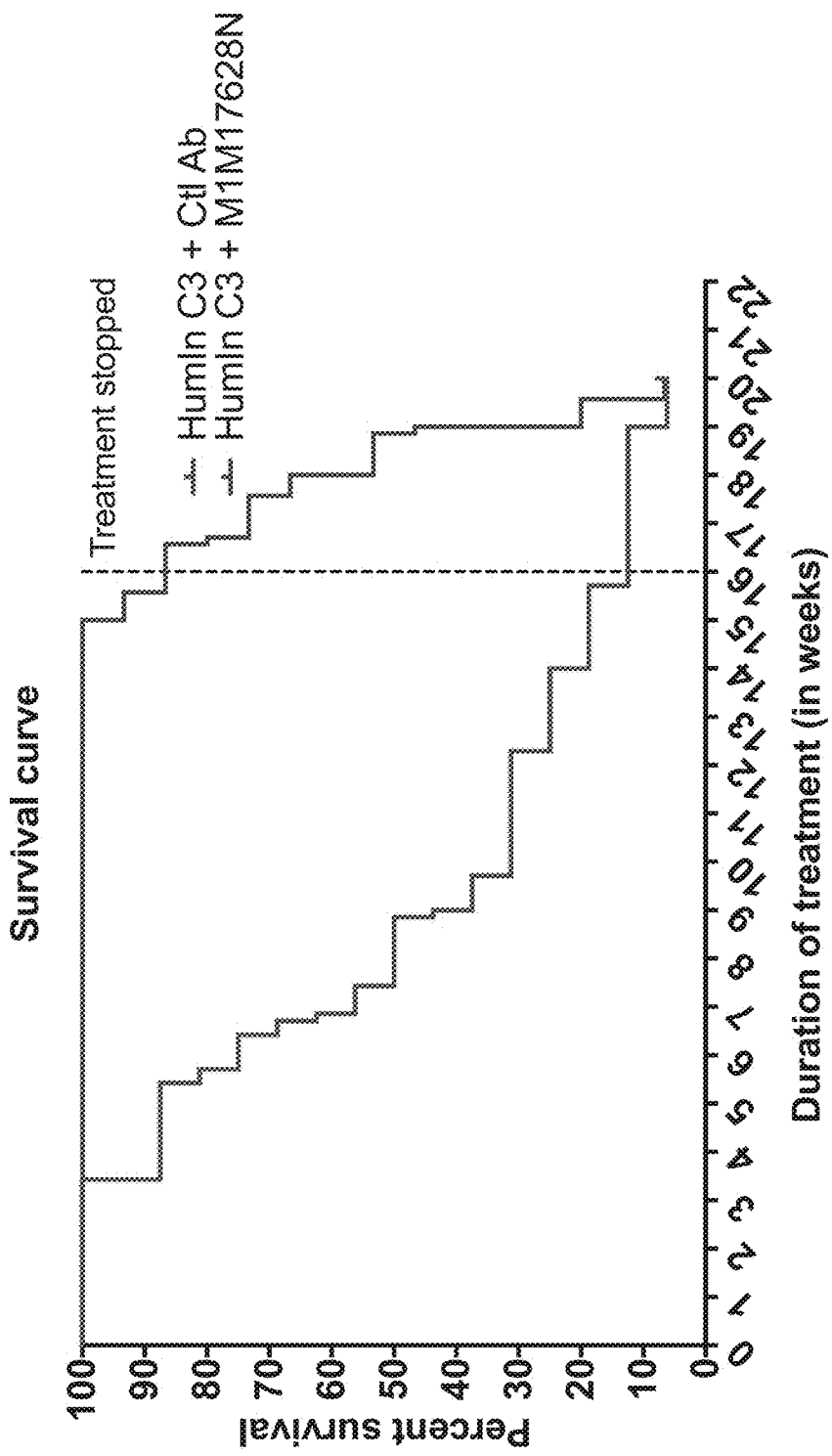
FIG. 30 show that continuous blockade of C5 prolonged the survival of humanized C3 MAID 6149 mice.

Only 2 out of 15 mice died with anti-C5 antibody during the 16-week treatment period (8-24 weeks of age). During the same time, 13 out 16 of the isotype control group died (FIG. 30). Within four weeks after stopping the treatment, several mice on anti-C5 antibody treatment died (12 of remaining 13). This data suggests that continuous blockade of C5 may be necessary to prolong the survival of humanized C3 MAID 6149 mice.

Example 9: Blockade of C3b Also Offered Protection in Humanized C3 Mice

Humanized C3 mice (MAID 6149) were treated with either an anti-C3b binding/blocking antibody (n=14) or an isotype control antibody (n=14), starting at 8 weeks of age. The antibodies were administered at 50 mg/kg, subcutaneously, thrice/week. The treatment continued until 18 weeks of age (a total of 10-week treatment period).

Figure 31A:
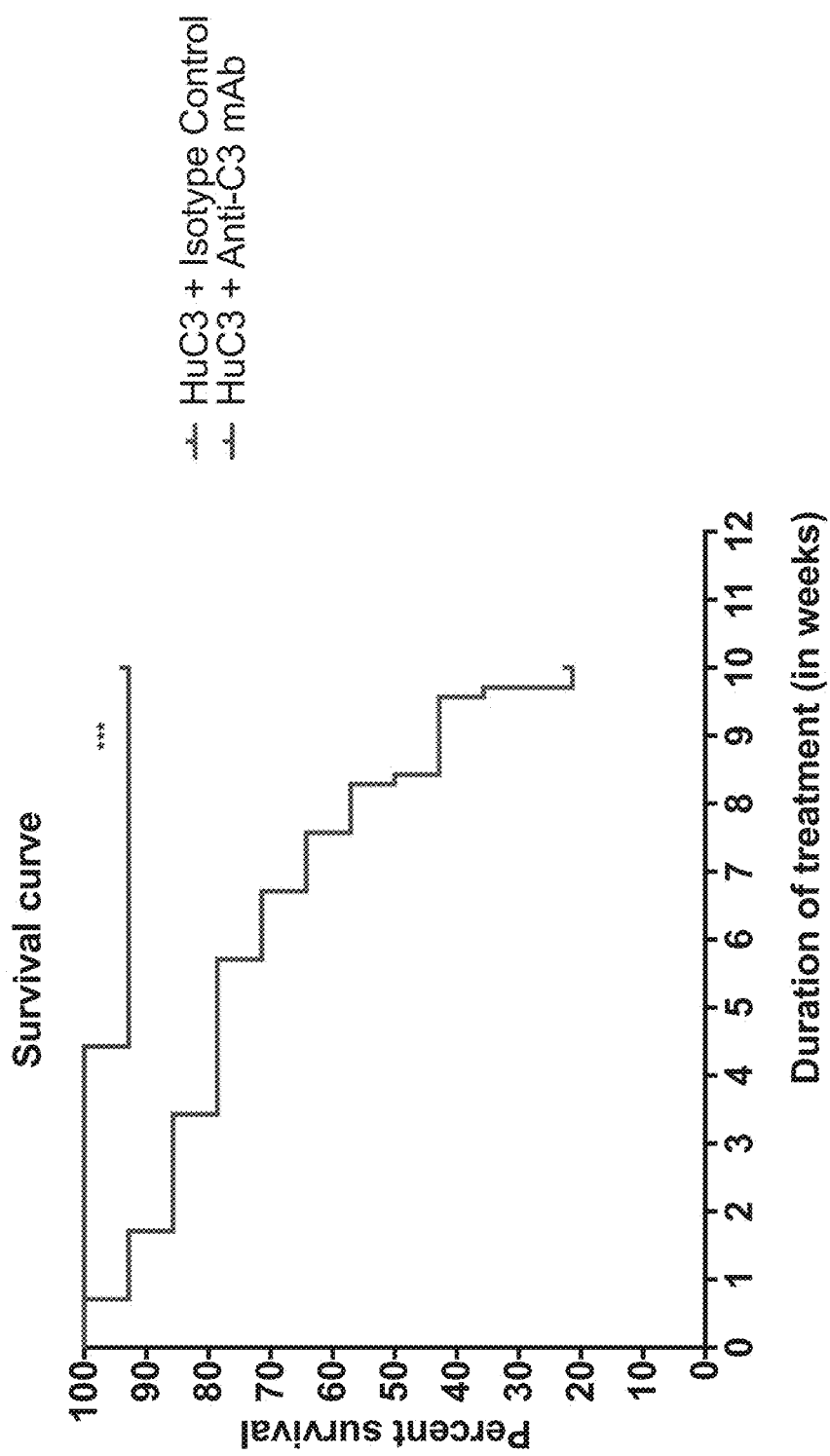
FIGS. 31A-31C show that blockade of C3b also offered protection in humanized C3 MAID 6149 mice.
Figure 31B:
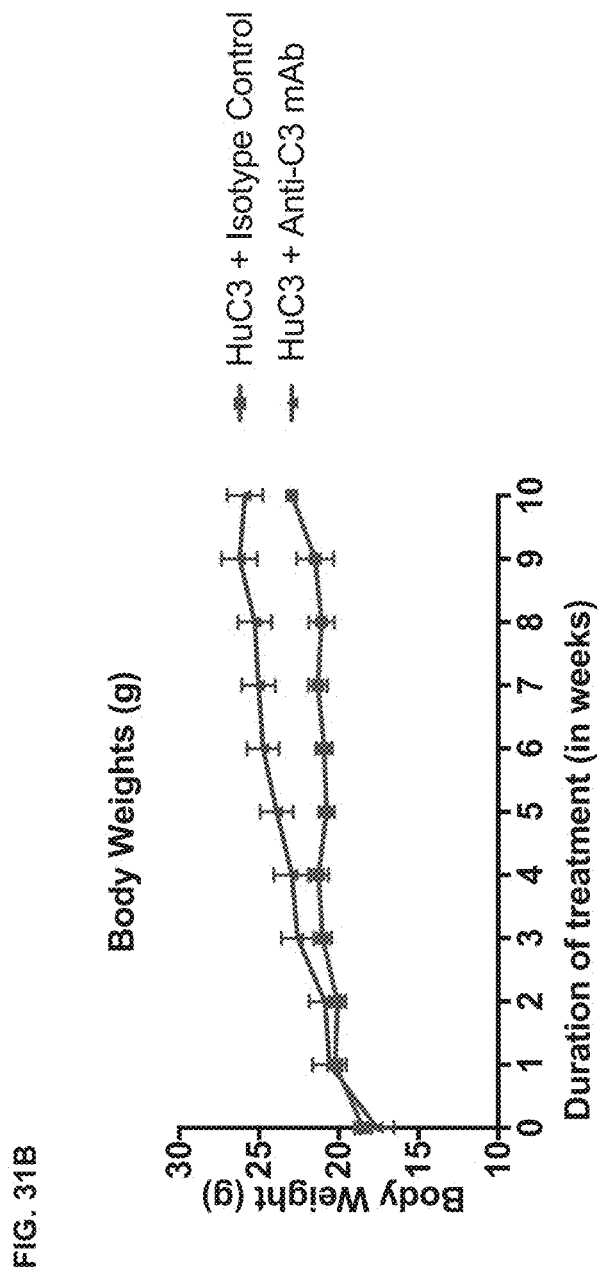
Figure 31C:
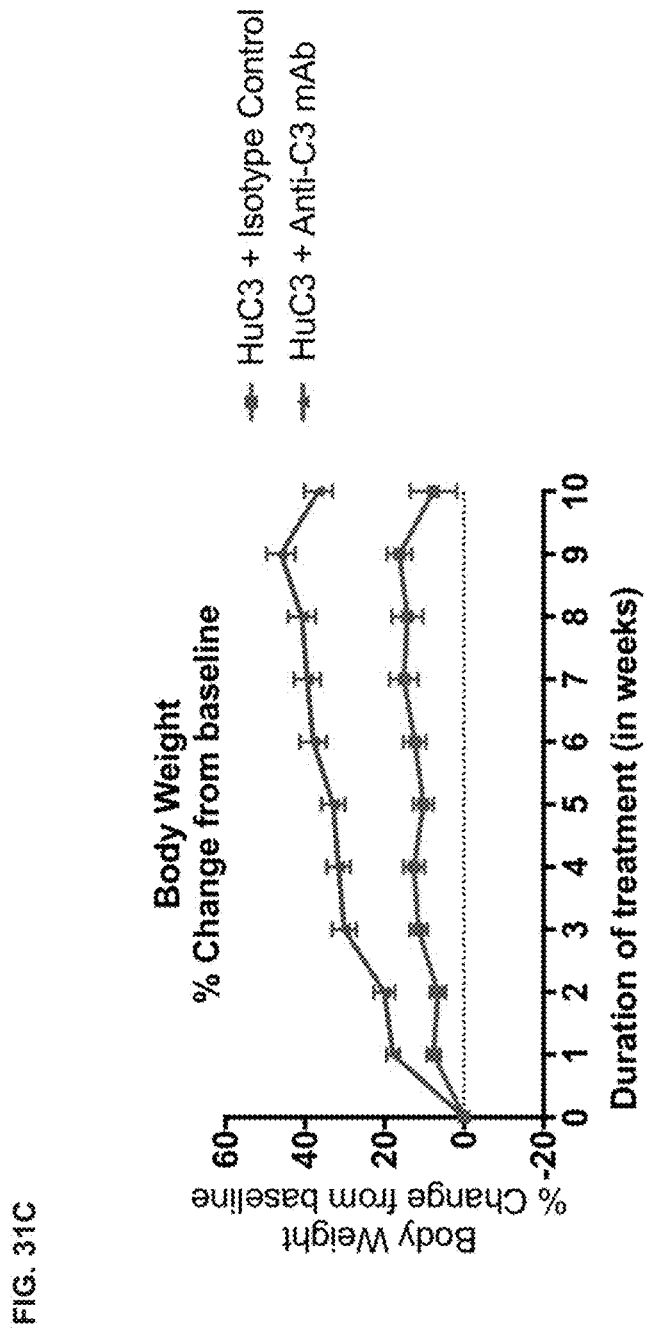

Eleven out 14 mice with the isotype control died during the 10-week study period (FIG. 31A). Only 1 out of 14 mice died with anti-3b antibody during the same time suggesting that C3b blockade provided significant survival benefit in humanized C3 MAID 6149 mice. Anti-C3b blocking antibody also improved body weight in the humanized C3 mice suggesting improvement in health status (FIG. 31B and FIG. 31C). Overall, these data indicate blockade of C3b, upstream of C5, also offers protection in humanized C3 mice.

What is claimed is:

1. A method for assessing the in vivo therapeutic efficacy of an agent for use in a treatment of a complement-related nephropathy, the method comprising:
   (a) administering the agent to a mouse whose genome comprises a replacement at an endogenous mouse C3 locus to form a modified C3 gene,
   wherein the replacement is (i) a replacement of a mouse gene sequence comprising exon 1 through exon 41 of the mouse C3 gene with a nucleic acid sequence comprising exon 1 through exon 41 of the human C3 ene, or (ii) a replacement of a mouse gene sequence comprising exon 2 through exon 41 of the mouse C3 gene with a nucleic acid sequence comprising exon 2 through exon 41 of the human C3 gene,
   wherein expression of the modified C3 gene is under control of mouse regulatory elements at the endogenous mouse C3 locus, wherein the mouse spontaneously exhibits one or more symptoms of the complement-related nephropathy; and
   (b) measuring the one or more symptoms of the complement-related nephropathy in the mouse, and categorizing the agent as a therapeutic agent for treating the complement-related nephropathy when the agent inhibits the one or more symptoms of the nephropathy compared to control mice who have not been administered the agent,
   wherein the one or more symptoms of the nephropathy are selected from the group consisting of
   (i) one or more of glomerulonephritis, basophilic tubules, sclerotic glomeruli, dilated tubules with protein casts, mesangial matrix expansion, glomerular hypertrophy, mononuclear interstitial inflammation,
   (ii) C3 protein deposition in the kidney,
   (iii) deposition of C5b-9 membrane attack complexes in the kidney,
   (iv) one or more of elevated blood urea nitrogen (BUN), serum lipase, serum cystatin C, or serum non-high density lipoproteins, and
   (v) increased urinary albumin or C5a.

2. The method of claim 1, wherein the mouse is incapable of expressing a mouse C3 protein.

3. The method of claim 2, wherein the mouse expresses a mouse C5 protein encoded by an endogenous mouse C5 gene.

4. The method of claim 1, wherein the agent is selected from the group consisting of small molecule chemical compounds, peptides and antibodies.

5. The method of claim 4, wherein the agent is an antibody.

6. The method of claim 1, wherein the agent is an inhibitory nucleic acid.

7. The method of claim 1, wherein the one or more symptoms of the nephropathy are selected from one or more of the group consisting of glomerulonephritis, basophilic tubules, sclerotic glomeruli, dilated tubules with protein casts, mesangial matrix expansion, glomerular hypertrophy, and mononuclear interstitial inflammation.

8. The method of claim 1, wherein the one or more symptoms of the nephropathy comprise C3 protein deposition in the kidney.

9. The method of claim 1, wherein the one or more symptoms of the nephropathy comprise deposition of C5b-9 membrane attack complexes in the kidney.

10. The method of claim 1, wherein the one or more symptoms of the nephropathy comprise one or more of elevated blood urea nitrogen (BUN), serum lipase, serum cystatin C, or serum non-high density lipoproteins.

11. The method of claim 1, wherein the one or more symptoms of the nephropathy comprise increased urinary albumin or C5a.

12. A method for assessing the in vivo therapeutic efficacy of an agent for use in a treatment for fibrosis of the liver, the method comprising:
   (a) administering the agent to a mouse which comprises a replacement at an endogenous mouse C3 locus to form a modified C3 gene,
   wherein the replacement is (i) a replacement of a mouse gene sequence comprising exon 1 through exon 41 of the mouse C3 gene with a nucleic acid sequence comprising exon 1 through exon 41 of the human C3 gene, or (ii) a replacement of a mouse gene sequence comprising exon 2 through exon 41 of the mouse C3 gene with a nucleic acid sequence comprising exon 2 through exon 41 of the human C3 gene
   wherein expression of the modified C3 gene is under control mouse regulatory elements at the endogenous mouse C3 locus, wherein the mouse spontaneously exhibits one or more symptoms of fibrosis of the liver; and
   (b) measuring the one or more symptoms of fibrosis of the liver in the mouse and categorizing the agent as a therapeutic agent for treating fibrosis of the liver when the agent inhibits the one or more symptoms of fibrosis of the liver compared to control mice who have not been administered the agent.

13. The method of claim 12, wherein the mouse is incapable of expressing a mouse C3 protein.

14. The method of claim 13, wherein the mouse expresses a mouse C5 protein encoded by an endogenous mouse C5 gene.

15. The method of claim 12, wherein the agent is selected from the group consisting of small molecule chemical compounds, peptides and antibodies.

16. The method of claim 12, wherein the agent is an inhibitory nucleic acid.

* * * * *